(12) United States Patent
Lueck

(10) Patent No.: US 6,609,070 B1
(45) Date of Patent: *Aug. 19, 2003

(54) FLUID TREATMENT APPARATUS

(75) Inventor: Stanley R. Lueck, Farmington, NM (US)

(73) Assignee: RODI Systems Corp, Aztec, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/712,483

(22) Filed: Nov. 13, 2000

Related U.S. Application Data

(63) Continuation-in-part of application No. 09/336,184, filed on Jun. 18, 1999.
(60) Provisional application No. 60/089,861, filed on Jun. 19, 1998.

(51) Int. Cl.[7] .............................................. G01F 23/00
(52) U.S. Cl. ..................... 702/50; 700/266; 73/61.56; 210/614; 210/96.1
(58) Field of Search .................. 702/50; 700/2–3, 700/47, 9, 83, 266, 267, 271; 210/614, 739, 741–746, 96.1; 73/53.01, 61.68, 61.56

(56) References Cited

U.S. PATENT DOCUMENTS

| | | |
|---|---|---|
| RE29,383 E | 9/1977 | Gallatin et al. |
| 4,498,982 A | 2/1985 | Skinner |

(List continued on next page.)

OTHER PUBLICATIONS

Anderson, C., ed., *RODI News*, Aug., 1998, pp. 1–3, Creative Geckos, Farmington, New Mexico.
*AquaLynx™ 400, General Operating Manual*, Oct., 1998, RODI Systems Corp., Aztec, New Mexico.
*AquaLynx™ 400 Hardware Manual Version 1.3*, Feb., 1999, RODI Systems Corp., Aztec, New Mexico.
*Automated RO Monitoring Technology from RODI Systems*, Aug., 1999, RODI Systems Corp., Aztec, New Mexico.
*Technical Bulletin, AquaLynx™ vs. PLCs*, Oct., 1998, RODI Systems Corp., Aztec, New Mexico.

*Primary Examiner*—Michael Nghiem
*Assistant Examiner*—Hien Vo
(74) *Attorney, Agent, or Firm*—Jeffrey D. Myers

(57) ABSTRACT

A fluid monitoring and control apparatus and method including providing a programmable and reprogrammable control unit comprising a display, user inputs, and input/output connections; placing a programmable logic controller in direct communication with the control unit, which programmable logic controller is programmable and reprogrammable through the control unit; and placing a plurality of fluid parameter sensors in direct communication with the control unit. The invention is also of a fluid control apparatus and method comprising providing a membrane and estimating salt rejection by the membrane.

22 Claims, 38 Drawing Sheets

U.S. PATENT DOCUMENTS

| | | | | |
|---|---|---|---|---|
| 4,514,304 A | * | 4/1985 | Miyaki et al. | 210/500.34 |
| 4,583,170 A | | 4/1986 | Carlin et al. | |
| 4,587,518 A | | 5/1986 | King | |
| 4,717,425 A | * | 1/1988 | Lefebvre | 127/10 |
| 4,830,757 A | | 5/1989 | Lynch et al. | |
| 4,849,098 A | | 7/1989 | Wilcock et al. | |
| 5,091,863 A | | 2/1992 | Hungerford et al. | |
| 5,172,332 A | | 12/1992 | Hungerford et al. | |
| 5,299,141 A | | 3/1994 | Hungerford et al. | |
| 5,320,760 A | | 6/1994 | Freund et al. | |
| 5,325,884 A | | 7/1994 | Mirel et al. | |
| 5,351,705 A | | 10/1994 | Reinders et al. | |
| 5,384,709 A | | 1/1995 | Seder et al. | |
| 5,422,014 A | | 6/1995 | Allen et al. | |
| 5,519,636 A | | 5/1996 | Stoll et al. | |
| 5,566,717 A | | 10/1996 | Robert | |
| 5,578,213 A | * | 11/1996 | Miller et al. | 210/259 |
| 5,633,809 A | | 5/1997 | Wissenbach et al. | |
| 5,646,863 A | | 7/1997 | Morton | |
| 5,647,973 A | | 7/1997 | Desaulniers | |
| 5,647,986 A | | 7/1997 | Nawathe et al. | |
| 5,687,091 A | | 11/1997 | Maung et al. | |
| 5,696,696 A | | 12/1997 | Gunther et al. | |
| 5,744,072 A | | 4/1998 | Karliner | |
| 5,779,911 A | | 7/1998 | Haug et al. | |
| 5,808,909 A | | 9/1998 | Rees | |
| 5,852,563 A | | 12/1998 | Weber et al. | |
| 5,923,571 A | | 7/1999 | Gunther et al. | |
| 5,967,167 A | | 10/1999 | Johnson | |
| 6,035,240 A | | 3/2000 | Moorehead et al. | |
| 6,074,551 A | * | 6/2000 | Jones et al. | 210/106 |

* cited by examiner

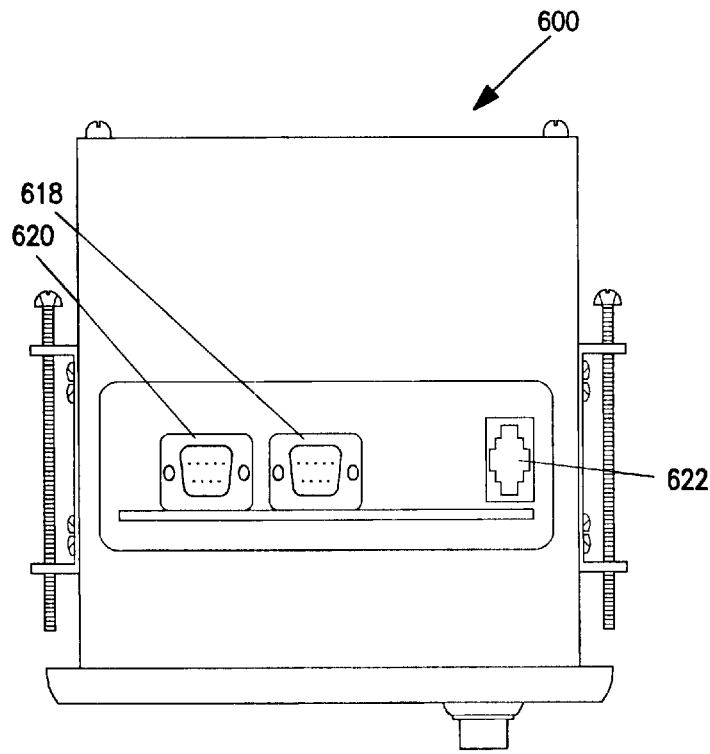
FIG-29
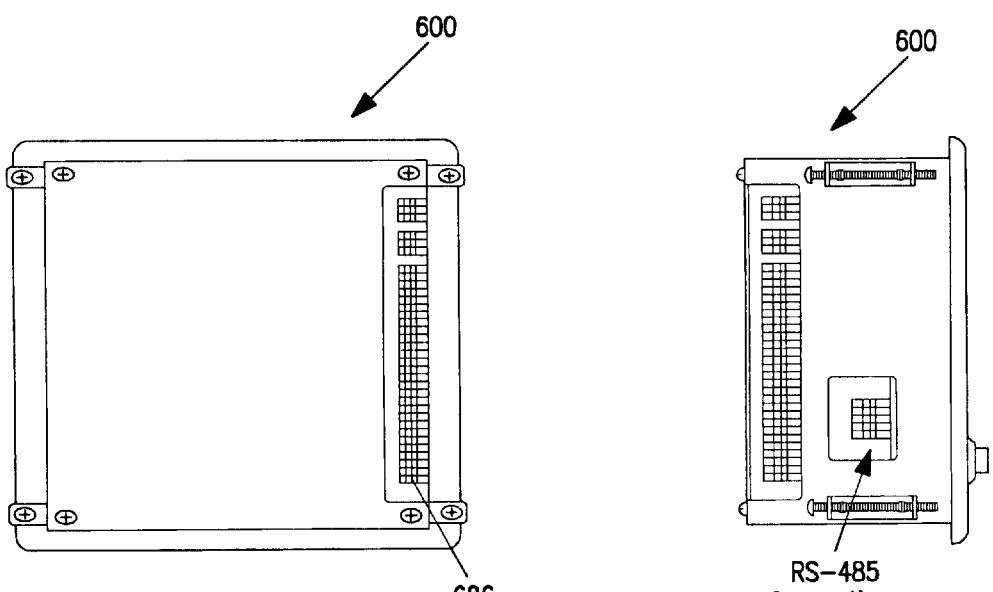
FIG-30(A)
FIG-30(B)
RS-485
Connections
(Serial Port 1)

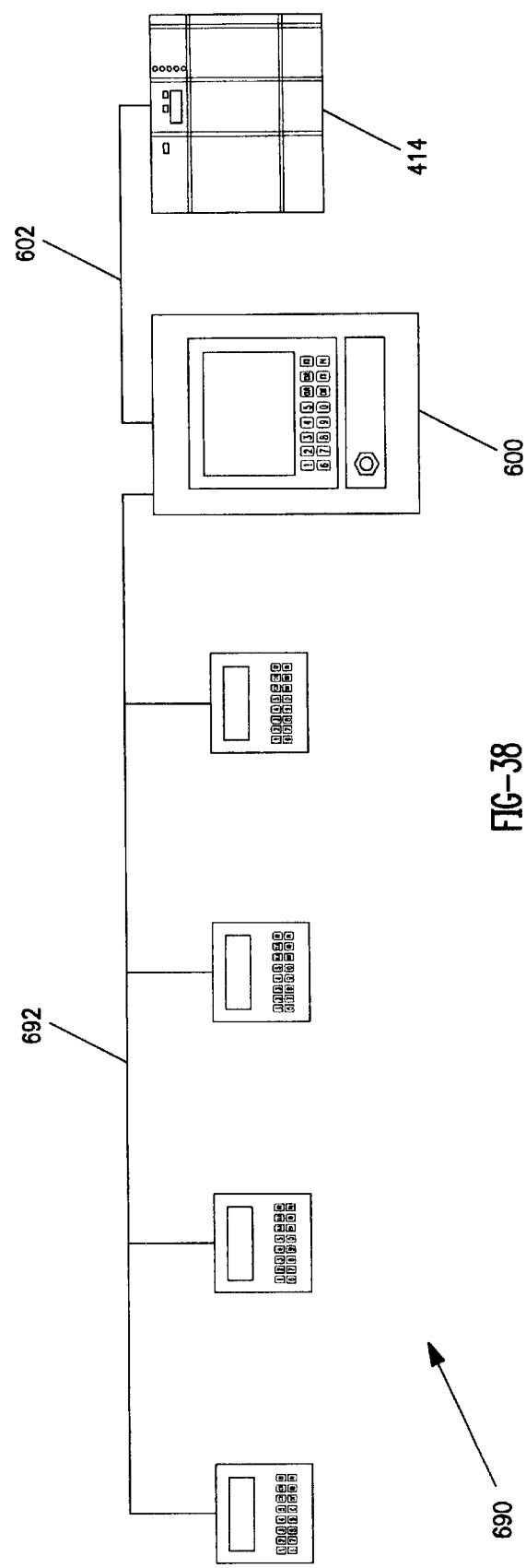

FLUID TREATMENT APPARATUS

CROSS-REFERENCE TO RELATED APPLICATIONS

This application is a continuation-in-part application of U.S. patent application Ser. No. 09/336,184, entitled "Fluid Treatment Apparatus", to Stanley R. Lueck, filed on Jun. 18, 1999, which application claimed the benefit of the filing of U.S. Provisional Patent Application Serial No. 60/089,861 entitled "Aqualynx Water Treatment Apparatus", filed on Jun. 19, 1998, and the specifications thereof are incorporated herein by reference.

BACKGROUND OF THE INVENTION

1. Field of the Invention (Technical Field)

The present invention relates to the field of fluid monitoring and treatment apparatuses.

2. Background Art

Many different instruments are required to measure the parameters of wastewater, process water, and other fluids that are sampled. Maintaining these individual components and tracking the data from these individual components is cumbersome. For example, samplers, flow meters, pH meters, temperature gauges, conductivity and ORP meters, etc., are all used to monitor and track the quality of wastewater, process water, or other fluid being sampled. In fact, most water treatment monitoring systems today comprise an assortment of individual meters and gauges. These individual components are not integrated.

Currently, microprocessor-based control systems are being used in modern industrial processes, including water treatment applications and programmable logic controllers (PLCs) are microprocessor-based. Programmable logic controllers were designed to be a microprocessor-based replacement for hardwired relay logic historically used in industrial control systems. PLCs are programmed to simulate the same type of control that could be accomplished by sets of relays and timers. This is referred to as logic control. Logic control allows certain specific actions to occur based upon other actions or conditions. PLCs have the ability to quickly scan inputs and control outputs based upon the condition of the inputs. However, most PLCs do not have any provisions for storing data (referred to as data logging) or for displaying data on a screen without an additional operator interface.

PLCs also do not have the ability to obtain data directly from water treatment sensors such as pH, ORP, conductivity, etc. This means that an additional meter or transmitter has to be installed between the PLC and the appropriate sensor. A discrete signal is often sent from a relay output on a meter to a discrete input on the PLC. Alternatively, an analog signal may be sent from the meter to an analog input on the PLC. Use of meters in addition to the PLC means additional expense, additional wiring, and additional programming since the meter will have to be programmed for alarm set points and alarm deadband. In summary, current PLCs are used primarily for control. They tend to be difficult if not impossible to use for calculating, manipulating, displaying or storing data. They cannot be used to obtain input directly from most water treatment sensors.

In conventional monitoring systems, it is common to have a number of separate meters monitoring the analytical parameters listed above. Each of these meters may then produce an analog output, which is recorded by some type of control device, such as a PLC. Many PLCs are designed having interchangeable input/output modules. These modules plug into a "rack" or a piece of hardware with multiple connections to some type of data bus, much like the ISA slots in a personal computer. However, in the case of analytical parameters such as pH, oxidation reduction potential (ORP), conductivity, dissolved oxygen, turbidity, corrosion rate, specific ion, etc., conventional systems monitor these parameters with separate discrete instruments. These instruments then send a signal, usually some type of analog signal, to a standard input module on the PLC. Presently available systems do not have input/output modules for analytical parameters available for standard PLCs.

With a conventional PLC, the monitoring and control system is configured by selecting the assorted meters necessary to monitor the parameters of interest. These are hardwired to the PLC and both the PLC and the meters have to be programmed. In the case of the present invention, configuration is done via software rather than hardwiring, and input/output modules are used to monitor and control analytical parameters as well as other parameters. The present invention also allows the operator to log data as well as display data.

Patents which disclose devices designed to combine the different conductivity meters, pH meters, ORP meters, flow meters, etc. but unlike the present invention include U.S. Pat. No. 5,091,863, to Hungerford, et al., entitled *Automatic Fluid Sampling and Flow Measuring Apparatus and Method*, which discloses a device to monitor sewer flows and which is to be mounted inside a manhole. U.S. Pat. No. 5,172,332, to Hungerford, et al., entitled *Automatic Fluid Sampling and Monitoring Apparatus and Method*, is essentially the same device as that in U.S. Pat. No. 5,091,863 but includes broader program storage memory and data storage memory. U.S. Pat. No. 5,299,141, to Hungerford, et al., entitled *Automatic Fluid Monitoring and Sampling Apparatus and Method*, again discloses the same device as in the prior two patents but includes a photoelectric type sensor. U.S. Pat. No. 5,633,809, to Wissenbach, et al., entitled *Multi-Function Flow Monitoring Apparatus with Area Velocity Sensor Capability*, again discloses a similar device to the prior three patents but includes input/output points. However, these are fixed. Additional analog inputs and discrete outputs cannot be added. All of these devices are to be used in monitoring sewer pipes and are mounted in manholes, and their primary purpose is for flow measurement.

Unlike the aforementioned devices, the present invention is reprogrammable even after the unit has been installed. The present invention is designed to be programmed for each application, including logic control functions. It can be used for any type of fluid monitoring and control, not just wastewater. The aforementioned parameters can all be monitored directly from the sensor with the various input/output cards without any additional instrumentation. The input/output cards are interchangeable and selectable by the operator and can be interfaced directly to the data bus from the various instruments. The applications for this type of input/output card configuration are endless. Analytical process parameters have not been directly monitored by devices in the prior art. Because it is compact and flexible, the present invention can be mounted on a control panel with standard bracketing. This unique apparatus can be used to monitor streams in industrial settings as well as in the field.

Reverse osmosis (RO) is a simple process wherein water is forced through a membrane under pressure. The membrane rejects both dissolved and suspended solids thus producing a very pure permeate. The process may be described as filtration on a molecular or ionic level. Unlike most filtration processes, however, RO is not simple to monitor. In order to determine whether an RO unit is operating properly, a number of parameters must be recorded such as those listed in Table 1. FIG. 24 is a diagram demonstrating typical RO monitoring points in an RO system. Feed water enters through inlet 500 and is fed through RO membranes within an array of vessels shown generally at 508 and 510. Feed pressure is measured at header 504 and reject pressure at 506. Water exits through outlet 502.

TABLE 1

Raw Data Collected During RO Operation

| | |
|---|---|
| Feed Pressure | Reject Flow |
| Interstage Pressure | Permeate Flow |
| Reject Pressure | Feed Temperature |
| Permeate Pressure | Feed Conductivity |
| Feed Flow | Permeate Conductivity |

After recording the raw data listed above, yet another set of calculated values must be prepared using the raw data collected from the RO, as shown in Table 2. It is only from these calculated values that a determination can be made regarding the performance of the RO unit.

TABLE 2

Parameters Calculated from Raw Data

| | |
|---|---|
| First Stage Differential Pressure | Permeate Concentration |
| Second Stage Differential Pressure | Salt Rejection |
| Percent Recovery | Normalized Permeate Flow |
| Feed Concentration | |

The following is a closer examination of how each of these parameters is calculated and used to monitor RO performance.

Differential Pressures

As the feed water passes through the pressure vessels of an RO unit, it encounters resistance due to the feed spacers in the membrane elements. Therefore, even new elements present some resistance to flow as the water passes through the system. As the membrane elements experience use, foulants build up on the surface of the membrane and in the feed spacer material itself. As these foulants accumulate, the resistance to flow of the feed water increases. This resistance to flow may be measured as a differential pressure across the vessel.

Differential pressures are calculated using the following equation:

$$DP = P_f - P_r$$

Where:
DP=Differential Pressure
$P_f$=Feed Pressure (Vessel Inlet)
$P_r$=Reject Pressure (Vessel Outlet)

In most RO systems there is more than one vessel in the array. Since the vessels are all piped into a single header on both the inlet and outlet, these pressures are monitored on the header resulting in one feed pressure and one reject pressure per array.

Many RO systems also have more than one array or stage. In this case, pressure must be monitored at three or more locations and the differential pressures are calculated as follows:

$$DP_1 = P_f - P_i$$

$$DP_2 = P_i - P_r$$

Where:
$DP_1$=Differential Pressure Across the First Stage
$DP_2$=Differential Pressure Across the Second Stage
$P_f$=Feed Pressure (Vessel Inlet)
$P_i$=Interstage Pressure (Between Vessels)
$P_r$=Reject Pressure (Vessel Outlet)

As in the case of most RO parameters, it is important to monitor the change in differential pressure over time. As foulants build up on the membrane surface and in the channels of the feed spacer, the differential pressure will increase. It is important to act promptly if the differential pressure begins to increase. If the differential pressure is allowed to increase excessively, structural damage to the membrane elements is likely to occur. It is also more difficult to clean the membrane elements if they have acquired a high differential pressure since differential pressure restricts flow. The cleaning solution will have to flow through the same restricted feed channels as the feed water.

In multi-stage systems it is advantageous to observe the change in differential pressure relative to the stage. If the first stage shows a high differential pressure relative to the second stage, it may mean that the fouling is due to suspended solids being caught in the front end of the flow path. If the second stage shows a high differential pressure relative to the first stage, it may be an indication of scaling taking place in the second stage.

Recovery

Recovery refers to the amount of permeate being produced by the RO relative to the amount of feed water. It is calculated with the following equation:

$$\%R = (F_p/F_f) \times 100\%$$

Where:
%R=Percent Recovery
$F_p$=Permeate Flow
$F_f$=Feed Flow

The following example demonstrates the importance of recovery. If an RO unit is operating at 75% recovery, 25% of the original feed water volume is being rejected. This means that most, if not all, of the foulants in the feed water are now contained in only 25% of the volume that contained them when they entered the RO. In other words, they have been concentrated four times. Suppose the recovery is increased to 80%. While this may seem like a rather insignificant increase of only 5%, now only 20% of the original feed water volume is being rejected. The foulants that were in the feed water have now been concentrated five times. If the recovery had been increased to 90%, the foulants would have been concentrated ten times. Recoveries should be monitored closely. Even brief periods of high recovery can have detrimental effects on the cleanliness of the membrane.

Concentration

While concentration can be read directly via conductivity meters, it can also be calculated. Conductivity is a physical characteristic; i.e. the ability of the water to conduct an electric current. Concentration is a chemical characteristic referring to the amount of solids chemically dissolved in the water. If the solids dissolved in the water are ionic, concentration can be correlated to conductivity. This is due to the fact that the dissolved ions are the means by which the current (electrons) flows through the water. Fortunately, in most naturally occurring waters, the vast majority of the dissolved solids are in the form of ions. On the downside, the exact correlation between conductivity and concentration depends upon the type of ions present.

For example, if the water contains monovalent ions such as sodium, chloride, hydrogen, hydroxide, etc., the concentration (in mg/l) will be approximately one half of the conductivity (in micro Siemens). This relationship is often referred to as a conversion factor and is used as follows:

Concentration (in mg/l)=Conductivity (in uS)×Conversion Factor

In waters containing predominantly multivalent ions such as calcium, magnesium, sulfate, carbonate, etc., the conversion factor may be as high as 0.85. Since most waters contain a mixture of monovalent and multivalent ions, a common conversion factor is 0.67. Most conductivity meters which give results in mg/l (concentration) simply multiply the conductivity by this 0.67 conversion factor.

Salt Rejection

Salt rejection refers to the ability of the membrane to reject the dissolved solids (salts) in the feed water. There are a number of ways to calculate salt rejection. One of the most popular is the feed-reject average method. This is calculated as follows:

$$\%SR = 100 - ((C_p/((C_f + C_r)/2)) \times 100\%)$$

Where:

%SR=Percent Salt Rejection $C_p$=Concentration of Dissolved Solids in Permeate $C_f$=Concentration of Dissolved Solids in Feed Water $C_r$=Concentration of Dissolved Solids in Reject Salt rejection is important since it describes the quality of the water being produced by the RO unit. Even more important, a change in salt rejection may mean a change in membrane condition. It can indicate fouling, scaling, or chemical attack. It may also indicate a mechanical failure such as a leaking O-ring. Sudden changes in salt rejection are most often due to mechanical problems. Gradual changes are usually due to changes in membrane condition. For this reason, salt rejection must be monitored closely.

Normalized Permeate Flow

Many RO operators mistakenly use actual permeate flow to indicate RO performance. While this may be effective in some cases, it is usually not a good way to monitor RO performance. Actual permeate flow from a given RO unit is a function of three different variables: net drive pressure, water temperature, and membrane condition. Membrane condition, is the single variable that describes RO performance. A change in membrane condition would indicate such things as fouling, scaling, and chemical attack.

If the first two variables were to stay constant, a decline in actual permeate flow would indicate a change in membrane condition. Unfortunately, this is seldom the case. The other variables can change. When they do, a change in actual permeate flow may no longer mean a change in RO performance. Even worse, RO performance may be changing (i.e., membrane fouling or damage may be occurring) although no change in actual permeate flow is seen.

Calculating normalized permeate flow simply means that any changes that occur in the first two variables must be taken into consideration. If changes in net drive pressure and water temperature are accounted for by calculating normalized permeate flow and a change in permeate flow still occurs, then this change has to be due to the third variable, membrane condition. In other words, a change in membrane condition is taking place, which usually means the membrane must be cleaned.

The following is a closer examination of the first two variables which affect permeate flow, net drive pressure and water temperature.

Net Drive Pressure

Net Drive Pressure (NDP) refers to the summation of four different pressures acting upon the RO membrane during operation of an RO unit. FIG. 25 shows the forces acting upon an RO membrane. Two of these pressures are positive and two are negative. Applied pressure is the largest of the two positive pressures making up NDP. Applied pressure is created by the high pressure pump supplying feed water to the RO membrane. Without applied pressure, reverse osmosis is not possible.

Permeate osmotic pressure is the second of the two positive pressures making up NDP. Since the permeate is very low in dissolved solids, the osmotic pressure of the permeate is very low. For this reason, it is often left out of the NDP calculation. Osmotic pressure of the feed water is usually the largest of the two negative components of the NDP. It is a function of the amount of dissolved solids in the feed water and may be approximated by the following equation:

Osmotic Pressure (psi)=Total Dissolved Solids (mg/l)/100

Actual permeate pressure is the second of the two negative components of NDP. Actual permeate pressure is the back pressure placed upon the permeate during RO operation. It is usually a result of back pressure placed upon the permeate by a control valve or hydrostatic pressure from an overhead permeate tank. In some cases, there may be no permeate pressure.

The NDP is calculated with the following equation:

$$NDP = P_a + P_{op} - P_{of} - P_p$$

Where:

$P_a$=Applied Pressure $P_{op}$=Osmotic Pressure of Permeate $P_{of}$=Osmotic Pressure of Feed Water $P_p$=Permeate Pressure Since the osmotic pressure of the permeate is usually very low, it is often left out of the NDP equation resulting in:

$$NDP = P_a - P_{of} - P_p$$

There are an infinite number of NDPs in the RO system from feed water inlet to reject outlet. This is due to the fact that the applied pressure decreases as the feed water progresses from the inlet to the outlet. This pressure decrease results from the pressure drop across the feedspacer as the water flows through the membrane elements.

Likewise, the osmotic pressure of the feed water increases as the water flows from the feed water inlet to the reject outlet. This is due to the increase in feed water total dissolved solids (TDS) as permeate passes through membrane. Since these pressures change from the feed water inlet to the reject outlet, it is necessary to take the average of the applied pressure and the feed water osmotic pressure across the RO unit. Using these average values in the NDP equation results in the average net drive pressure. It is this average NDP which is used in the calculation of normalized permeate flow.

Water Temperature

Water temperature has an effect on the amount of water which is permeated through a given amount of membrane under a given net drive pressure. As water temperature drops, water becomes slightly more viscous and more difficult to force through the membrane. Likewise, as the temperature increases, water is more easily forced through the membrane. These changes in permeate flow due to temperature changes in the feed water do not indicate problems with the membrane. They do, however, need to be taken into consideration when calculating normalized permeate flow. This is done by using a temperature correction factor (TCF). These factors are determined experimentally by the membrane manufacturer and are used in the normalized permeate flow calculation to account for changes in permeate flow due to changes in temperature. Some typical temperature correction factors are listed below in Table 3. Each type of membrane will have a different set of temperature correction factors.

TABLE 3

Typical Temperature Correction Factors

| Temperature | Correction Factor | Temperature | Correction Factor |
|---|---|---|---|
| 20 | 1.220 | 25 | 1.000 |
| 21 | 1.172 | 26 | 0.962 |
| 22 | 1.126 | 27 | 0.925 |
| 23 | 1.082 | 28 | 0.890 |
| 24 | 1.040 | | |

Calculating Normalized Permeate Flow

Normalized permeate flow may be calculated by means of the following equation:

$$NPF = (NDP_s/NDP_a) \times TCF \times F_P$$

Where:
- $NDP_s$=Net Drive Pressure at standard conditions (start up conditions are often used as standard conditions)
- $NDP_a$=Net Drive Pressure at Actual Conditions
- TCF=Temperature Correction Factor for Actual Temperature
- $F_P$=Actual Permeate Flow The following is an example of an NPF calculation using the information listed below in Table 4. In this example, start up data is used as the standard.

TABLE 4

RO Operating Data

| | Start Up | Today |
|---|---|---|
| Date | 01/01 | 08/01 |
| Feed Water Temperature | 21 Deg C. | 29 Deg C. |
| Temperature Correction Factor | 1.172 | 0.857 |
| Average Applied Pressure | 195 psi | 205 psi |
| Average Feed Osmotic Pressure | 50 psi | 45 psi |

TABLE 4-continued

RO Operating Data

| | Start Up | Today |
|---|---|---|
| Permeate Pressure | 15 psi | 15 psi |
| Actual Permeate Flow | 25 gpm | 25 gpm |

The first step is calculating NPF at start up. The NDP must be calculated first.

$NDP_s = P_a - P_{of} - P_P$
$NDP_s = 195$ psi$-50$ psi$-15$ psi
$NDP_s = 130$ psi Next, the NPF equation. *Since this is the NPF at start up, both NDPs in this equation are the same:

$NPF_s = (NDP_s/NDP_a) \times TCF \times FP$
$NPF_s = (130$ psi$/130$ psi*$) \times 1.172 \times 25$ gpm
NPFs=29 gpm Next, the actual (today's) NPF is calculated. First, the actual NDP:

$NDP_a = P_a - P_{of} - P_P$
$NDP_a = 205$ psi$-45$ psi$-15$ psi
$NDP_a = 145$ psi The NPF equation:

$NPF_a = (NDP_s/NDP_a) \times TCF \times FP$
$NPF_a = (130$ psi$/145$ psi$) \times 0.857 \times 25$ gpm
$NPF_a = 19$ gpm The results show that there is a vast difference between the two NPF values, 29 gpm versus 19 gpm. This indicates that the membrane condition has changed over the first few months of operation. If the RO operator had been using the actual permeate flow rate as an indicator of performance, this change in membrane condition would not have been noticed. However, by normalizing the permeate flow, the changes that occurred over the months in NDP and water temperature were accounted for. By comparing the two normalized permeate flows, the change in membrane condition can be clearly identified.

This example revealed a dramatic change in membrane condition that occurred over several months. From this example, it should be obvious that normalized permeate flow should be calculated more often than every few months. Had the NPF in this example been calculated more frequently, possibly once per day, a gradual downward trend in NPF would have been noticed. It is this gradual downward trend in NPF that indicates the onset of membrane fouling or scaling. If remedies are not taken, the rate of NPF decline becomes greater. If the NPF drops too far, irreparable membrane damage will likely be the result.

A reference point is needed in order to measure the decline in NPF. This reference point is the amount of permeate flow expected from the NDP and temperature to which the permeate flow is being normalized (usually start up or standard conditions). If modern thin film composite membranes are being used, the expected permeate flow does not change very significantly from that experienced within a few days after start up. Normalizing to these start up conditions and comparing NPF to the start up NPF is an acceptable way of monitoring most RO systems using thin film composite membrane. Cellulose acetate (CA) membrane poses a slightly different situation. CA membrane exhibits a normal flux decline over time due to membrane compaction. When normalizing permeate flow from CA membrane it may be necessary to take this normal flux decline into effect.

As the condition of the membrane declines, the NPF drops below the curve showing the expected permeate flow. When the NPF drops to approximately 15% below that expected, the membrane should be cleaned and NPF should increase to match the expected permeate flow.

Problems With RO Monitoring

Monitoring RO performance is not difficult but is time-consuming and tedious. A great number of RO failures can be attributed to poor monitoring. There are generally three reasons why an RO unit is not monitored properly. The failure to record raw data is probably the most common problem in RO monitoring, especially in the case of smaller RO systems. Manually recording raw data by writing it down on log sheets is a time-consuming process. Many small RO systems may only be manned a portion of the time thus allowing even less time for data recording. Many RO systems have inadequate or inoperable instrumentation. This may result in missing or inaccurate data points even when the data is recorded.

Failure to analyze raw data is another problem. Raw data does little good in determining the operating status of an RO unit without at least some data analysis. Unfortunately, data analysis is also a time-consuming process since calculations must be made. There are a number of computer programs which make it easier to examine and analyze RO data but in most cases the raw data still has to be entered into a computer. Many times the raw data does not get analyzed until membrane damage occurs. This will often identify the cause of the problem. However, had the data been analyzed in real time, it is likely that the problem could have been corrected before the damage occurred.

Failure to respond after data analysis may be most detrimental to RO operation. Failure to respond to the information provided by on-going data analysis can happen for a number of reasons. The person conducting the analysis may not be trained to identify the trends indicating a problem. It may also be a result of poor communication. This may be the case when data analysis is done in a central location and the results of the analysis have to be communicated back to field personnel.

In summary, the ability to monitor an RO unit is dependent upon the availability of raw operating data. If raw data is not recorded, it will not be normalized, trended, and used to monitor RO performance. Manual record-keeping can be a time-consuming and tedious process, especially if multiple RO units are involved. The use of computerized data acquisition equipment in RO applications can assure that raw data is recorded in an accurate and timely manner. Although the gathering and recording of raw data does not guarantee that the data will be analyzed, it is the first step toward proper RO monitoring.

Prior Art RO Monitoring Systems

A conventional prior art RO monitoring system consists of a group of individual instruments, gauges, and meters to display the primary parameters necessary for RO monitoring. In addition to these instruments, the RO unit is usually equipped with a "wet panel". This is a separate panel holding pressure gauges and flow gauges, i.e., rotameters. The indicators in the wet panel must be physically connected by piping to the water being treated by the RO unit.

Typically the instruments making up a conventional RO monitoring system only monitor one parameter. This means that a relatively large number of instruments are needed and that each instrument must be programmed and calibrated separately. This can lead to some confusion if a number of instruments from different manufacturers are being used on the same system. Operating and calibration methods vary from manufacturer to manufacturer. On some of the prior art microprocessor-based instruments the menu structure can be quite involved since only a few keys are available to perform a multitude of functions.

FIG. 26 is a diagram of a typical prior art RO monitoring and control system using PLC 414 for logic control of the water treatment equipment via pumps, valves and switches at 522. (See also FIG. 12 discussed below.) Signals from instrumentation shown generally at 532 coming from conductivity 526, flow 528, and pressure, or other analog inputs, 524 must be hardwired as shown generally at 530 to PLC 414. The operator interface consists of panel-mounted indicator lights and switches 520.

In most applications, data provided by the prior art monitoring systems must be transcribed by hand from the display of the instrument to some type of log sheet. In rare occasions, analog outputs from the panel-mounted instruments may be routed to a data acquisition system or strip chart recorder. If the latter is used, data must still be manually transcribed at some point. Real-time response to instrument output is commonly available in the form of relay outputs for various discrete alarm set-points. The relay outputs are commonly used to illuminate indicator lights or signal a programmable logic controller (PLC) of an alarm condition. Since only the primary RO operating parameters are being monitored by the instruments, the alarms are based only on the condition of these primary parameters. Calculated parameters remain a mystery until the data is logged and proper calculations are performed.

Illustrative of the prior art of reverse osmosis systems are U.S. Pat. No. 5,647,973, to Desaulniers, entitled *Reverse Osmosis Filtration System with Concentrate Recycling Controlled by Upstream Conductivity*, U.S. Pat. No. 5,646,863, to Morton, entitled *Method and Apparatus for Detecting and Classifying Contaminants in Water*; U.S. Pat. No. 5,422,014, to Allen et al., entitled *Automatic Chemical Monitor and Control System*; U.S. Pat. No. 4,849,098, to Wilcock et al., entitled *Continuous Water Quality Monitor*; U.S. Pat. No. 4,587,518, to King, entitled *Monitor and Control System for Water Purification Apparatus*; and U.S. Pat. No. 4,498,982, to Skinner, entitled *Reverse Osmosis Water Purification System*. Illustrative of the prior art relating to pressure sensing manifolds are U.S. Pat. No. 5,967,167, to Johnson, entitled *Remote Controlled Drinker System*; U.S. Pat. No. 5,852,563, to Weber et al., entitled *Intelligent Coolant Flow Control System*; U.S. Pat. No. 5,808,909, to Rees, entitled *Electronic Brake Control Valve Tester for Rail Cars and Trains*; U.S. Pat. No. 5,566,717, to Robert, entitled *Assembly for Controlling Fluid Passing Through a Manifold*; U.S. Pat. No. 5,519,636, to Stoll et al., entitled *Electronic Control Device for a Valve Range of Modular Design*; U.S. Pat. No. 5,384,709, to Seder et al., entitled *Miniature Fluorescent Lamp Processing Apparatus*; U.S. Pat. No. 5,351,705, to Reinders et al., entitled *Method and Apparatus for Controlling Fluid Pumps and Valves to Regulate Fluid Pressure and to Eliminated Fluid Flow Surges*; U.S. Pat. No. 5,325,884, to Mirel et al., entitled *Compressed Air Control System*; U.S. Pat. No. 5,320,760, to Freund et al., entitled *Method of Determining Filter Pluggage by Measuring Pressures*; and U.S. Pat. No. Re. 29,383, to Gallatin et al., entitled *Digital Fluid Flow Rate Measurement for Control System*.

Summary of the Invention

DISCLOSURE OF THE INVENTION

The present invention is of a fluid monitoring and control apparatus and method comprising: providing a programmable and reprogrammable control unit comprising a display, user inputs, and input/output connectors; placing a programmable logic controller in direct communication with the control unit, which programmable logic controller is programmable and reprogrammable through the control unit; and placing a plurality of fluid parameter sensors in direct communication with the control unit. In the preferred embodiment, the control unit comprises a serial port for direct communication with the programmable logic controller and a network connection port for direct communication with the plurality of fluid parameter sensors. The programmable logic controller need have no inputs other than from the control unit. An integral housing is preferred to which the control unit and the plurality of sensors are attached and through which flows a fluid stream whose parameters are being sensed by the sensors. A pressure sensing manifold is employed cycling through a plurality of solenoid valves but requiring only a single input/output connection to the control unit.

The present invention is also of a fluid control apparatus and method comprising providing a membrane and estimating salt rejection by the membrane. In the preferred embodiment excessive changes in the salt rejection are detected. The estimating comprises detecting a concentration of dissolved solids in a permeate ($C_P$), in feed water ($C_F$), and in reject flow ($C_R$), preferably by calculating $C_P/((C_F+C_R)/2)$. The control apparatus and method can also calculate recovery, differential pressure (DP), and normalized permeate flow (NPF).

A primary object of the present invention is to provide the ability to directly receive analytical parameters.

Another object of the present invention is to monitor and control a variety of fluid treatment parameters with one integrated programmable apparatus.

Yet another object of the present invention is to monitor and control fluid treatment parameters from a central location mounted on a single control panel.

Still another object of the present invention is to provide an integrated apparatus for monitoring and controlling fluid treatment parameters that is easily programmed and simple to operate.

A primary advantage of the present invention is that individual meters and gauges are not necessary to monitor and control fluid treatment parameters.

Other objects, advantages and novel features, and further scope of applicability of the present invention will be set forth in part in the detailed description to follow, taking in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 29 is a bottom-side view of the second embodiment of the apparatus of the present invention showing serial ports and modem connection;

FIGS. 30a–b are rear and side views of the second embodiment of the apparatus of the present invention showing terminal blocks for sensor and power inputs to the apparatus;

FIG. 38 is a diagram demonstrating the second embodiment of the present invention in communication with a network and a PLC.

DESCRIPTION OF THE PREFERRED EMBODIMENTS

Figure 1:
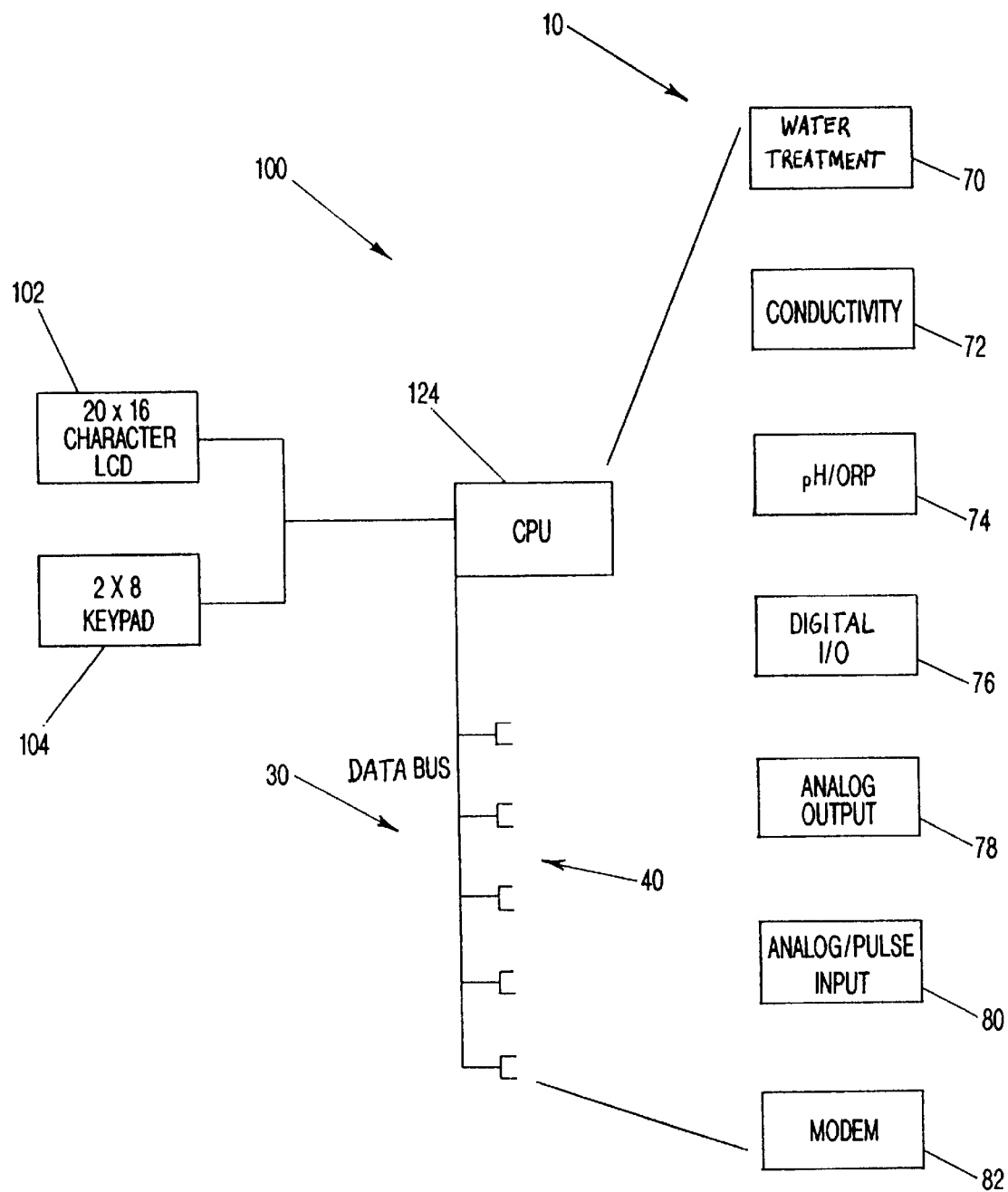
FIG. 1 is a block diagram of a first embodiment of the present invention.

Best Modes for Carrying Out the Invention

The present invention is a programmable, integrated compact data acquisition, monitoring, and control system designed for fluid treatment applications. It is capable of monitoring a variety of inputs, for example pressure, conductivity, pH, ORP, temperature, and flow and is designed to replace the usual assortment of meters and gauges making up most fluid treatment monitoring systems. Since it is an integrated monitor, all of the operating parameters are examined by the same instrument. The apparatus can also calculate values such as differential pressure, flow recovery, energy consumption, chemical usage, total operating time, total volume processed, salt rejection, temperature differential, heat loss, and normalized data with the CPU. Alarm set points can be entered for both primary and calculated parameters and alarm events are logged to an internal alarm log. The present invention can also log operating data, transmit data via modem, or print data on an optional printer.

First Embodiment

In the first preferred embodiment, the fluid treatment apparatus is equipped with a serial port which may be configured as either RS-232 or RS-485. This allows the apparatus to communicate with a number of third-party devices such as personal computers, PLCs, printers, modems, and distributed control systems. The apparatus comes with appropriate software for downloading data via direct connection or modem. Preferably Windows 95 or comparable software is used. The apparatus is ideal for a number of fluid and water treatment applications, including cooling towers, boilers, reverse osmosis (RO) units, ion exchange units, reverse osmosis and ion exchange pretreatment systems, and wastewater treatment.

Passive backplane architecture provides versatility to the apparatus. The unit houses a central microprocessor connected to a passive backplane containing a number of expansion slots. These slots may be equipped with one or more of a variety of input/output cards available for specific types of input and output. By selecting the appropriate display/CPU unit along with the appropriate input/output card or cards, the end user can configure a monitoring system for a specific application. Many different input/output cards are available to choose from.

Example input/output cards include the following. A combination input card preferably receives inputs from two conductivity cells, two temperature sensors for conductivity temperature compensation, four flow sensors, and four auxiliary analog inputs from four to twenty milliamps. A conductivity input card preferably receives inputs from two conductivity cells and two temperature sensors for temperature compensation. A pH/ORP card preferably receives input from either two pH probes, two ORP probes, or a combination of the two. It also receives inputs from two temperature sensors for pH temperature compensation. The digital input/output card is preferably equipped with eight optically isolated digital inputs capable of receiving signals up to 48 volts AC or DC. It is also equipped with eight single pole single throw relays able to withstand three amperes at 120 volts. The analog/flow input card is a general purpose card capable of accepting eight four to twenty milliamp analog inputs (single-ended, non-isolated) and six flow inputs. The flow inputs are configured to accept open collector outputs from Hall effect type flow sensors. The analog output card is preferably equipped with four non-isolated, single-ended, analog four to twenty milliamp outputs. The parallel printer interface card allows the apparatus to print data to any printer equipped with a parallel interface. A serial communication card can also be programmed for specific communication protocols such as Modbus, DeviceNet, Profibus, and others. A temperature card is available for a thermocouple, RTD resistor, and thermistor. An individual pH card is also available. The apparatus also accommodates a conductivity and resistivity card. An individual ORP card can be used, as well as a dissolved oxygen card. A corrosion rate card is available and is accomplished by means of linear polarization resistance or other standard means. Turbidity and particle counting cards can also be placed into the apparatus. A modem card allows the apparatus to transmit data via modem when used in conjunction with data transfer software. These are just examples of the many different input/output cards available and comprise only one embodiment of each. Many alternative embodiments for each input/output card would be obvious to those skilled in the art.

Although many features and components can be used to configure the apparatus, the apparatus most preferably uses the following: a NEMA 12-panel mounted enclosure, a Phillips 80C552 microprocessor (22 megahertz), 128K SRAM with lithium backup, a 128K FLASH memory, a Dallas real time clock, an RS-232/RS-485 serial port, a 20 by 16 character LCD display with LED backlight, a 2 by 8 numeric keypad, a five amp and 120/240 volt to 24 volt transformer or 24 volt DC power supply, and software for system configuration and data transfer. Preferably, Windows-based software is used in the apparatus.

The software is used for two purposes. First, it provides a way in which the operator can configure the hardware of the apparatus for a specific application. The software also allows the operator to label individual inputs, establish ranges and alarm set points for each input, designate alarm relays for various parameters, and set analog output ranges for various parameters. Data transfer software is used for downloading data either by direct serial connection or remotely via modem. Data downloaded from the apparatus may be saved in an ASCII delimited format. This makes it possible to read the data with virtually any spreadsheet program. The apparatus also includes a PCMCIA interface in the preferred embodiment. This hardware allows the apparatus to download data to a standard PCMCIA memory card. Data saved to the card may then be uploaded to any personal computer.

In the preferred embodiment, the entire fluid treatment apparatus is approximately 5.25 inches wide, 5.25 inches high, and 6.25 inches deep. It weighs approximately three pounds. Power consumption for the apparatus is five amps at 24 volts AC or DC. The system can be equipped with a 120/240 volt transformer or 24 volt DC power supply.

The software configuration for the present invention is preferably a Windows-based package. The operator loads the software on a standard personal computer and starts designing the system by inputting the parameters to be monitored, including their names, units, scales, and so on. Next, any calculated values are included by typing in the appropriate formula. Alarms are then defined, including high and low set points and alarm deadbands. After the configuration is complete, the information is downloaded to the fluid treatment apparatus via a serial transfer cable. Then the apparatus is ready for use. Frequently changed parameters such as alarm set points and deadbands may be changed directly from the keypad. The central processing unit (CPU) of the apparatus is different from those commonly used in PLCs. The CPU in the fluid treatment apparatus is powerful and equipped with a large amount of memory. This allows the apparatus to store a large amount of data. The software allows the CPU to be programmed in BASIC programming language rather than ladder logic which is used by most PLCs. This means that the apparatus has the ability to easily calculate, store, and otherwise manipulate data.

A simple example of a logic statement might be as follows: "Start the feed pump if the selector switch is in the auto position and if the level switch is in the low position. Start the high pressure pump ten seconds after starting the feed pump." The BASIC source code used to perform this logic control would be as follows:

| | |
|---|---|
| 10 XIH 016: XIL 017: OTE 000 | REM starts feed pump |
| 11 XIH 000: DLY 000, 010: OTE 002 | REM delays start of HP pump |
| 12 GOTO 10 | |

These logic instructions are entered during the configuration procedure with the Windows configuration software. Unlike most PLCs, the fluid treatment apparatus serves as its own operator interface. Messages may be programmed into logic portion of the configuration to appear on the screen during operation. Also, the status of all input/output points may be viewed by selecting the appropriate screen from the fluid treatment apparatus main menu. Preset values for counters and timers may be changed directly from the keypad without having to connect to a laptop personal computer or handheld programming unit. Therefore configuration for the apparatus' monitoring and control is done via software rather than through hardwiring. This data can then be processed and stored and transmitted via modem or a serial connection. The entire operation occurs at the fluid treatment apparatus.

The fluid treatment apparatus may be programmed to do any calculations. This allows data to be calculated automatically and in real time, thus lowering manpower requirements and providing up-to-date information. A typical example is the calculation of normalized permeate flow from reverse osmosis units.

The apparatus also stores operating data to internal memory for later retrieval with any personal computer via serial port or modem, or stored to an optional memory card. The memory card may also be used for uploading the system configuration. Furthermore, the fluid treatment apparatus logs all alarm events, which may be viewed directly on the fluid treatment apparatus display. Discrete input/output status may be viewed on the display during operation to facilitate troubleshooting without having to connect a personal computer or handheld programming unit to the controller. The ability to program and display status messages eliminates the use of PLC operator interfaces. The modem input/output card allows communication to personal computers via standard telephone lines. A serial port allows networking via serial communication. As stated previously, the fluid treatment apparatus is capable of directly monitoring a number of fluid treatment analytical process parameters such as conductivity, pH, ORP, temperature, dissolved oxygen, turbidity, ion specific, and flow. It is also capable of monitoring virtually any other parameter via standard four to twenty milliamp analog signals or via discrete signals.

The apparatus is also capable of calculating additional data based upon raw process data. These values, along with raw data, may then be logged for future evaluation. The apparatus can also be used to control process conditions. This may be as simple as opening and closing relay contacts based upon alarm conditions or it may be more elaborate and involve logic control for a particular process. Each fluid treatment apparatus is programmed separately and for a particular application.

Raw operating data is logged into an internal memory location. The logging interval for the data is preferably once every 30 minutes. Due to the large volume of data acquired in the data log, the data is not viewable on the LCD of the apparatus. It can, however, be downloaded by connecting a personal computer to the serial port (either locally or via modem) with the software.

Operation of the apparatus is very simple because it is completely menu driven, with the only exception being sensor calibration. Upon power up, the apparatus will display a main menu from which the operator may choose from a number of screens by pressing the appropriate key on the keypad. Data screens allow the operator to observe real time operating data. A settings menu allows changes to parameters such as set points, deadbands, time delays, flow sensor K factors, and conductivity correction factors, analog ranges and scales, and time delays. An access code is entered in order to change settings. K factors must be entered for all flow sensors providing a pulse signal. The K factor is defined as the number of pulses produced by the flow sensor by every gallon that passes through the sensor. The alarm history screen allows the operator to view alarms logged by the fluid treatment apparatus. An output status screen allows the operator to view the status of output relays. The input screen allows the operator to view the status of discrete inputs and internal memory bits. These are just some of the screens and capabilities of the fluid treatment apparatus, all of which are controlled by BASIC software. All parameters are monitored and displayed by one panel-mounted apparatus. This means that a number of calculated values can be continuously monitored, recorded, and displayed, a feature important in monitoring and controlling water treatment systems. A Windows-based configuration application is provided as an alternative embodiment for the fluid treatment apparatus in place of the direct BASIC programming embodiment.

Attention is now turned to the figures. FIG. 1 shows a basic block diagram of a first embodiment of fluid treatment apparatus 100. Example input/output cards are shown generally at 10. The input/output cards can be water treatment combination card shown at 70, conductivity card 72, pH/ORP card 74, digital input/output card 76, analog output card 78, analog/pulse input card 80, and, modem card 82. CPU 124 communicates with input/output cards 10 via I/O card data bus 30. Bus connectors are shown generally at 40. CPU 124 communicates with a 20 by 16 character LCD display 102 and 2 by 8 keypad 104. Of course, these dimensions are variable, and FIG. 1 only shows a first preferred embodiment of the present invention.

Figure 2:
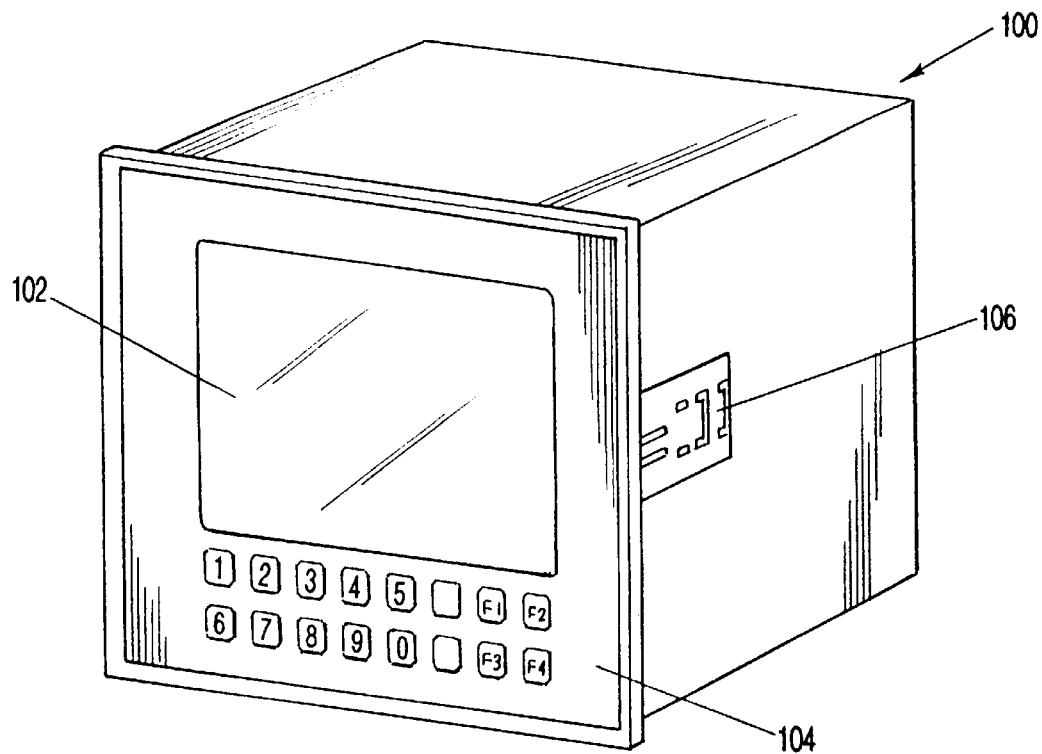
FIG. 2 is a perspective frontal view of the display module of the first embodiment of the apparatus of the present invention.

FIG. 2 is a perspective view of fluid treatment apparatus 100. Display 102 displays various parameters and directs the operator through various menus and operator input operations. Keypad 104 is used to program and operate the apparatus. Attachment points 106 allow clamps to be attached for panel mounting.

Figure 3:
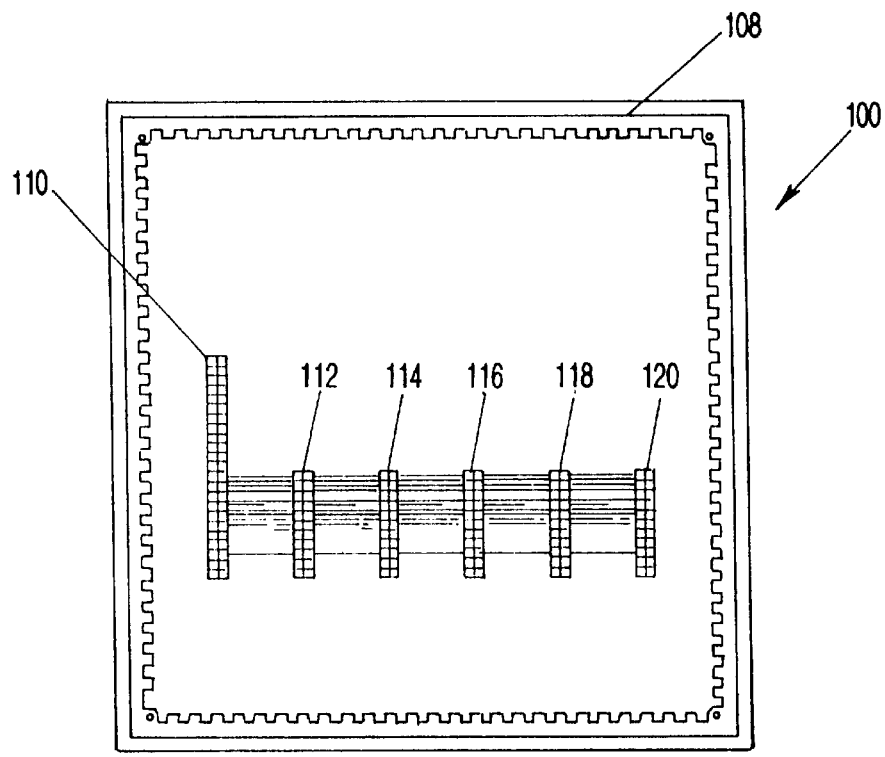
FIG. 3 is a rear view of the display module showing input/output connectors of the first embodiment of the present invention.

FIG. 3 shows a rear view of fluid treatment apparatus 100. The backplane in fluid treatment apparatus 100 is equipped with six ports which consist of CPU connector port 110, and input/output card connector ports 112, 114, 116, 118, and 120. CPU connector port 110 is always occupied by the CPU card. Card guides shown generally at 108 provide guides for sliding the CPU and various input/output cards into the rear of fluid treatment apparatus 100.

Figure 4:
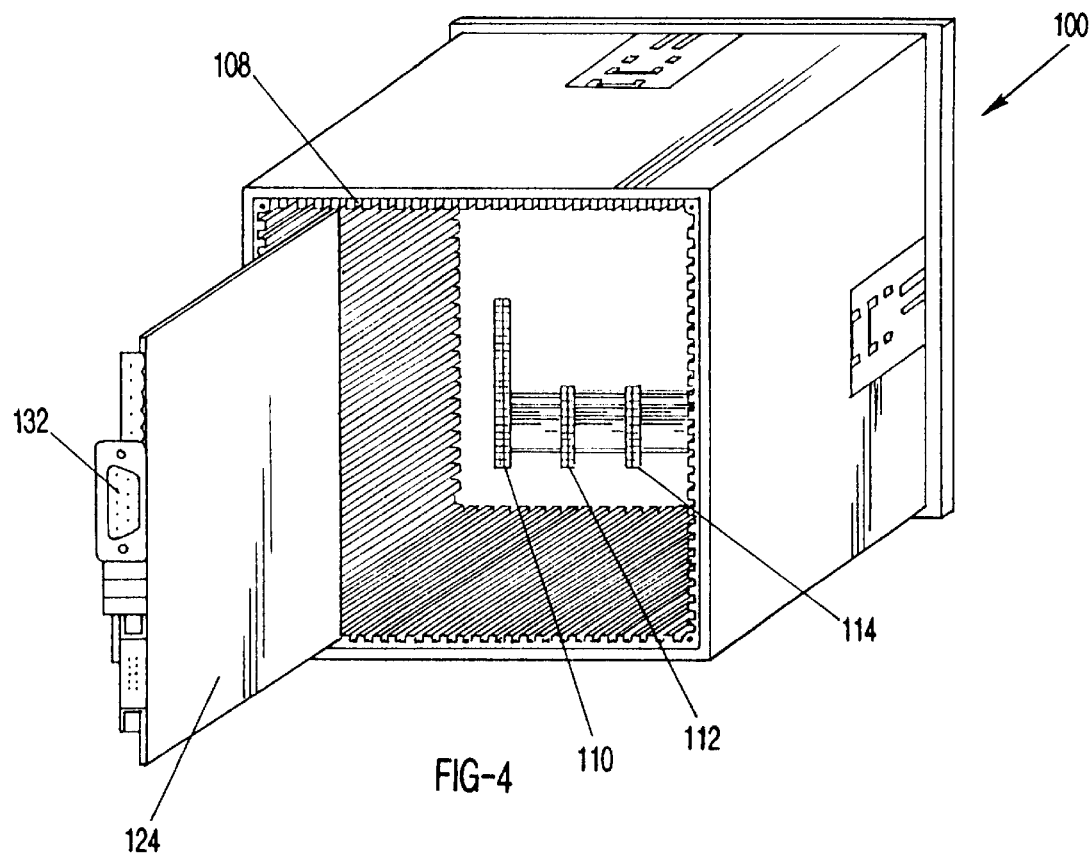
FIG. 4 is a perspective rear view showing the card guides of the first embodiment of the present invention.
Figure 5:
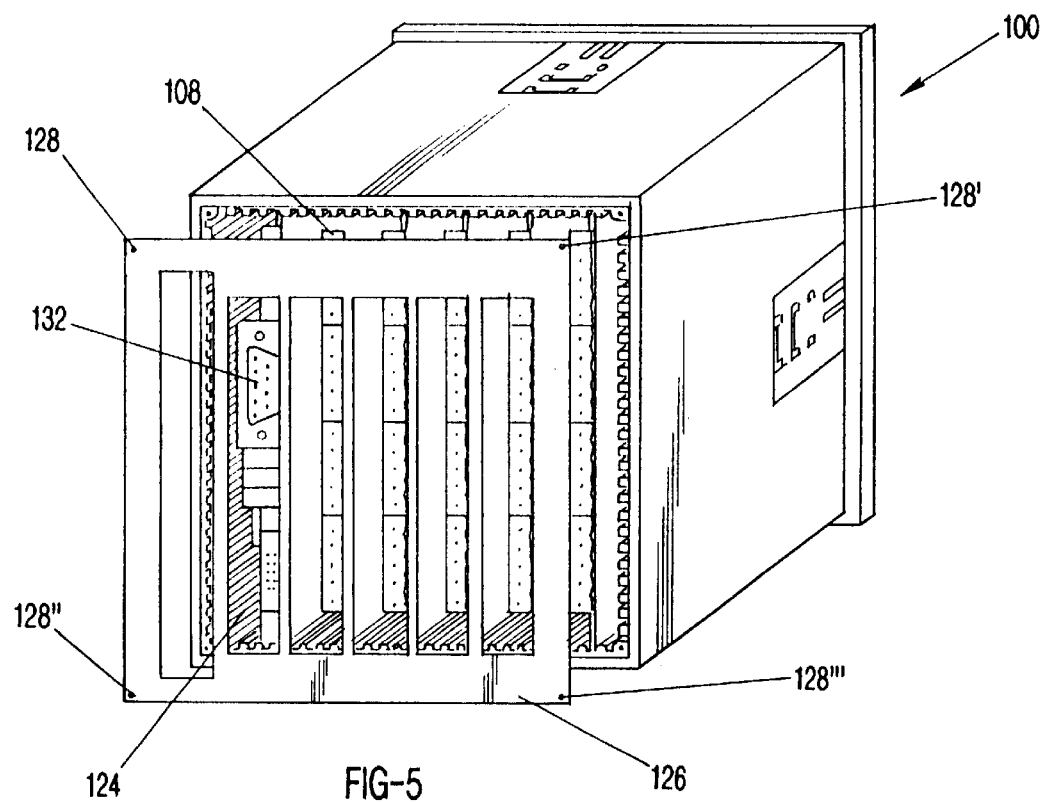
FIG. 5 is a perspective rear view of the display module and back plate of the of the first embodiment of the present invention.

FIG. 4 shows fluid treatment apparatus 100 and CPU card 124 as it is slid into the rear of fluid treatment apparatus 100 via one of card guides 108. Serial port 132 provides communication with external devices. As shown in FIG. 5, once the CPU and selected input/output cards are placed in the rear of fluid treatment apparatus 100, back plate 126 is screwed via screws 130, 130', 130", and 130'" and screw holes 128, 128', 128", and 128'" onto the rear of fluid treatment apparatus 100.

Figure 6:
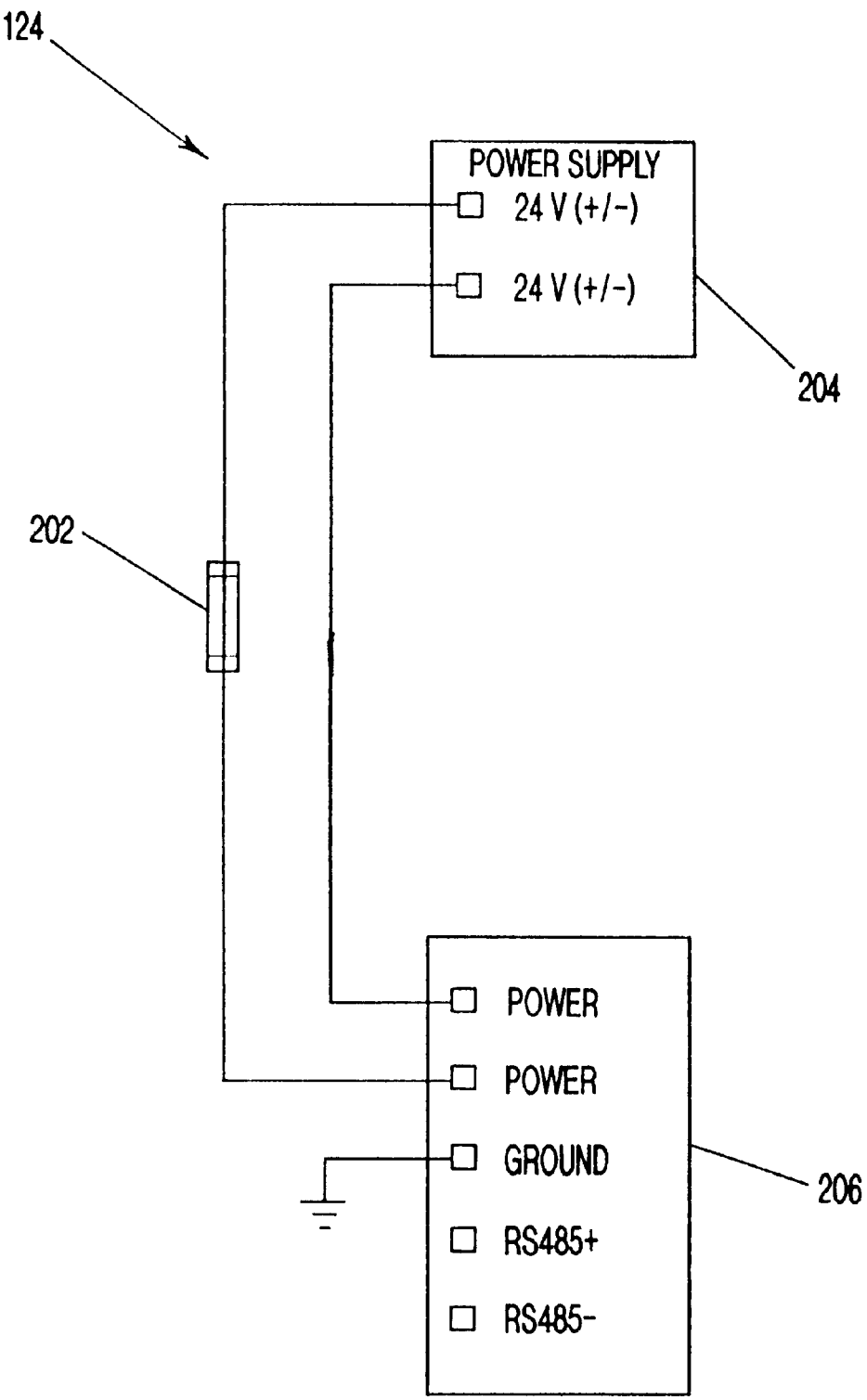
FIG. 6 is a schematic diagram of the terminal connections on the main central processing unit card of the first embodiment of the present invention.

FIG. 6 shows the terminal connections on the main CPU card 124 as a schematic block diagram. Power supply 204 provides either 24 volts AC or DC. The two power inputs are bipolar, i.e., positive power may be connected to either of the two terminals. Fuse 202 is used to protect the power connection to CPU card 124. Power, ground, and RS-485 connections are shown generally at 206. CPU card 124 should be properly grounded to earth ground. CPU card 124 serves several functions, including storing and executing the main control program, communicating with the input/output cards via the bus, communicating with external devices via serial port 132, receiving input from keypad 104, and sending output to display 102.

Figure 7:
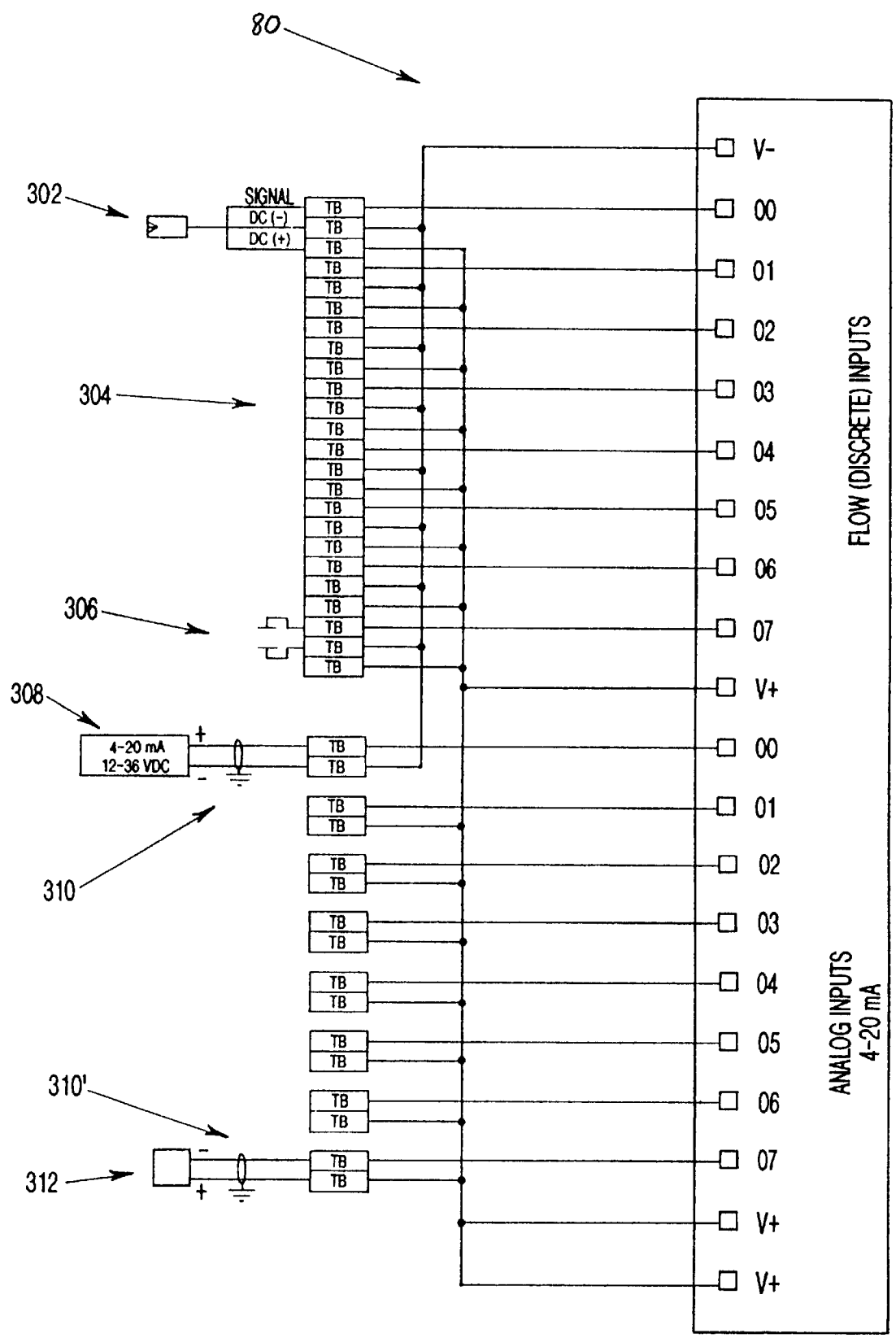
FIG. 7 is a schematic-block diagram of the terminal connections on the analog/flow input card of the first embodiment of the present invention.

Analog/flow input card 80 terminal connections are shown as a schematic block diagram in FIG. 7. This card is designed to be used with flow sensors equipped with an open collector, Hall effect output. The analog/flow input card is a general purpose card which allows fluid treatment apparatus 100 to receive input from other devices producing preferably a four to twenty milliamp signal. It also may be used to receive input from devices producing a sinking pulse by means of a Hall effect sensor. In the preferred embodiment of the invention, one fluid treatment apparatus 100 will support up to eight analog/flow input cards. The analog/flow input card has eight single-ended 12-bit inputs at four to twenty milliamps, and eight sinking pulse 12 to 24 volts DC. Power required for the analog/flow input card is either five volts DC or 24 volts DC via the bus connection. Twenty-four volts DC is supplied to two wire transmitters via terminal connectors. This card is programmed using either BASIC or Windows configuration software. Hall effect flow sensors have three lead connections 302, one for positive DC, one for negative DC, and one for the return signal for sinking pulse. Terminal blocks 304, for example, DIN rail style, should be used to connect terminals to field wiring. This allows smaller gauge wire to be used on the terminals. Flow inputs may also be used as discrete inputs 306, such as for hand switches and float switches. Input 306 is high when connected to the low side of the DC supply, sinking input. Some devices produce their own four to twenty milliamp signal without requiring power from fluid treatment apparatus 100. These devices may be used with the analog/flow input card and connected at 308. However, they must produce an isolated output of sufficient amperage. These devices are interfaced by connecting the positive output of the device to the analog input of the card. The negative side of the device is connected to the V-terminal of the card. Analog devices should be connected to fluid treatment apparatus 100 with shielded cable 310, 310'. The shield of the cable should be grounded but only at one end of the cable. Two wire analog transmitters at four to twenty milliamps may be powered by the 24 volt DC output 312 from the analog/flow input card. The positive side of the transmitter is connected to the V+ terminal of the card. The negative side of the transmitter is connected to the analog input.

Figure 8:
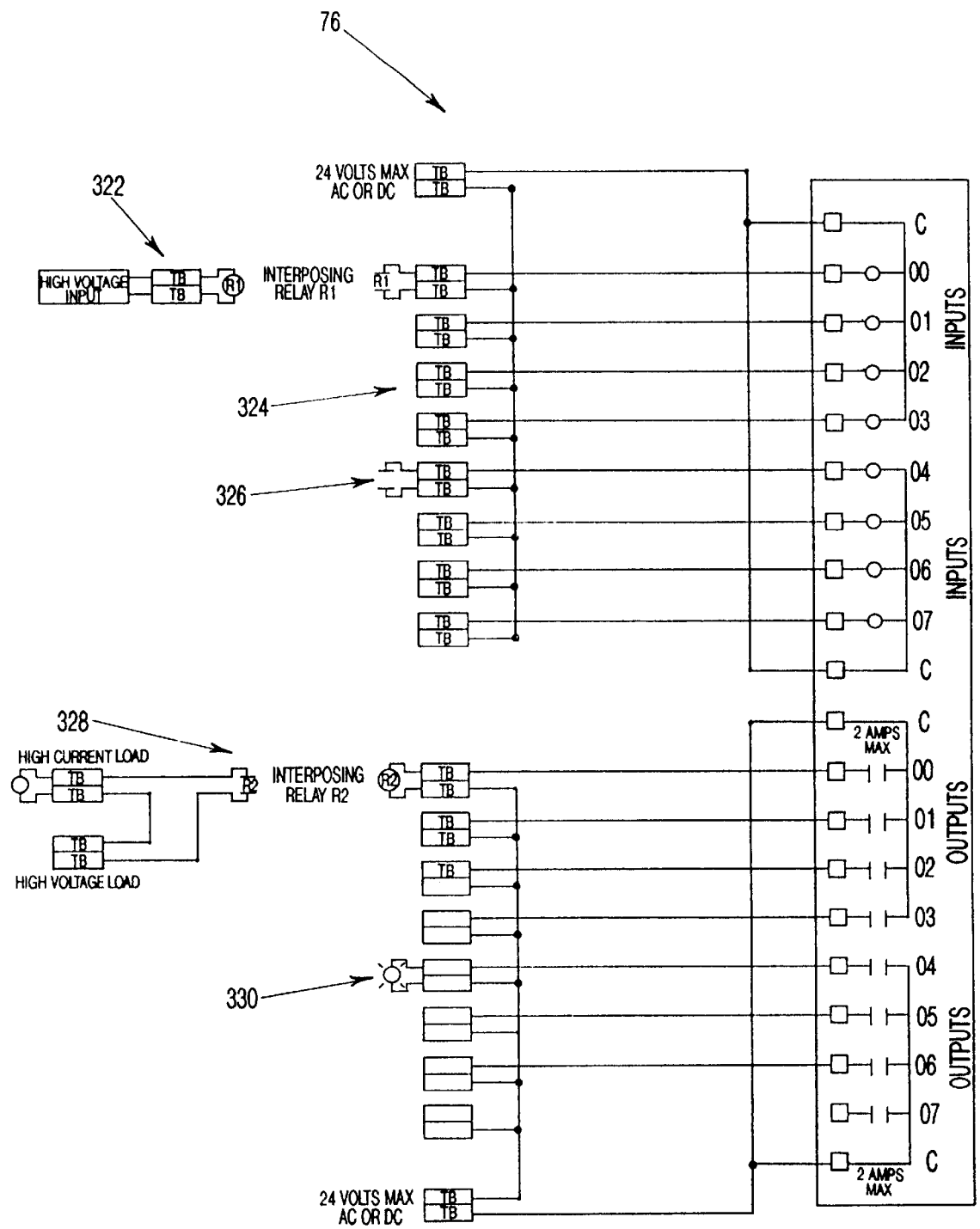
FIG. 8 is a schematic-block diagram of the terminal connections on the digital input/output card of the first embodiment of the present invention.

Digital input/output card 76 terminal connections are shown as a schematic block diagram in FIG. 8. Digital input/output card 76 is a general purpose card which allows fluid treatment apparatus 100 to receive discrete inputs from devices such as level switches, hand switches, float switches, push buttons, selector switches, pressure switches, and PLC relay outputs. It is also equipped with relay outputs to control pumps, motors, lights, valves, and other devices. In the first preferred embodiment of the invention, one fluid treatment apparatus 100 will support up to eight digital input/output cards. The digital input/output card has eight optically isolated inputs, two groups of four, with one common connection per group. Input voltage is limited to 24 volts AC or DC. The output of digital input/output card 76 is eight SPST (single pole single throw) relays in two groups of four, with one common connection per group. Switched voltage is limited to 24 volts AC or DC, with a maximum current of two amps per common connection. Relay contacts are protected with MOVs. Digital input/output card 76 requires five volts DC, 24 volts DC via the bus connection. Inputs with voltages greater than 24 volts AC or DC must be interfaced through an interposing relay 322 or isolator. Terminal blocks 324, for example, DIN rail style, should be used to connect terminals 324 to field wiring. This allows smaller gauge wire to be used on the terminals 324. Low voltage discrete inputs 326, less than 24 volts AC or DC, may be connected directly to the inputs. Applications that require switching of voltages greater than 24 volts AC or DC or switching of high loads, greater than two amps per output group, must use interposing relays 328. Low voltage, low load outputs may be switched directly by output relays 330. Relays 322, 328 and 330 enable fluid treatment apparatus 100 to control devices such as solenoid valves, motor starters, indicator lights, and alarms. It is apparent that, when properly programmed, fluid treatment apparatus 100 can replace PLCs in most water treatment applications.

Figure 9:
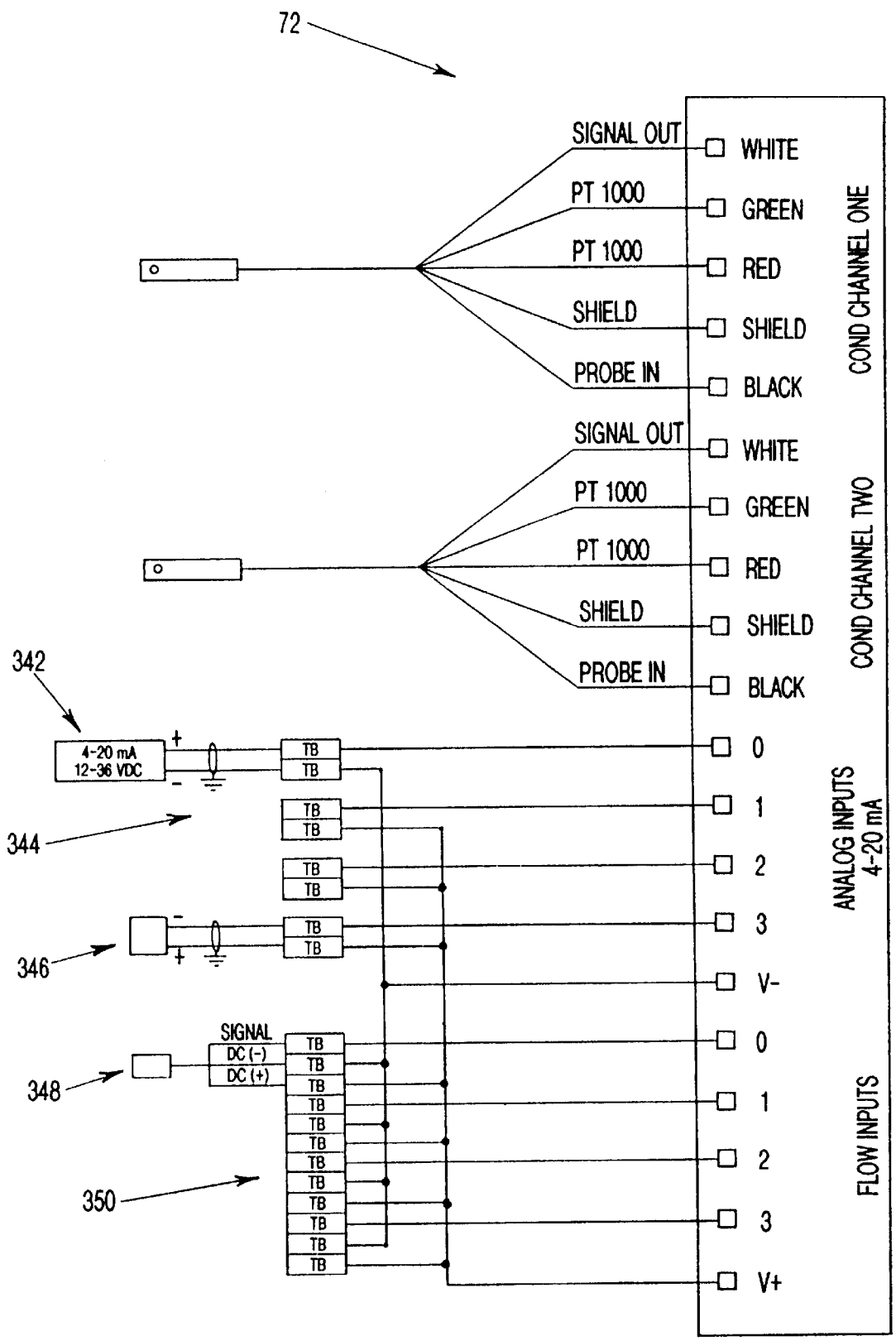
FIG. 9 is a schematic-block diagram of the terminal connections on the conductivity input card of the first embodiment of the present invention.

Conductivity input card 72 terminal connections are shown generally in FIG. 9 as a schematic block diagram. Conductivity input card 72 allows fluid treatment apparatus 100 to monitor two standard conductivity cells. The cells are equipped with 1,000 ohm platinum RTD resistors for temperature compensation in the preferred embodiment. It is also able to receive input from four other devices producing a four to twenty milliamp signal 342 and from three devices producing a sinking pulse by means of a Hall effect sensor. In the preferred embodiment, one fluid treatment apparatus 100 will support up to eight conductivity input cards 72 and contains two electrode conductivity cells inputs, two 1,000 ohm platinum RTD resistor sensors, four single-ended 12-bit inputs at four to twenty milliamps, and three sinking pulse inputs at 12 to 24 volts DC. Conductivity input card 72 requires five volts DC or 24 volts DC via the bus connection, and supplies 24 volts DC to two wire transmitters via terminal connectors. Shielded cable 344 is shown to connect analog devices to fluid treatment apparatus 100. Two wire analog transmitters, four to twenty milliamps, may be powered by the 24 volt DC output 346 from conductivity input card 72. Hall effect flow sensors have three lead connections 348, one for DC+, one for DC−, and one for the return signal, sinking pulse. Terminal blocks 350, for example, DIN rail style, should be used to connect the fluid treatment apparatus terminals to field wiring. This allows smaller gauge wire to be used on the terminals. Proper ranges for each conductivity channel are set by dip switches on the card.

Figure 10:
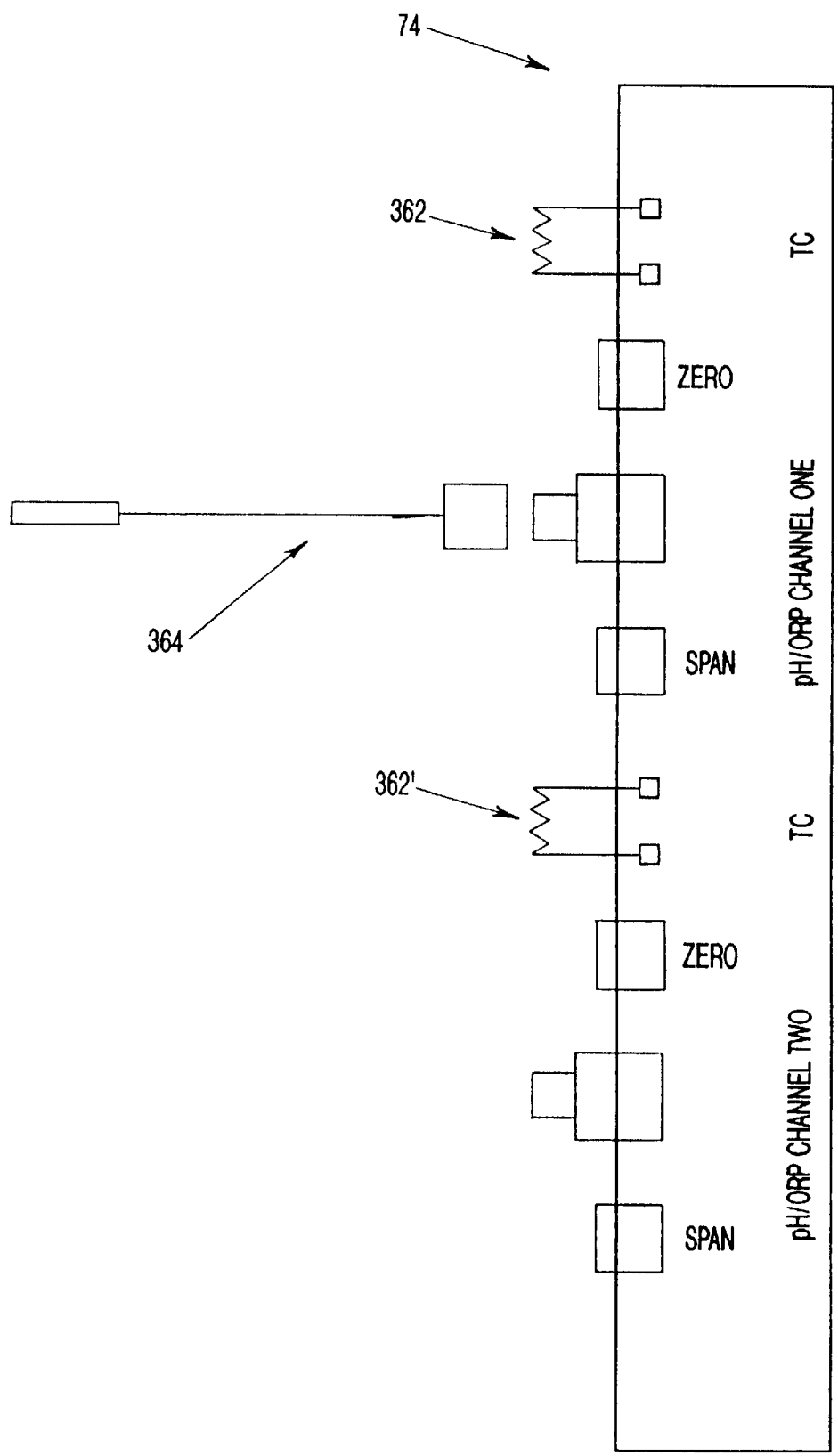
FIG. 10 is a schematic-block diagram of the terminal connections on the pH/ORP input card of the first embodiment of the present invention.

PH/ORP input card 74 terminal connections are shown generally in FIG. 10 as a schematic block diagram. PH/ORP input card 74 allows fluid treatment apparatus 100 to monitor two standard pH electrodes, two ORP electrodes, or a combination of the two in the preferred embodiment. PH probes are equipped with 1,000 ohm platinum RTD resistors 362, 362' if temperature compensation is required. In the preferred embodiment, one fluid treatment apparatus 100 will support up to eight pH/ORP input cards 74. Low impedance coaxial cable 364 should be used to connect pH and ORP probes directly to pH/ORP card 74. The input for pH/ORP card 74 is two high impedance analog voltage inputs at plus or minus 1,000 millivolts for pH or ORP electrodes, and two 1,000 ohm platinum RTD resistor temperature sensors. PH/ORP input card 74 is powered by five volts DC or 24 volts DC via the bus connection.

Figure 11:
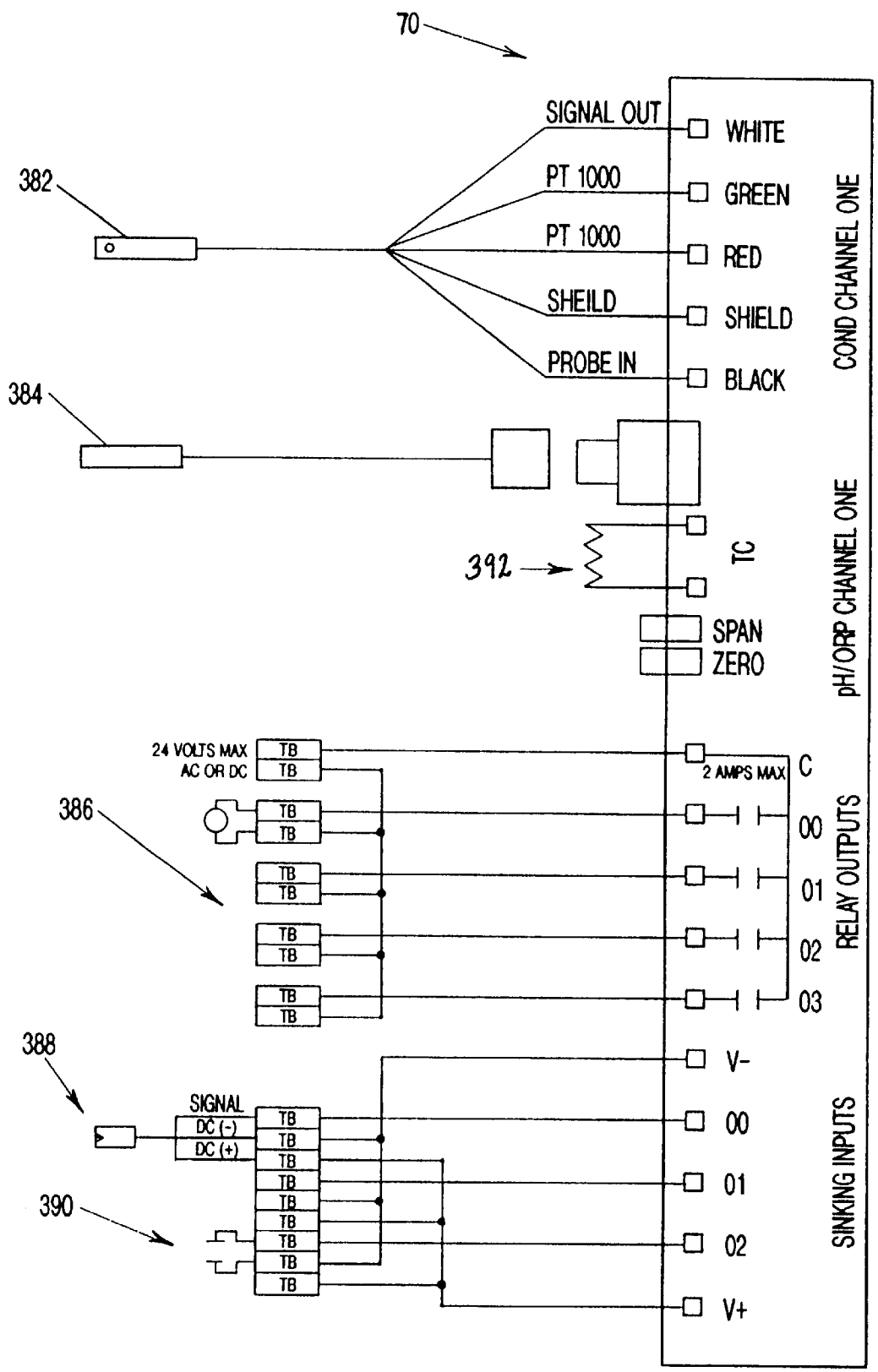
FIG. 11 is a schematic-block diagram of the terminal connections on the water treatment and reverse osmosis combination input card of the first embodiment of the present invention.

Water treatment and RO combination input card 70 terminal connections are shown as a schematic block diagram in FIG. 11. Water treatment combination card 70 allows fluid treatment apparatus 100 to monitor one standard conductivity cell, one pH or ORP electrode, and three sinking pulse discrete inputs in the preferred embodiment. Conductivity and pH sensors are equipped with 1,000 ohm platinum RTD resistors for temperature compensation in the preferred embodiment. Water treatment combination card 70 also has four SPST relay outputs. In the preferred embodiment, one fluid treatment apparatus 100 will support up to eight water treatment combination cards 70. Water treatment combination card 70 has one two-electrode conductivity cell input, one high impedance analog voltage input for pH or ORP electrodes, two 1,000 ohm platinum RTD resistor temperature sensors, and three sinking pulse, 12 to 24 volts DC inputs. The output of water treatment combination card 70 contains four SPST relays. Water treatment combination card 70 is powered by five volts DC or 24 volts DC via the bus connection, and 24 volts DC is supplied to Hall effect sensors via the terminal connectors. Sensors 382 should be connected directly to a conductivity card. PH and ORP probes 384 should be connected directly to a pH/ORP card by means of low impedance coaxial cable. Terminal blocks 386 are used to connect fluid treatment apparatus terminals to field wiring. Again, this allows smaller gauge wire to be used on the fluid treatment apparatus terminals. Hall effect flow sensors have three lead connections 388, one for positive DC, one for negative DC, and one for the return signal or sinking pulse. Flow inputs may also be used as discrete inputs 390, such as for hand switches and float switches. The input is high when connected to the low side of the DC supply, sinking input. If pH readings are to be temperature compensated, the pH probe is equipped with a 1,000 ohm platinum RTD resistor 392.

A modem card is also used with fluid treatment apparatus 100 to communicate via standard analog telephone lines.

Fluid treatment apparatus 100 is designed to be panel mounted in various types of electrical enclosures with standard mounting brackets. Although fluid treatment apparatus 100 is shown using card guides 108 to mount the different input/output cards, other configurations for fluid treatment apparatus 100 are available. For example, a separate card cage can be used to store the input/output cards and the input/output cards could alternatively be connected to fluid treatment apparatus 100 with a ribbon cable. However, mounting the various input/output cards in the rear of fluid treatment apparatus 100 provides a compact and simple system which is small enough to be panel-mounted in an electrical enclosure.

Figure 16:
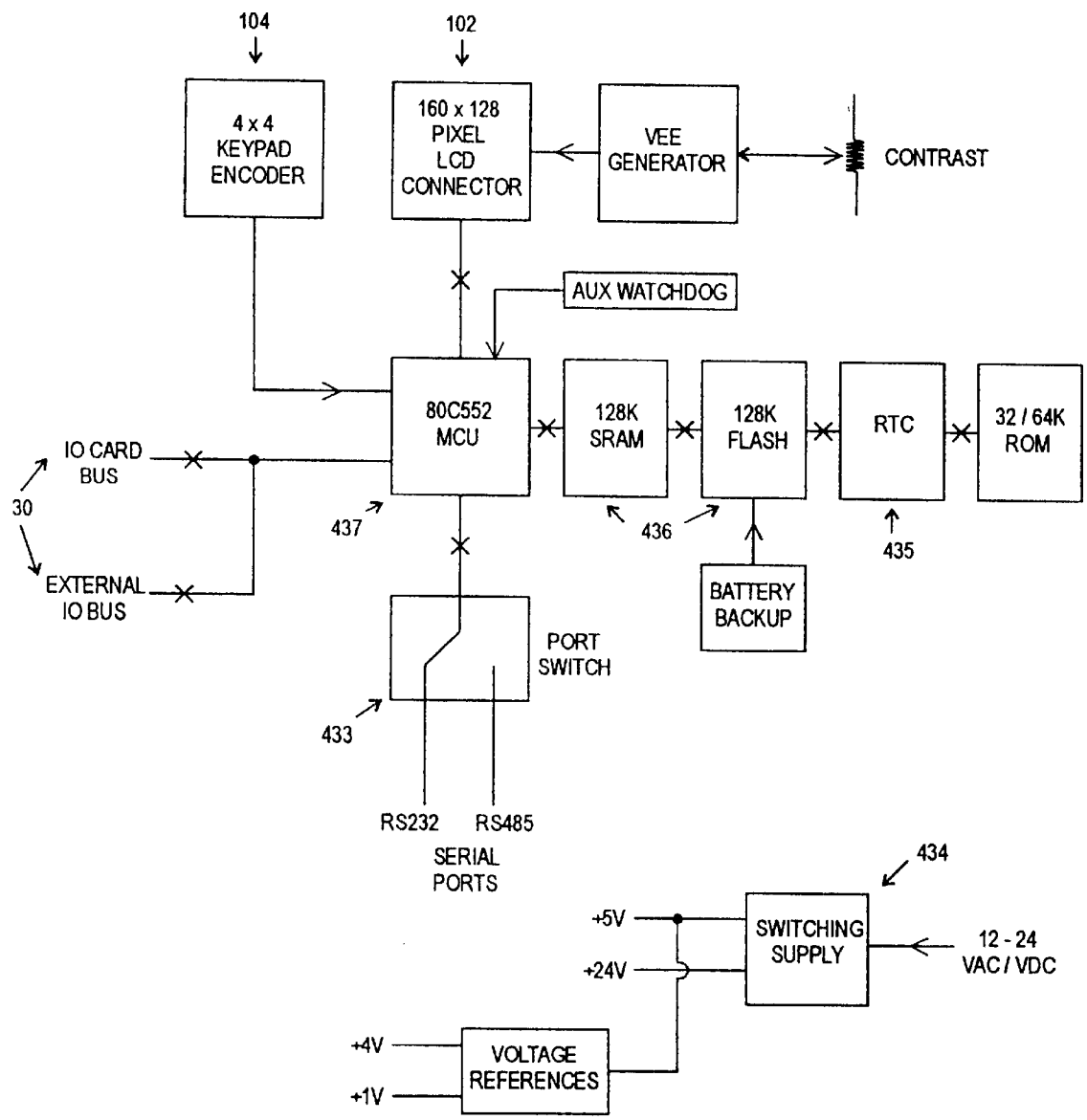
FIG. 16 is an electronic block diagram of the central processing unit of the first embodiment of the present invention.

Attention is now turned to FIGS. 16 to 23, where various input/output cards are shown as electrical block diagrams. FIG. 16 shows CPU 124 as an electrical block diagram. Microprocessor 437 is equipped with memory 436 and real time clock 435. Microprocessor 437 is interfaced with keypad 104 and LCD 102. Microprocessor 437 communicates with the various I/O cards by means of I/O card data bus 30. Microprocessor 437 may also communicate with other devices by means of RS 232 or RS 485 serial ports 433. CPU 124 also includes switching power supply 434 which provides 5 volts DC and 24 volts DC to the I/O cards. It also provides reference voltages of 1 volt DC and 4 volts DC.

Figure 17:
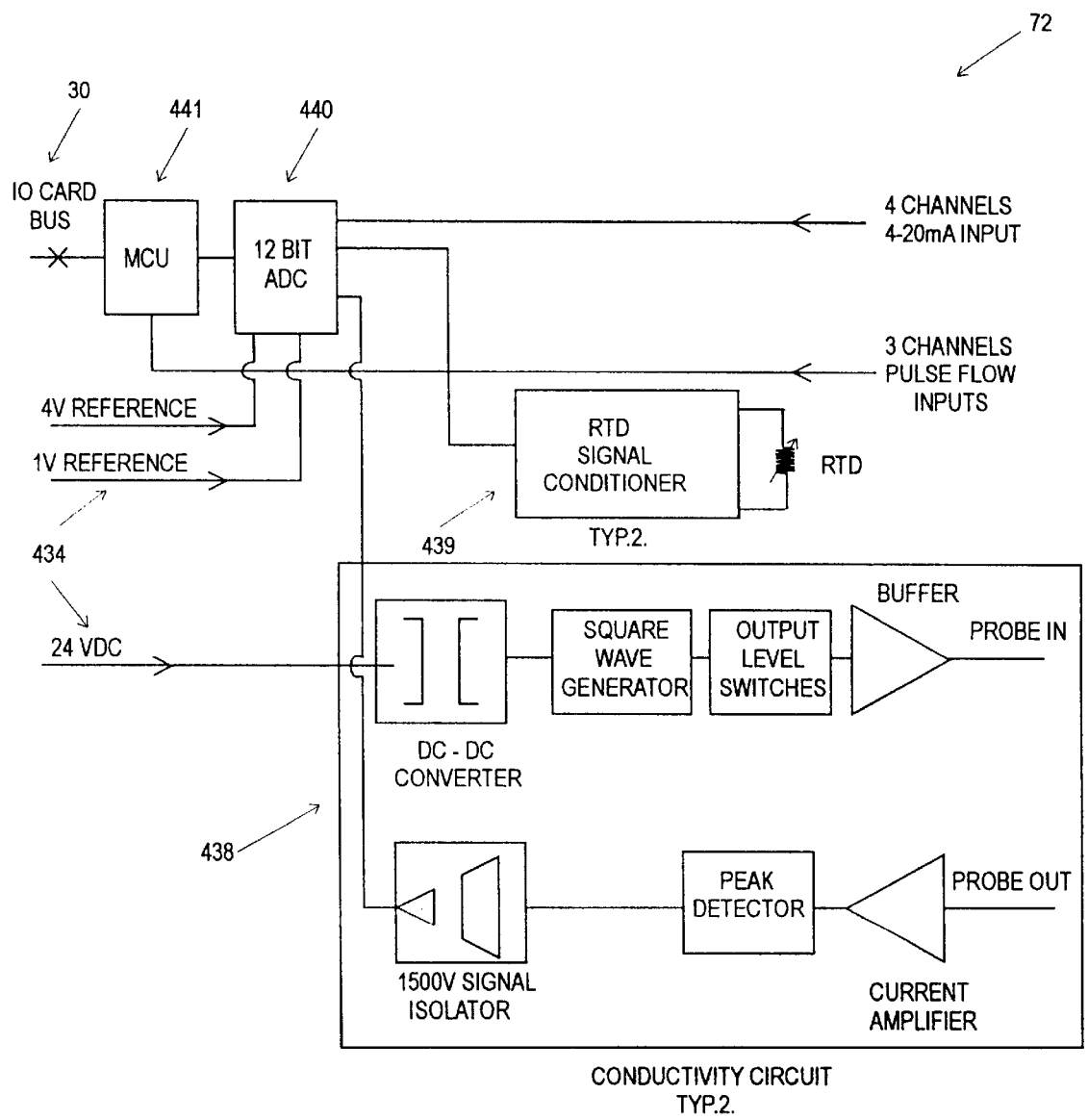
FIG. 17 is an electronic block diagram of the conductivity input card of the first embodiment of the present invention.

FIG. 17 shows conductivity card 72 as an electrical block diagram. Eight channel analog to digital converter 440 is connected to the isolated input circuitry for measuring the conductivity across the probe of conductivity measuring circuit 438. Analog to digital converter 440 is also connected to RTD measuring circuit 439 and other analog inputs. Typically, two conductivity measuring circuits 438 and RTD measuring circuits 439 are on one conductivity card. Conductivity measuring circuit 438 receives 24 volt DC power from power supply 434 from CPU 124. Analog to digital converter 440 also receives reference voltages from power supply 434 from CPU 124. Microprocessor 441 in conductivity card 72 receives data from analog to digital converter 440 in addition to external pulse signals from flow sensors and communicates this data to CPU 124 via data bus 30.

Figure 18:
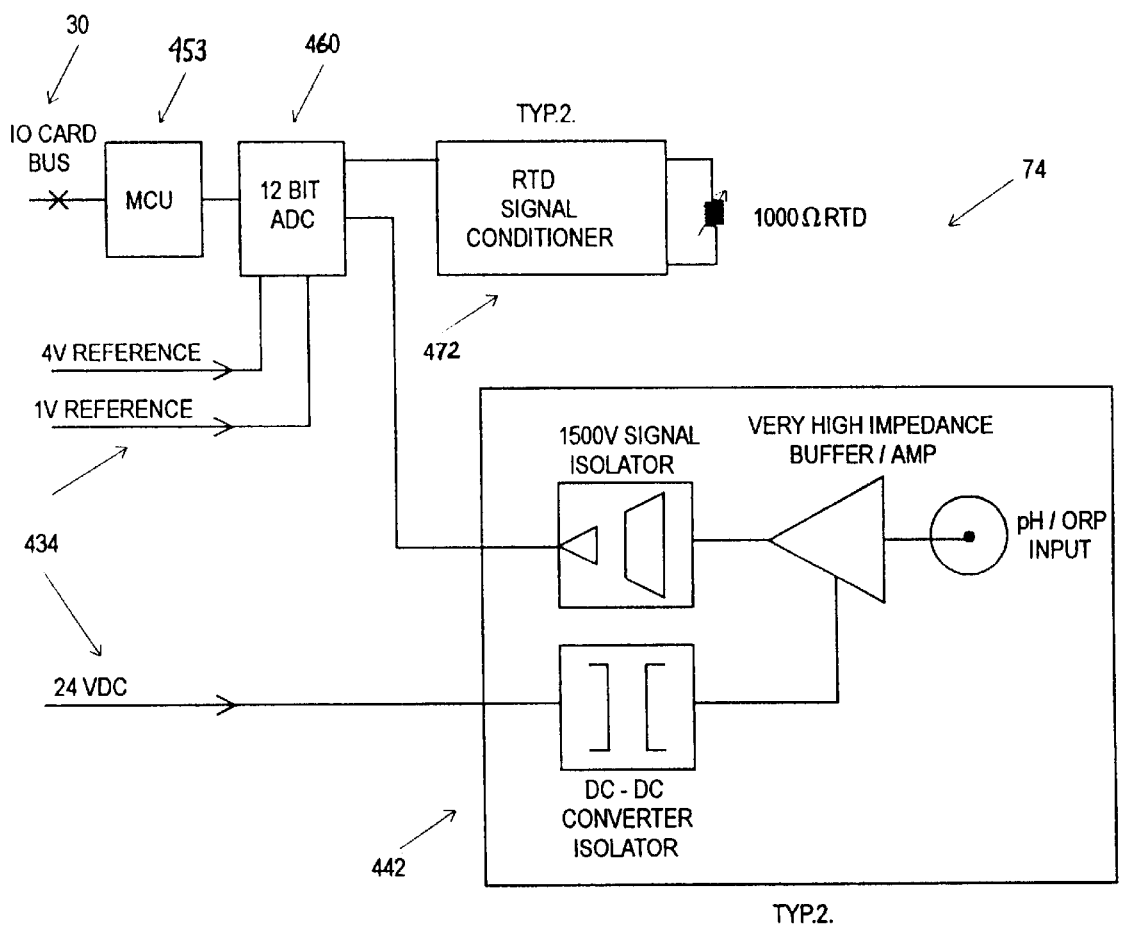
FIG. 18 is an electronic block diagram of the pH/ORP input card of the first embodiment of the present invention.

FIG. 18 shows pH/ORP card 74 as an electrical block diagram. Eight channel analog to digital converter 460 is connected to the isolated input circuitry for measuring the pH or ORP from probe of pH/ORP measuring circuit 442. Analog to digital converter 460 is also connected to RTD measuring circuit 472. Typically, two pH/ORP measuring circuits 442 and RTD measuring circuits 472 are on one pH/ORP card. The pH/ORP measuring circuit 442 receives 24 volt DC power from power supply 434 from CPU 124. Analog to digital converter 460 receives reference voltages from power supply 434 from CPU 124. Microprocessor 453 in pH/ORP card 74 receives data from analog to digital converter 460 and communicates this data to CPU 124 via data bus 30.

Figure 19:
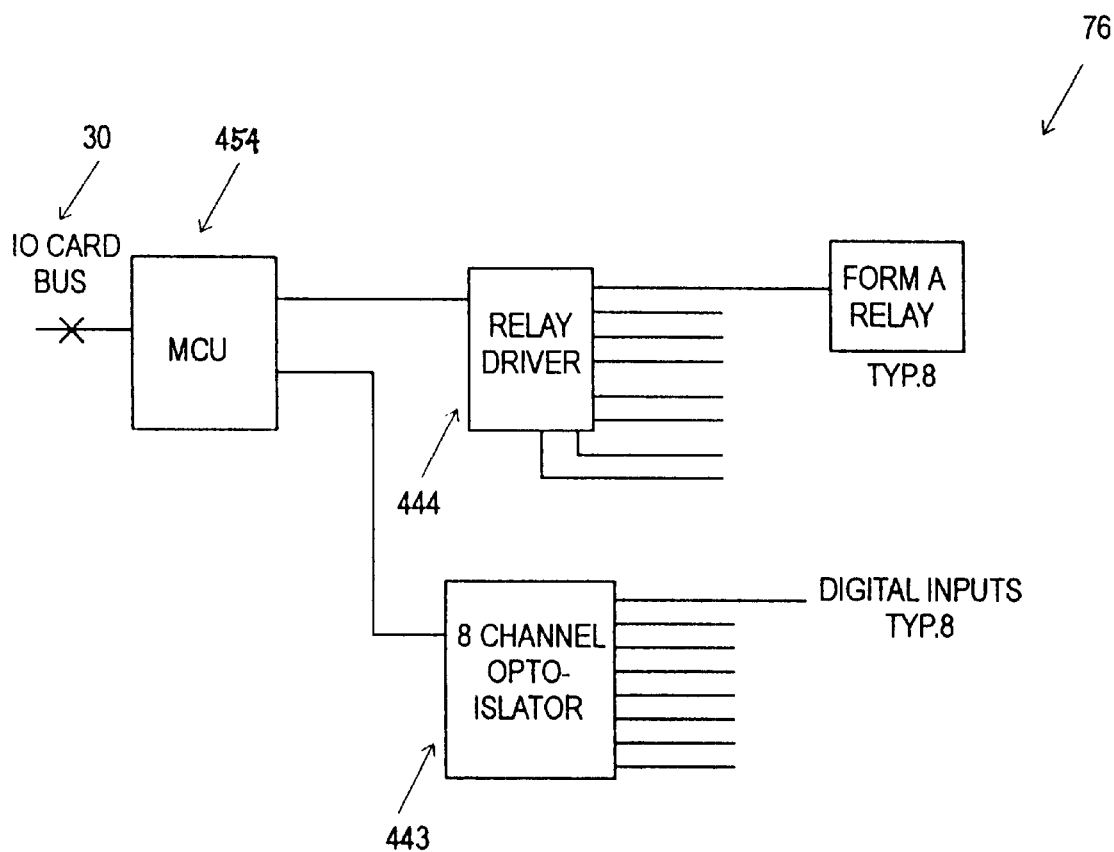
FIG. 19 is an electronic block diagram of the digital input/output card of the first embodiment of the present invention.

FIG. 19 shows the digital I/O card 76 as an electrical block diagram. Microprocessor 454 in digital I/O card 76 receives data from opto isolator 443 and communicates this data to CPU 124 via data bus 30. Microprocessor 454 receives data via data bus 30 and communicates this data to relay driver 444 which in turn controls the state of eight SPST relays.

Figure 20:
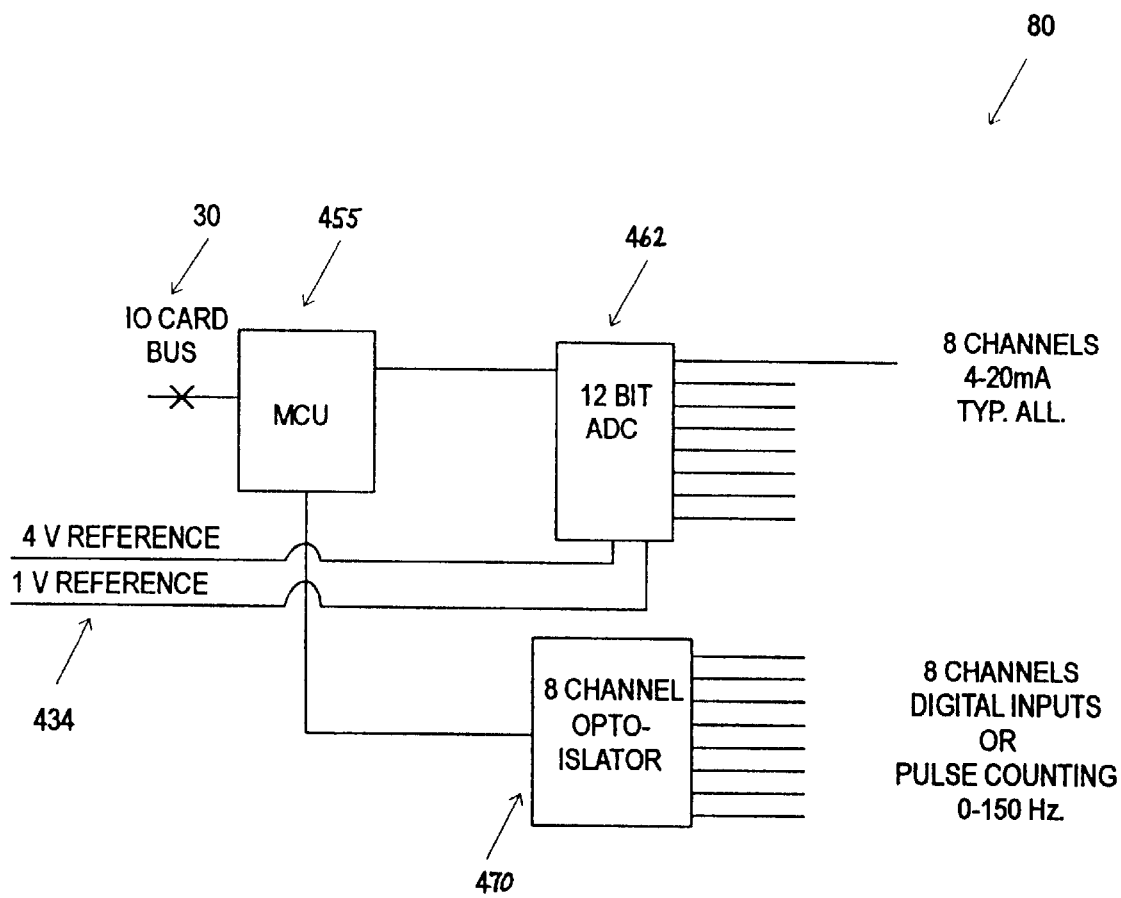
FIG. 20 is an electronic block diagram of the analog/pulse input card of the first embodiment of the present invention.

FIG. 20 shows analog/pulse input card 80 as an electrical block diagram. Microprocessor 455 in analog/pulse input card 80 receives discrete or pulse data from opto isolator 470 and communicates this data to CPU 124 via data bus 30. Analog to digital converter 462 is connected to eight analog inputs and sends data to microprocessor 455. Analog to digital converter 462 receives reference voltages from power supply 434 from CPU 124.

Figure 21:
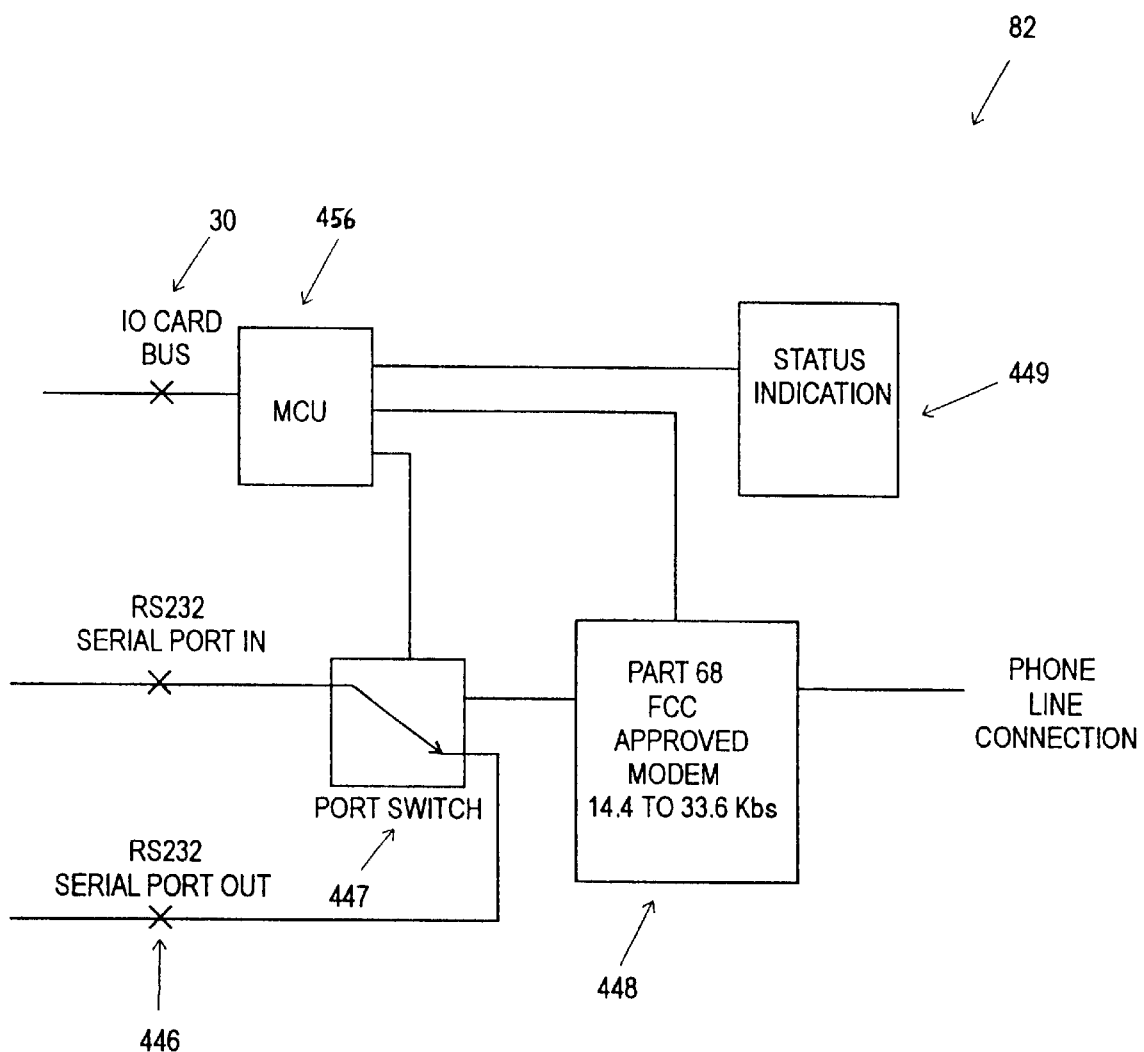
FIG. 21 is an electronic block diagram of the modem card of the first embodiment of the present invention.

FIG. 21 shows modem card 82 as an electrical block diagram. Modem module 448 is connected to a standard analog telephone line and sends data to microprocessor 456 which in turn transmits and receives data via an RS 232 serial port 446. Serial port switch 447 allows other devices to communicate with serial port 446 when the modem is not in use. Microprocessor 456 responds to commands received from CPU 124 via data bus 30. Status indicator lights 449 show the status of modem functions.

Figure 22:
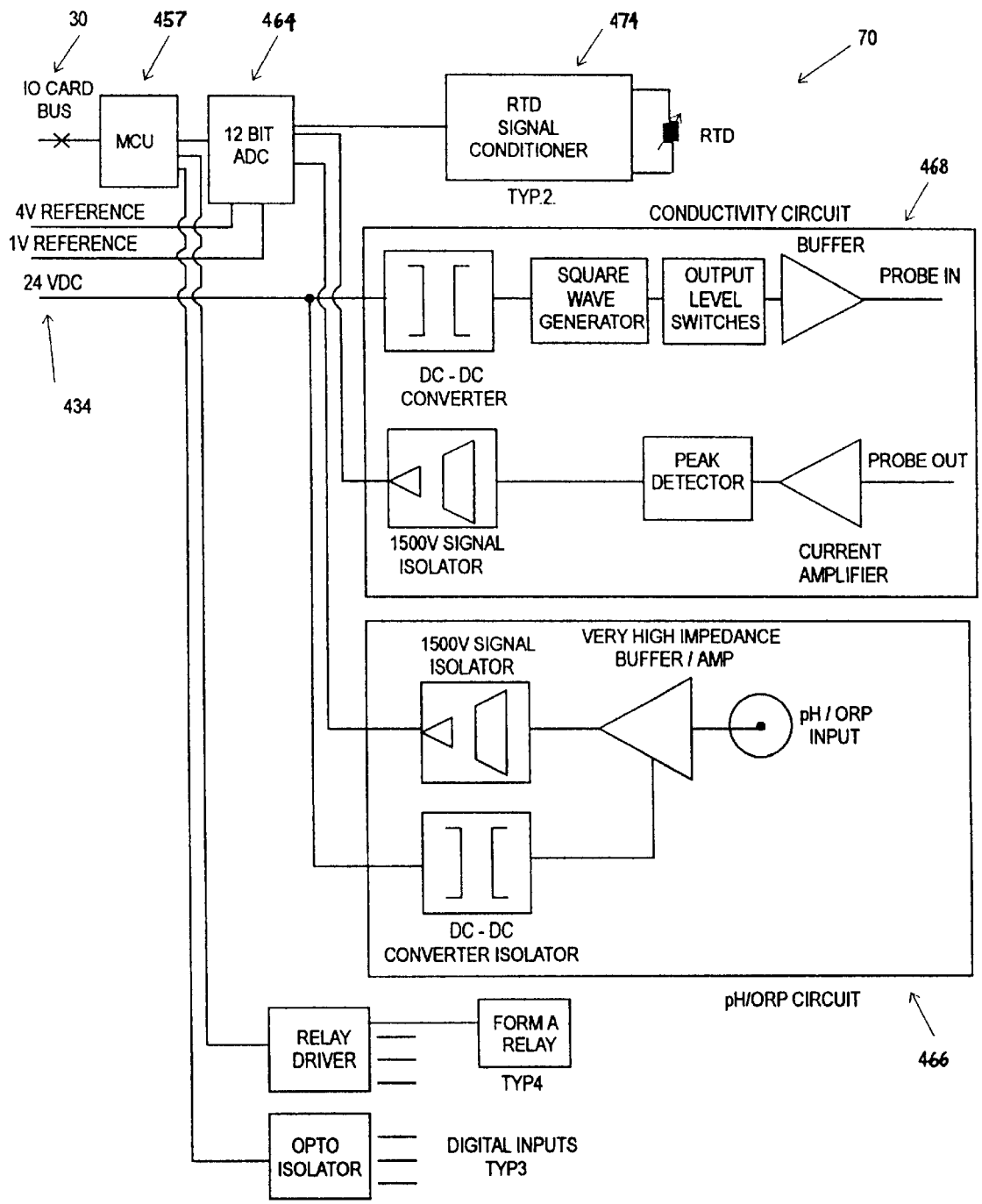
FIG. 22 is an electronic block diagram of the water treatment and reverse osmosis combination input card of the first embodiment of the present invention.

FIG. 22 shows water treatment combination card 70 as an electrical block diagram. Eight channel analog to digital converter 464 is connected to the isolated input circuitry for measuring the pH or ORP from the probe of pH/ORP measuring circuit 466. Analog to digital converter 464 is also connected to the isolated input circuitry for measuring the conductivity across the probe of conductivity measuring circuit 468. Analog to digital converter 464 is also connected to two RTD measuring circuits 474. The pH/ORP measuring circuit 466 and conductivity measuring circuit 468 receive 24 volt DC power from power supply 434 from CPU 124. Analog to digital converter 464 receives reference voltages from power supply 434 from CPU 124. Microprocessor 457 in water treatment combination card 70 receives data from analog to digital converter 464 and communicates this data to CPU 124 via data bus 30.

Figure 23:
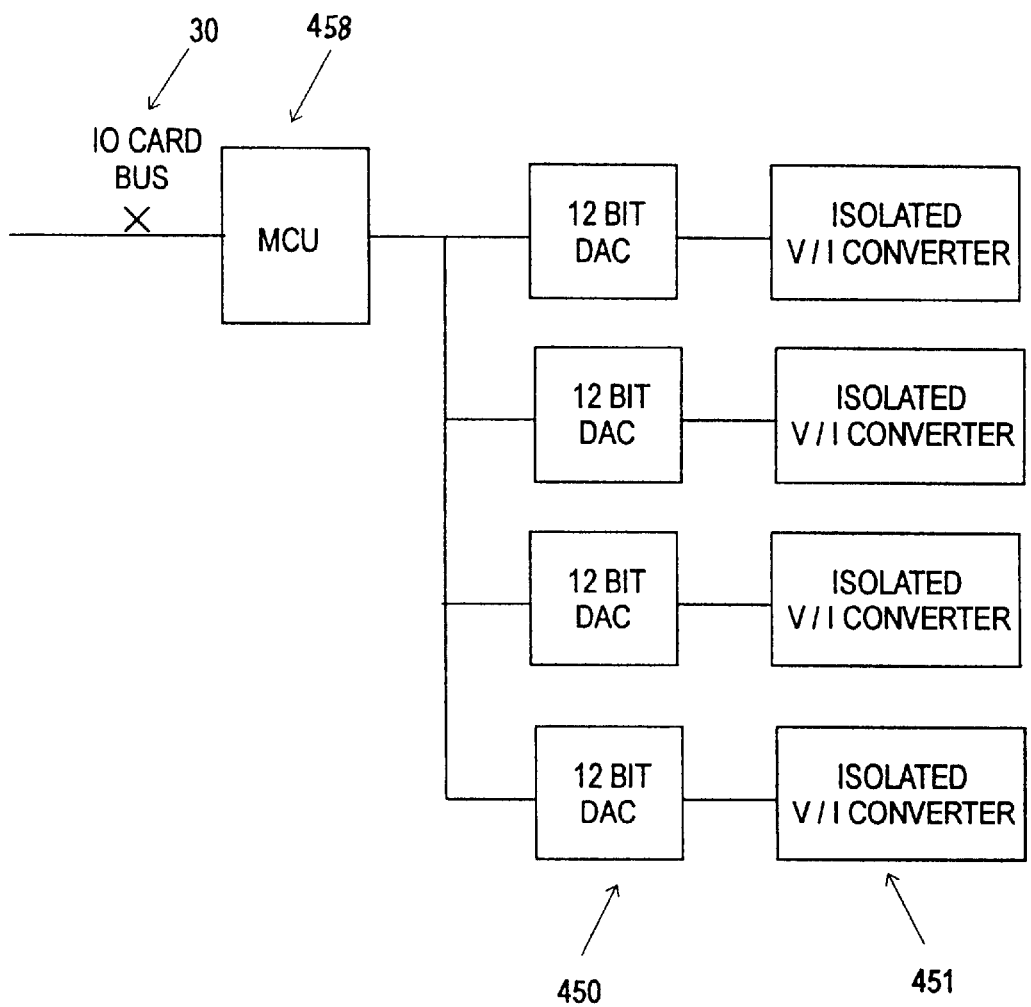
FIG. 23 is an electronic block diagram of the analog output card of the first embodiment of the present invention.
Figure 24:
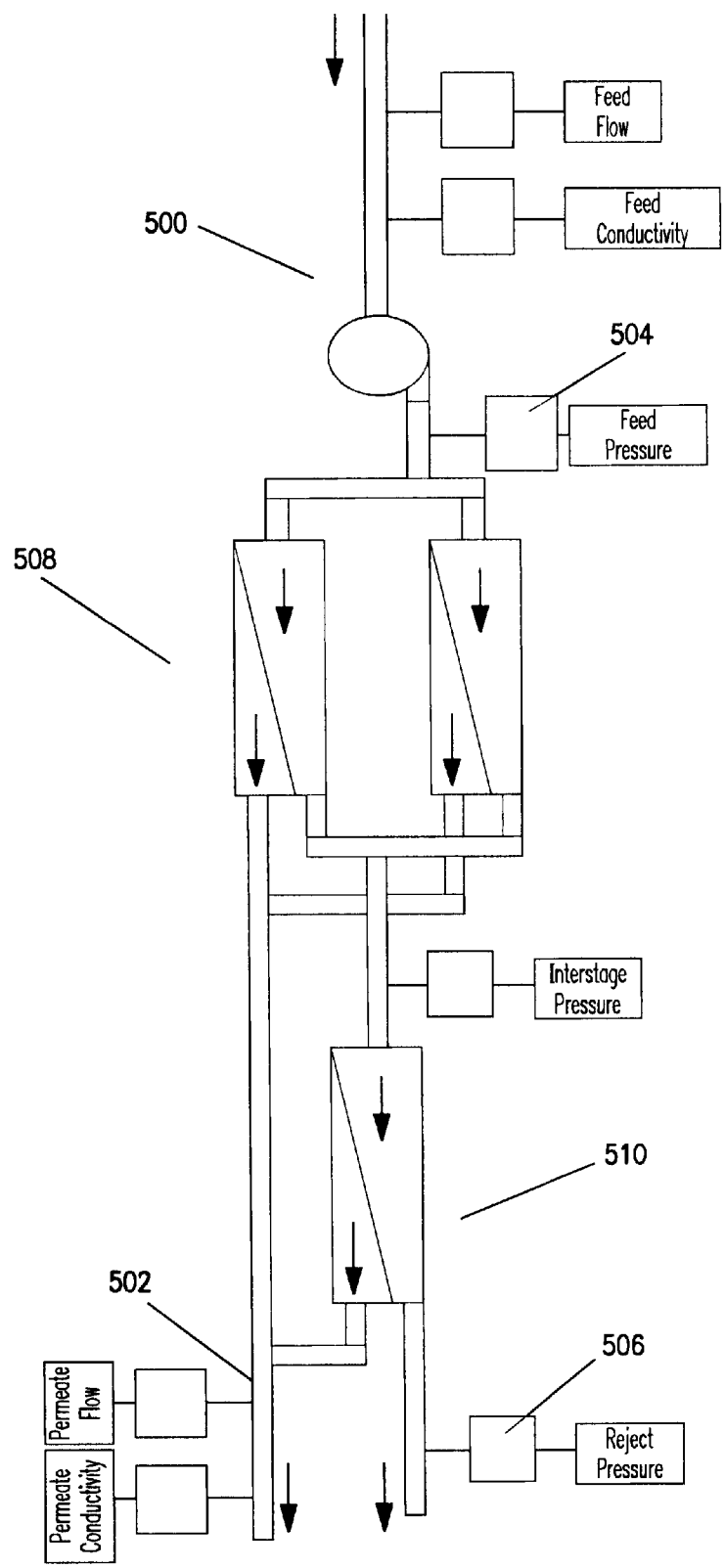
FIG. 24 is a diagram showing reverse osmosis monitoring points.
Figure 25:
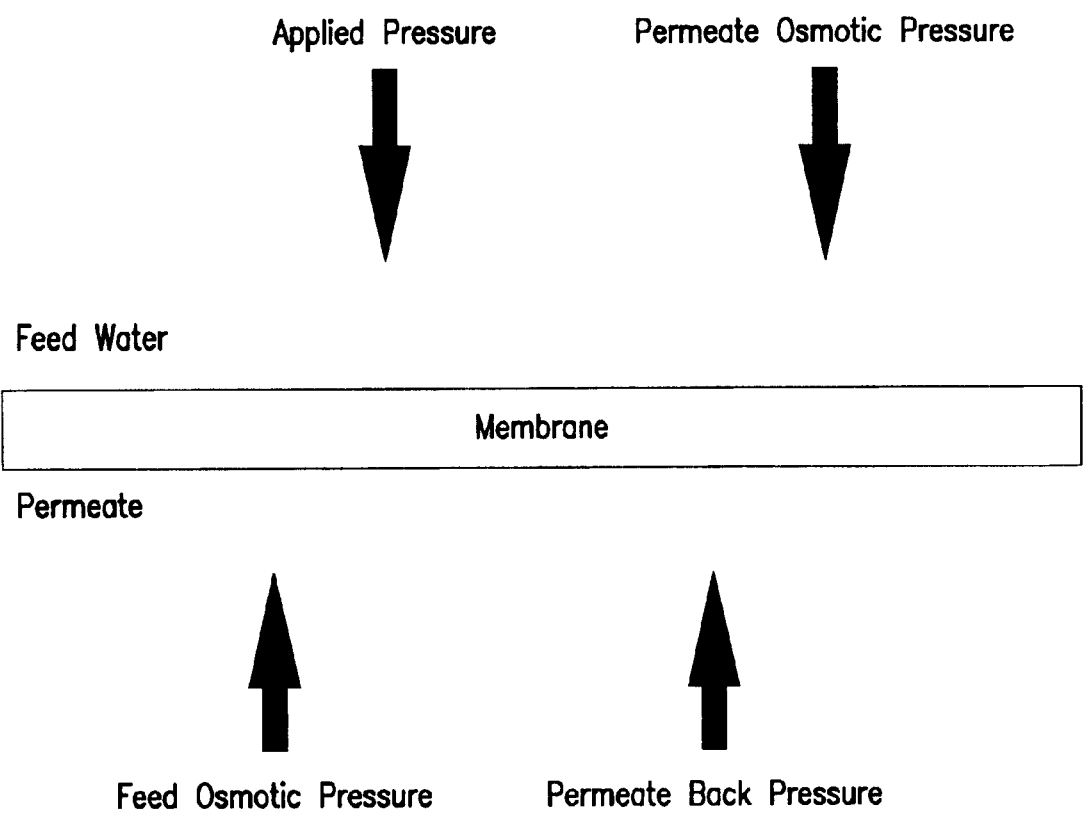
FIG. 25 is a diagram demonstrating the forces acting upon a reverse osmosis membrane.

FIG. 23 shows analog output card 78 as an electrical block diagram. Microprocessor 458 receives data from CPU 124 via data bus 30. Digital to analog converters 450 convert the data to analog signals. These signals are sent to field devices by means of isolated voltage to current converters 451.

The unique configurations of conductivity card 72, pH/ORP card 74, and water treatment combination card 70—in particular the pH/ORP measuring circuits, conductivity measuring circuits, and RTD measuring circuits—which allow the cards to directly receive analytical parameters has applications not only in the fluid treatment apparatus but in other fields as well. The ability to receive analytical parameters directly into the apparatus is entirely new to the field of computers and monitoring equipment. Variations upon these embodiments for communicating with these particular parameters as well as other types of analytical parameters will be obvious to those skilled in the art.

Second Embodiment

The second embodiment of the fluid treatment apparatus builds upon the first to include one or more of the following features: integral sensors that are mounted directly upon the apparatus; a pressure sensing manifold which allows the apparatus to monitor multiple pressures with only one pressure sensor; and a PLC interface that is in direct serial communication with a programmable logic controller (note that multiple second embodiments of the invention can all be connected to a single PLC). The second embodiment is particularly useful for water treatment applications, and most particularly useful for reverse osmosis monitoring.

Figure 26:
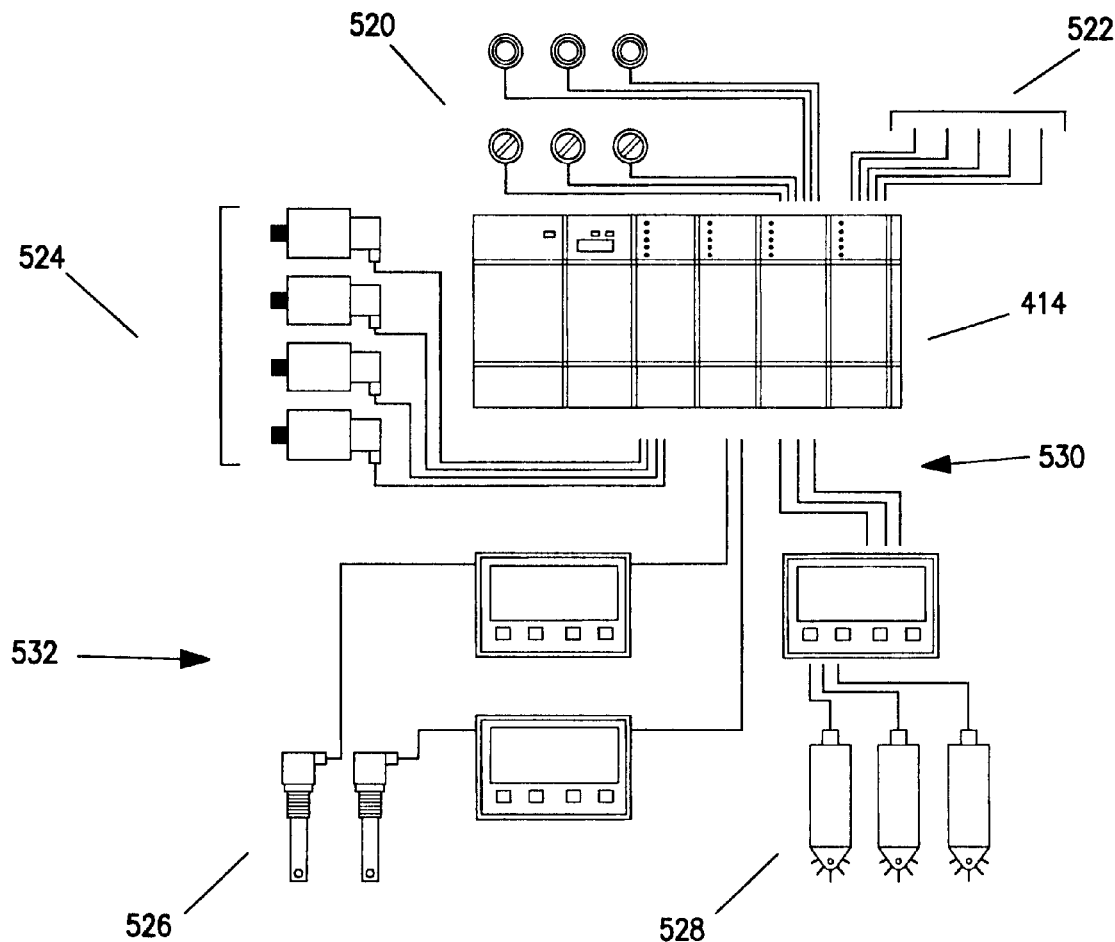
FIG. 26 shows a prior art reverse osmosis monitoring and control system using a programmable logic controller and having panel-mounted indicator lights and switches for operator interface.
Figure 27:
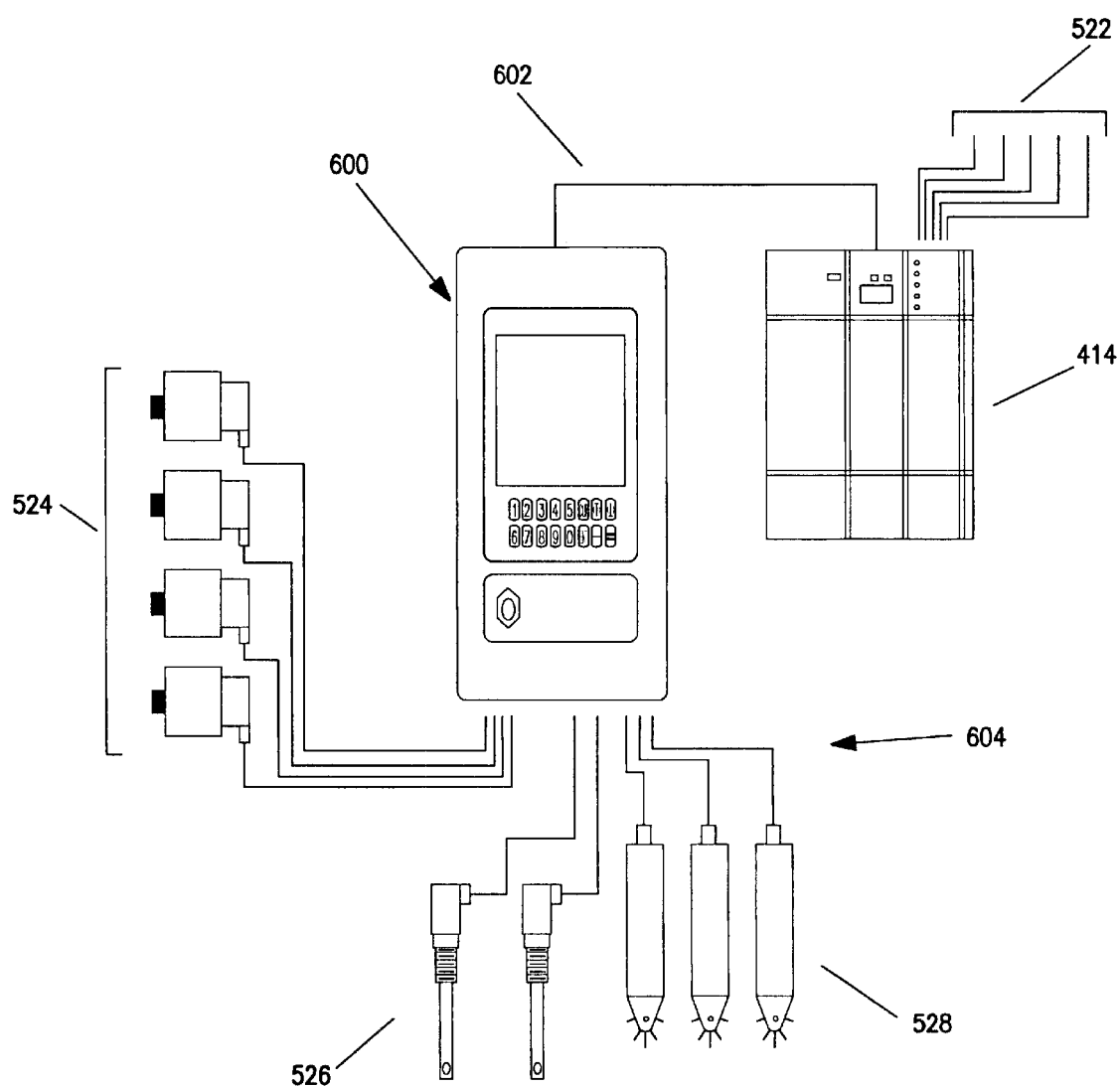
FIG. 27 shows a second embodiment of the present invention for water treatment applications wherein the apparatus communicates directly with a programmable logic controller.

Attention is now returned to FIG. 26, and also to FIG. 27 which shows the second embodiment of fluid treatment apparatus 600 of the present invention. The important differences between apparatus 600 and the prior art configuration of FIG. 26 discussed above, are that apparatus 600 communicates directly with PLC 414 via a serial port and serial connection 602, and signals from conductivity sensors 526, flow sensors 528, and pressure sensors, or other analog inputs, 524, are hardwired into apparatus 600 at 604 rather than directly into PLC 414. Because inputs are fed directly into apparatus 600, the need for various instrumentation as shown at 532 in FIG. 26 is not necessary and simplifies the monitoring and control of the system. While apparatus 600 is shown receiving conductivity, flow, and pressure, or other analog inputs, it is to be understood that apparatus 600 can receive a different number of inputs and other inputs other than as shown. The invention is not to be limited to the quantity and type of inputs shown in FIG. 27. Alternatively, apparatus 600 can receive signals from various input/output modules on a network, such as an ethernet, RS 485, or other multi-drop network.

Because apparatus 600 communicates directly with PLC 414 via serial connection 602, multiple hardwired connections, shown at 530 in FIG. 26, to PLC 414 are not necessary. Apparatus 600 serves as an operator interface for PLC 414 and eliminates panel-mounted switches and indicator lights—520 in FIG. 26. Furthermore, eliminating the multiple hardwired connections between apparatus 600 and PLC 414, allows for a smaller PLC to be utilized.

Because apparatus 600 has the ability to communicate with PLCs via a single serial connection 602, alarm setpoints programmed in apparatus 600 can be used to control logic functions in PLC 414. Indicator messages and push-buttons on apparatus 600 can be used in the PLC logic via corresponding control or indicator bits. Time delays, counter pre-sets, and other variables used by the PLC can be changed from the keypad of apparatus 600.

Apparatus 600 can communicate with a number of PLCs via various serial protocols. All PLC connections are made with first serial port 620 located at the bottom of apparatus 600 enclosure as shown and described in FIG. 29. Table 5 lists examples of PLCs with which apparatus 600 is currently compatible. Table 5 also includes the connecting port for the PLC as well as the cable necessary for the PLC connection.

TABLE 5

PLCs Compatible With Fluid Treatment Apparatus

| PLC Model No. | Manufacturer | PLC Connection Port | Cable Part No. |
|---|---|---|---|
| DL 05 (All) | Koyo | Port 2 | D2-DSCBL |
| D2-240 | Koyo | Port 2 | D2-DSCBL |
| D2-250 | koyo | Port 2 | D2-DSCBL-1 |
| MicroLogix 1000 | Allen-Bradley | Communication Port | 1761-CBL-PM02 |
| MicroLogix 1500 | Allen-Bradley | Communication Port | 1761-CBL-PM02 |
| SLC 5/03 | Allen-Bradley | Channel 0 | 1747-CP3 |
| SLC 5/04 | Allen-Bradley | Channel 0 | 1747-CP3 |

Figure 28:
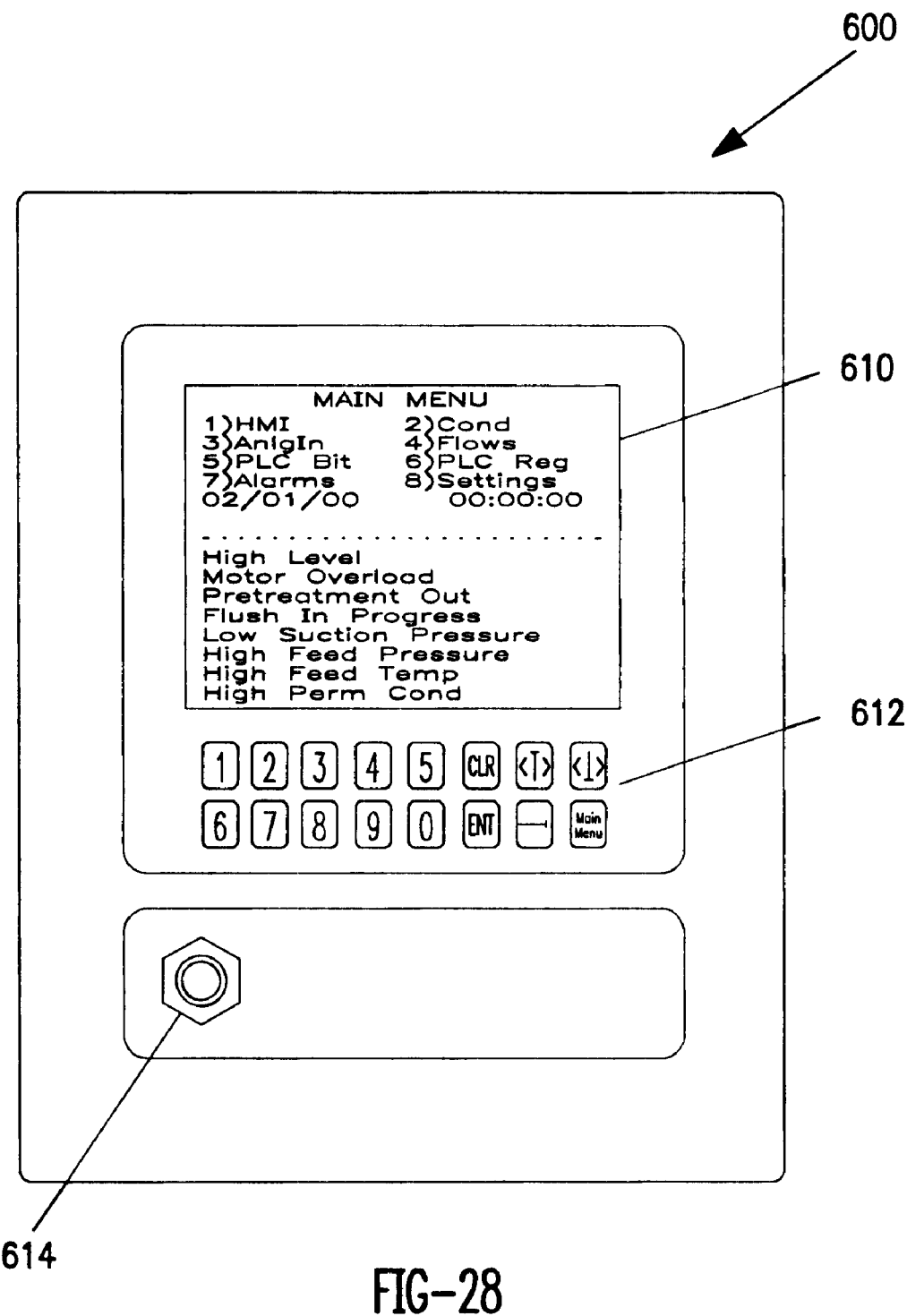
FIG. 28 is a front view of the display module of the second embodiment of the apparatus of the present invention.

Attention is now turned to FIG. 28 which is a front view of apparatus 600. Display 610 and keypad 612 is used as the operator interface for both apparatus 600 and associated PLC 414 (shown in FIGS. 26 and 27). Display 610, much like display 102 described in the first embodiment (shown in FIG. 2), is preferably a back-lit, 16 line by 20 character display for showing operating data both from the inputs as well as from PLC 414. The indicator messages on display 610 are controlled by bits in PLC 414. These messages may be customized by the operator.

Numeric keypad 612 below display 610, much like keypad 104 described in the first embodiment, is used for data entry to apparatus 600 (such as setpoints). Keypad 612 serves a number of functions. It allows the operator to control the PLC by means of "soft" "Hand/Off/Auto" (HOA) and pushbutton switches which will be described further below. These switches control bits in PLC 414 and allow apparatus 600 to be used as an operator interface. It also allows the operator to make data entry and settings changes, both in the apparatus 600 as well as in PLC 414. Keypad 612 can be used to enter values into the PLC registers, for example, time delays, counter presets, etc. External serial connector 614 allows data to be downloaded from the front of apparatus 600 thus enabling quick access to data without having to open the enclosure of the apparatus.

Turning to FIG. 29, access to serial ports 618 and 620 and optional modem 622 is gained from the bottom of apparatus 600. A first serial port 620 is used for PLC communication. A second serial port 618 is shared with the modem connection and is generally wired to the external serial connector 614 on the front of apparatus 600, shown in FIG. 28. Modem 622 allows operating conditions to be viewed in real time from remote locations. It also allows retrieval of data logged by apparatus 600, and allows PLC 414 to be controlled remotely. Modem 622 may be connected to an analog phone line via a standard modular telephone connector.

FIGS. 30a–b show terminal strip 624 on the rear of apparatus 600 that allow the conductivity, flow, and analog sensor inputs to be connected directly to apparatus 600 without the use of additional instrumentation. Screw terminals such as shown at 626 are provided for making connections for sensor inputs and power. Terminal strip 624 is accessible through a cover from the rear of apparatus 600. The terminals are numbered in descending order from top to bottom. Power is also connected via terminal strip 624. Preferably apparatus 600 is powered from a 24 volt DC source providing at least 1.2 amps. The negative side of the DC power supply should be connected to a common ground reference (earth ground) for proper operation of apparatus 600. Any power supply powering transmitters connected to apparatus 600 should be referenced to the same ground. The positive side of the power source preferably has a 1.5 amp fuse wired between the power source and the power input terminal.

Apparatus 600 is configured to present the operator with a number of screens on display 610. See FIG. 28 discussed above. These screens serve several purposes including: providing choices to go to other screens; view data being monitored by the apparatus or the PLC; and allow settings in either the apparatus or the PLC to be changed. The main menu screen is displayed shortly after power up and is shown in FIG. 28. From the main menu, the operator may select any other screen by pressing the appropriate selection number from keypad 612. Pressing the "Main Menu" key from any of the screens always returns the display to the main menu screen.

Figure 31A:
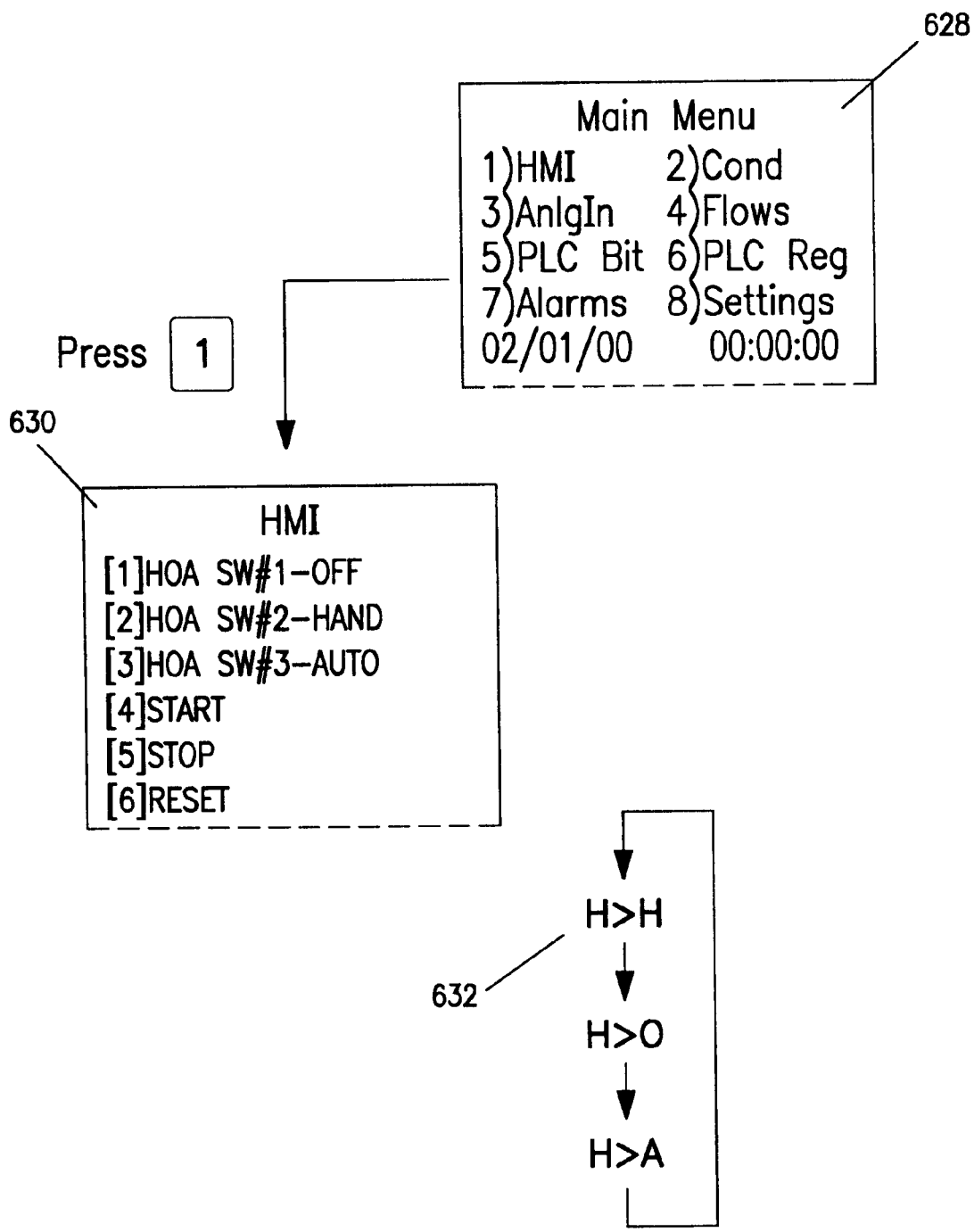
FIG. 31a shows the human interface screen of the second embodiment of the present invention.

Attention is now turned to FIG. 31a. Main menu 628 displays eight options for accessing other screens for monitoring and control: human machine interface (HMI), conductivity (Cond), analog, flow, PLC bit status, PLC registers, alarms, and settings. HMI screen 630 is accessed by pressing "1" from the main menu screen. HMI screen 630 allows the operator to manipulate the control functions of the PLC by means of three selector switches and three push-button switches, labelled 1–6. When HMI screen 630 is displayed, switches 1–3 activate three position HOA switches. The indicators "Off," "Hand," and "Auto" indicate the position of the switches. Each time a switch is pressed and held, the position indicator shows the current position of the switch and also cycles through the three switch positions (HOA) each time the corresponding numeric key is pressed as shown at 632. If the key is not pressed again within three seconds, the current switch position is changed to the new selection. Two different bits in the PLC are set depending upon whether the switch is in the "Hand" or "Auto" position, and in the "Off" position both bits are set to the zero state, as follows:

| Setting | PLC bit 1 | PLC bit 0 |
|---|---|---|
| Off | 0 | 0 |
| Hand | 0 | 1 |
| Auto | 1 | 0 |

Switches 4–6 act as momentary pushbuttons also controlling three bits in the PLC. When the key is pressed, the bit in the PLC is set high for two seconds. The names given to the switches and the position labels can be customized with the apparatus' configuration software.

Figure 31B:
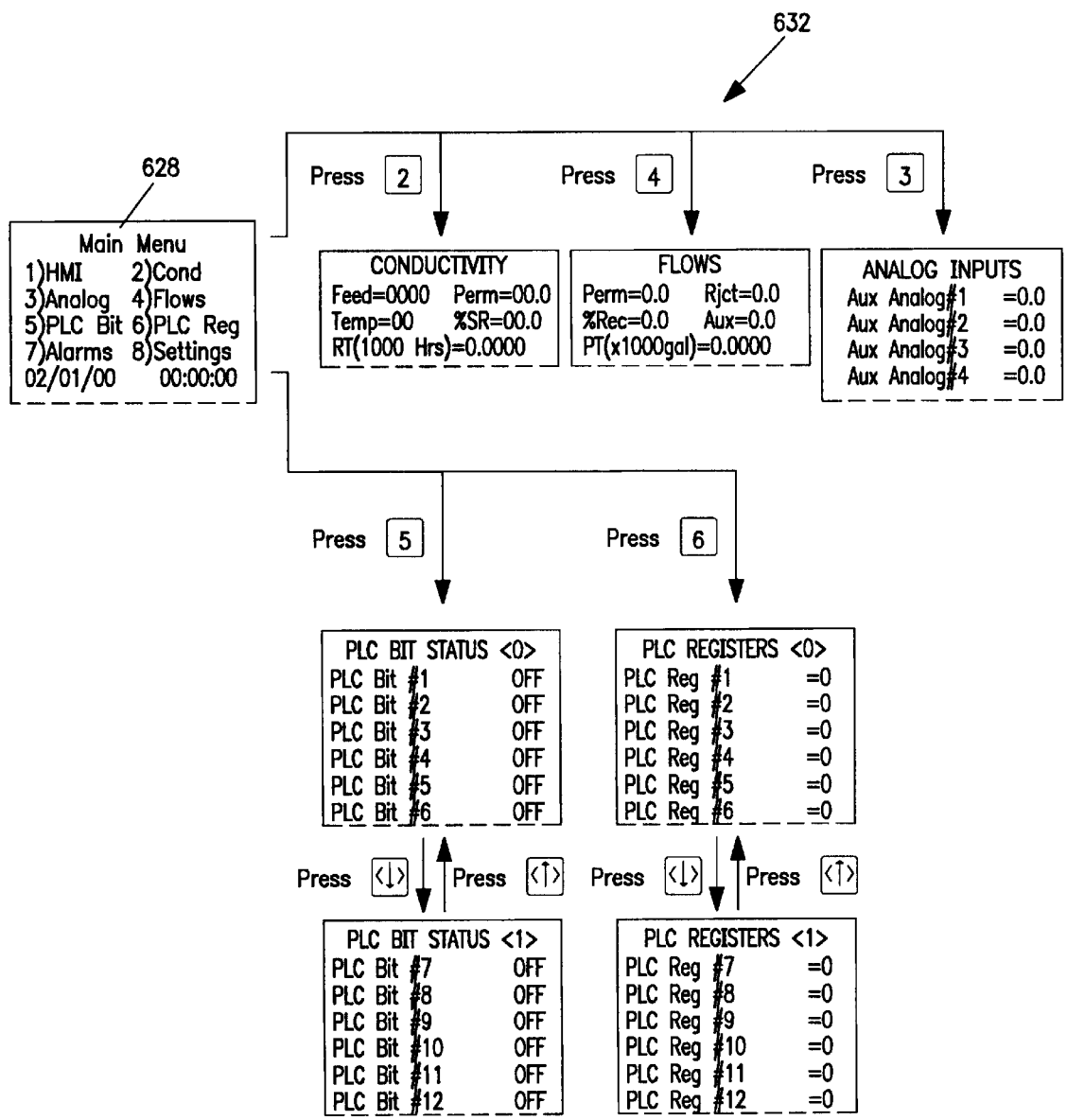
FIG. 31b shows the data screens of the second embodiment of the present invention.

FIG. 31b shows the data screens which display the data gathered by the conductivity inputs, flow inputs, feed temperature input (integral to conductivity sensor), analog inputs, and PLC registers. Data screens 632 are accessed by pressing the appropriate number from main menu 628. The conductivity data screen shows the feed conductivity ($\mu$S), permeate conductivity ($\mu$S), feed temperature (C), and percent salt rejection based upon feed and permeate conductivity. The conductivity data screen also displays system run time in thousands of hours.

The flow data screen shows the permeate flow, reject flow, auxiliary flow, and percent recovery. The units used for flow are a function of the K factors entered by the user in the settings data entry screens (i.e., pulses per gallon yields flow in gallons per minute). The flow data screen also shows the permeate total volume in multiples of one thousand units.

The analog input screens display the four analog input channels. Units of the analog values are a function of the range configured by the user in the appropriate settings data entry screen. The names for the analog channels can be customized by the operator by the configuration software.

Figure 31C:
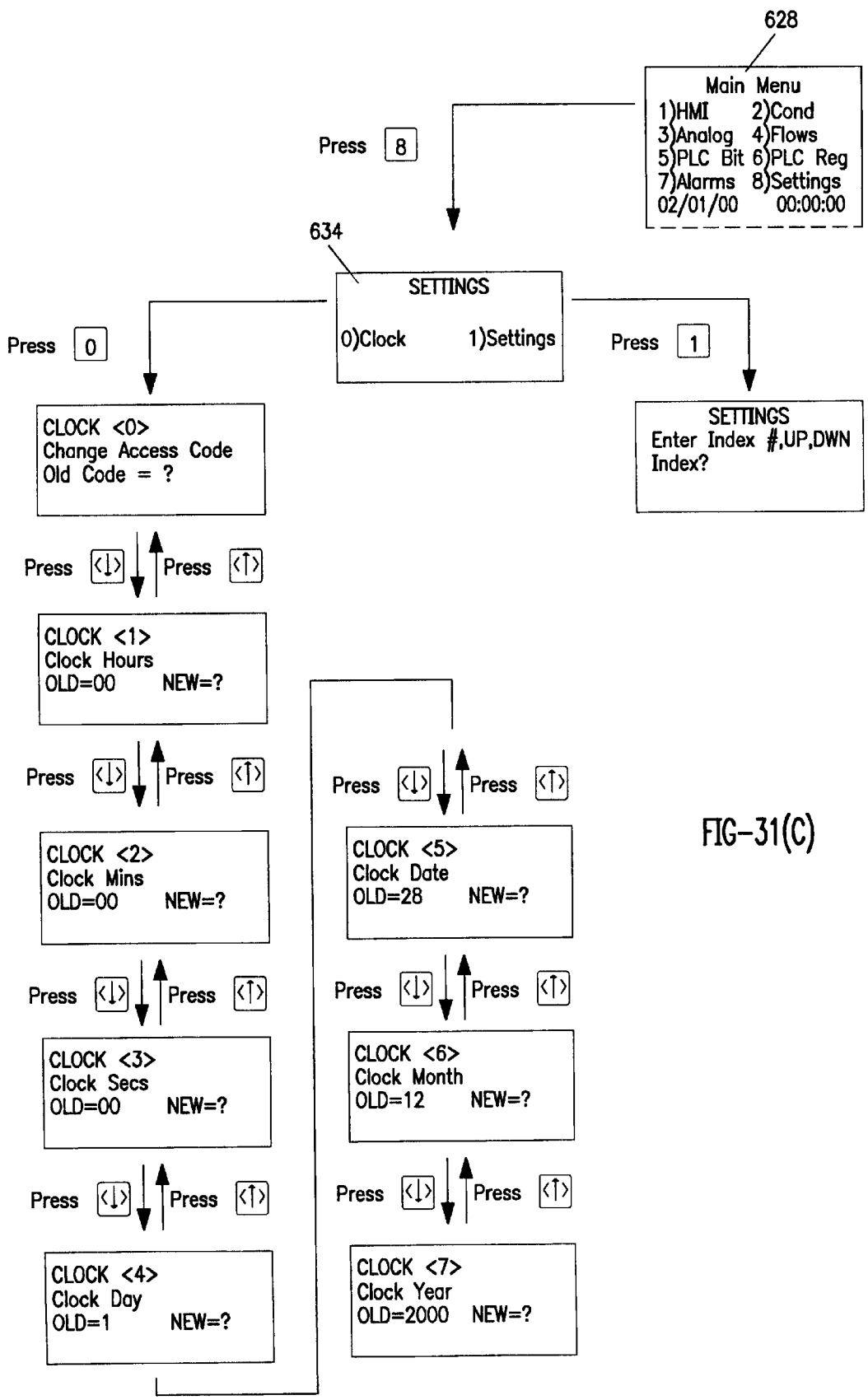
FIG. 31c shows the setting screen of the second embodiment of the present invention.

FIG. 31c shows the settings screen 634 which allows access to the numerous data entry screens which permit the operator to change alarm setpoints, time delays, deadband values, time, date, PLC register values, and calibration factors. Pressing "0" from settings screen 634 gives the operator access to the clock settings to set the real time clock in apparatus 600.

The clock settings also include a data entry screen for changing the user access code. This code is necessary to gain access to the main settings data entry screens where setpoints, time delays, etc., are changed. As a convenience, the settings data entry screens may be re-entered without the access code for a period of several minutes after exiting. Upon entering the settings data entry screens, the operator will have the option of entering an index number for a particular setting. Since there are over eighty settings, this enables the operator to go directly to a particular setting without scrolling through the entire list of settings. Alternatively, the operator may scroll through the settings with the up and down arrow keys.

Table 6 below lists the index number of all of the settings data entry screens, the abbreviation used on the screen, the full name of the setting, and any other pertinent information on that particular setting.

TABLE 6

Fluid Treatment Apparatus Settings

| Index | Abbreviation | Full Name | Format | Details |
|---|---|---|---|---|
| 0 | Lo SR SP | Low Salt Rejection Setpoint | 00.0 | Setpoint (in %) which activates the alarm for low salt rejection. The right arrow key is used to enter the decimal when entering the setpoint. |
| 1 | Lo SR DB | Low Salt Rejection Deadband | 00.0 | Deadband (in %) through which the salt rejection value must pass before the salt rejection alarm is released. The right arrow key is used to enter the decimal when entering the setpoint. |
| 2 | Lo SR TD | Low Salt Rejection Time Delay | 000 | Delay (in seconds) before the low salt rejection alarm is activated once the current value falls below the setpoint. The time delay is reset when the current value of the salt rejection rises above the setpoint plus the deadband. |
| 3 | Hi Rec SP | High Recovery Setpoint | 00 | Setpoint (in %) which activates the alarm for high recovery. |
| 4 | Hi Rec DB | High Recovery Deadband | 00 | Deadband (in %) through which the recovery value must pass before the salt rejection alarm is released. |
| 5 | Hi Rec TD | High Recovery Time Delay | 000 | Delay (in seconds) before the high recovery alarm is activated once the current value rises above the setpoint. The time delay is reset when the current value of the recovery drops below the setpoint less the deadband. |
| 6 | Lo Rej Flow SP | Low Reject Flow Setpoint | 00.0 | Setpoint (in gpm) which activates the alarm for low reject flow. |
| 7 | Lo Rej Flow DB | Low Reject Flow Deadband | 00.0 | Deadband (in gpm) through which the reject flow value must pass before the low reject flow alarm is released. |
| 8 | Lo Rej Flow TD | Low Reject Flow Time Delay | 000 | Delay (in seconds) before the low reject flow alarm is activated once the current value falls below the setpoint. The time delay is reset when the current value of the reject flow rises above the setpoint plus the deadband. |
| 9 | Hi Perm Cond SP | High Permeate Conductivity Setpoint | 00.0 | Setpoint (in uS) which activates the alarm for high permeate conductivity. |
| 10 | Hi Perm Cond DB | High Permeate Conductivity Deadband | 00.0 | Deadband (in uS) through which the permeate conductivity value must pass before the permeate conductivity alarm is released. |
| 11 | Hi Perm Cond TD | High Permeate Conductivity Time Delay | 000 | Delay (in seconds) before the high permeate conductivity alarm is activated once the current value rises above the setpoint. The time delay is reset when the current value of the permeate conductivity drops below the setpoint less the deadband. |
| 12 | Hi Feed Cond SP | High Feed Conductivity Setpoint | 0000 | Setpoint (in uS) which activates the alarm for high feed conductivity. |
| 13 | Hi Feed Cond DB | High Feed Conductivity Deadband | 0000 | Deadband (in uS) through which the feed conductivity value must pass before the feed conductivity alarm is released. |
| 14 | Hi Feed Cond TD | High Feed Conductivity Time Delay | 000 | Delay (in seconds) before the high feed conductivity alarm is activated once the current value rises above the setpoint. The time delay is reset when the current value of the feed conductivity drops below the setpoint less the deadband. |
| 15 | Hi Feed Temp SP | High Feed Temperature Setpoint | 00.0 | Setpoint (° C.) which activates the alarm for high feed temperature. |
| 16 | Hi Feed Temp DB | High Feed Temperature Deadband | 00.0 | Deadband (° C.) through which the permeate conductivity value must pass before the high feed temperature alarm is released. |
| 17 | Hi Feed Temp TD | High Feed Temperature Time Delay | 000 | Delay (in seconds) before the high feed temperature alarm is activated once the current value rises above the setpoint. The time delay is reset when the current value of the feed temperature drops below the setpoint less the deadband. |
| 18 | Lo Feed Temp SP | Low Feed Temperature Setpoint | 00.0 | Setpoint (° C.) which activates the alarm for low feed temperature. |
| 19 | Lo Feed Temp DB | Low Feed Temperature Deadband | 00.0 | Deadband (° C.) through which the feed temperature value must pass before the low feed temperature alarm is released. |
| 20 | Lo Feed Temp TD | Low Feed Temperature Time Delay | 000 | Delay (in seconds) before the low feed temperature alarm is activated once the current value falls below the setpoint. The time delay is reset when the |

TABLE 6-continued

Fluid Treatment Apparatus Settings

| Index | Abbreviation | Full Name | Format | Details |
|---|---|---|---|---|
| 21 | PLC Preset 1 | | 00000 | current value of the feed temperature rises above the setpoint plus the deadband. The value entered is written to the appropriate register location in the PLC. |
| 22 | PLC Preset 2 | | | |
| 23 | PLC Preset 3 | | | |
| 24 | PLC Preset 4 | | | |
| 25 | PLC Preset 5 | | | |
| 26 | PLC Preset 6 | | | |
| 27 | PLC Preset 7 | | | |
| 28 | PLC Preset 8 | | | |
| 29 | PLC Preset 9 | | | |
| 30 | PLC Preset 10 | | | |
| 31 | PLC Preset 11 | | | |
| 32 | PLC Preset 12 | | | |
| 33 | PFlow K Factor | Permeate Flow K Factor | 000.0 | Calibration factors for pulse flow sensors (K Factor = pulses per gallon) |
| 34 | RFlow K Factor | Reject Flow K Factor | | |
| 35 | AFlow K Factor | Auxiliary Flow K Factor | | |
| 36 | Feed Cal. Factor | Feed Conductivity Cal. Factor | 0.000 | Calibration factors for conductivity channels. These values are automatically modified if calibration is performed with standard solutions (Index Nos. 80 and 81) |
| 37 | Perm Cal. Factor | Permeate Conductivity Cal. Factor | | |
| 38 | FTemp Calibration | Feed Temperature Calibration | 000.0 | The temperature calibration factors are used to calibrate the temperature detectors in the conductivity sensors. The appropriate conductivity sensor is place in a solution of a known temperature. The correction factor is adjusted up or down until the displayed temperature matches that of the sensor. |
| 39 | PTemp Calibration | Permeate Temperature Calibration | 000.0 | |
| 40 | Aln 1 Zero | Analog Input 1 Zero Adjustment | 000 | Calibration factor which allows analog input channel 1 to be zeroed at 4 mA. |
| 41 | Aln 1 Full Scale | Analog Input 1 Full Scale Adjustment | 0000 | Calibration factor which allows analog input channel 2 to be set to full scale at 20 mA. |
| 42 | Aln 1 Range | Analog input 1 Range | 0000 | Range, in engineering units, for the full span of the analog transmitter connected to analog input 1. |
| 43 | Aln 1 Lo SP | Analog Input 1 Low Setpoint | 000.0 | Setpoint (in engineering units) which activates the alarm when the analog input is low. |
| 44 | Aln 1 Lo DB | Analog Input 1 Low Deadband | 000.0 | Deadband (in engineering units) through which the analog input value must pass before the alarm is released. |
| 45 | Aln 1 Lo TD | Analog Input 1 Low Time Delay | 000 | Delay (in seconds) before the alarm is activated once the current analog value falls below the setpoint. The time delay is reset when the current value of the analog signal rises above the setpoint plus the deadband. |
| 46 | Aln 1 Hi SP | Analog Input 1 High Setpoint | 000.0 | Setpoint (in engineering units) which activates the AquaLynx ™ alarm when the analog input is high. |
| 47 | Aln 1 Hi DB | Analog Input 1 High Deadband | 000.0 | Deadband (in uS) through which the analog input value must pass before the alarm is released. |
| 48 | Aln 1 Hi TD | Analog Input 1 High Time Delay | 000 | Delay (in seconds) before the alarm is activated once the current analog value rises above the setpoint. The time delay is reset when the current value of the analog signal drops below the setpoint less the deadband. |
| 49 | Aln 2 Zero | Analog Input 2 Zero Adjustment | 000 | See Details for analog input 1. |
| 50 | Aln 2 Full Scale | Analog Input 2 Full Scale Adjustment | 0000 | |
| 51 | Aln 2 Range | Analog Input 2 Range | 0000 | |
| 52 | Aln 2 Lo SP | Analog Input 2 Low Setpoint | 000.0 | |
| 53 | Aln 2 Lo DB | Analog Input 2 Low Deadband | 000.0 | |
| 54 | Aln 2 Lo TD | Analog Input 2 Low Time Delay | 000 | |
| 55 | Aln 2 Hi SP | Analog Input 2 High Setpoint | 000.0 | |
| 56 | Aln 2 Hi DB | Analog Input 2 High Deadband | 000.0 | |
| 57 | Aln 2 Hi TD | Analog Input 2 High Time Delay | 000 | See Details for analog input 1. |
| 58 | Aln 3 Zero | Analog Input 1 Zero Adjustment | 000 | |
| 59 | Aln 3 Full Scale | Analog Input 1 Full Scale Adjustment | 0000 | |
| 60 | Aln 3 Range | Analog Input 1 Range | 0000 | |

TABLE 6-continued

Fluid Treatment Apparatus Settings

| Index | Abbreviation | Full Name | Format | Details |
|---|---|---|---|---|
| 61 | Aln 3 Lo SP | Analog Input 1 Low Setpoint | 000.0 | |
| 62 | Aln 3 Lo DB | Analog Input 1 Low Deadband | 000.0 | |
| 63 | Aln 3 Lo TD | Analog Input 1 Low Time Delay | 000 | |
| 64 | Aln 3 Hi SP | Analog Input 1 High Setpoint | 000.0 | |
| 65 | Aln 3 Hi DB | Analog Input 1 High Deadband | 000.0 | |
| 66 | Aln 3 Hi TD | Analog Input 1 High Time Delay | 000 | |
| 67 | Aln 4 Zero | Analog Input 4 Zero Adjustment | 000 | See Details for analog input 1. |
| 68 | Aln 4 Full Scale | Analog Input 4 Full Scale Adjustment | 0000 | |
| 69 | Aln 4 Range | Analog Input 4 Range | 0000 | |
| 70 | Aln 4 Lo SP | Analog Input 4 Low Setpoint | 000.0 | |
| 71 | Aln 4 Lo DB | Analog Input 4 Low Deadband | 000.0 | |
| 72 | Aln 4 Lo TD | Analog Input 4 Low Time Delay | 000 | |
| 73 | Aln 4 Hi SP | Analog Input 4 High Setpoint | 000.0 | |
| 74 | Aln 4 Hi DB | Analog Input 4 High Deadband | 000.0 | |
| 75 | Aln 4 Hi TD | Analog Input 4 High Time Delay | 000 | |
| 76 | PLC ADR 1 WRITE | PLC Address 1 Write | 00000 | Beginning address for the first block of memory being written to the PLC by the In the case of Koyo PLCs, this is the beginning address of the block of words written (default = V2000 or 1024 decimal). In the case of A–B PLCs, this is the beginning address of the block of words written (default = 0). Do not make changes to this setting if communication to the PLC is enabled. |
| 77 | PLC ADR 2 WRITE | PLC Address 2 Write | 00000 | Beginning address for the second block of memory being written to the PLC by the fluid treatment apparatus via Direct Net (Koyo) protocol. These are the bits written to the Koyo PLCs. The default value for the beginning address is C20 (or 16769 decimal). This setting is not used for A–B PLCs. Do not make changes to this setting if communication to the PLC is enabled. |
| 78 | PLC ADR 3 READ | PLC Address 3 Read | 00000 | Beginning address for the first block of memory being read the PLC by the apparatus. In the case of Koyo PLCs, this is the beginning address of the block of bits read (default = C60 or 16771 decimal). In the case of A–B PLCs, this is the beginning address of the block of words read (default = 34). Do not make changes to this selling if communication to the PLC is enabled. |
| 79 | PLC ADR 4 READ | PLC Address 4 Read | 00000 | Beginning address for the second block of memory being read from the PLC by the fluid treatment apparatus via Direct Net (Koyo) protocol. These are the words read from the Koyo PLCs. The default value for the beginning address is V2040 (or 1056 decimal). This setting is not used for A–B PLCs. Do not make changes to this setting if communication to the PLC is enabled. |
| 80 | Feed CND Standard | Feed Conductivity Standard | 000 | With these settings, the operator can calibrate the conductivity inputs to a standard solution. Use of this setting automatically |
| 81 | Perm CND Standard | Permeate Conductivity Standard | 00.0 | changes the cell constant for the conductivity input being calibrated. See the User Manual section on Calibration for more information. |
| 82 | PLC Com 0 = OFF 1 = Koyo 2 = A–B | PLC Communication | 0 | Turns the PLC communication off and selects communication protocol. |
| 83 | Permeate Divert | Permeate Diversion Setpoint | 00.0 | These settings work in the same fashion as the high permeate conductivity settings. They are |
| 84 | Permeate Diversion DB | Permeate Diversion Deadband | 00.0 | used to control a permeate diversion function in the PLC. Permeate diversion is not logged |
| 85 | Permeate Diversion TD | Permeate Diversion Time Delay | 000 | as an alarm in the fluid treatment apparatus. |

Figure 31D:
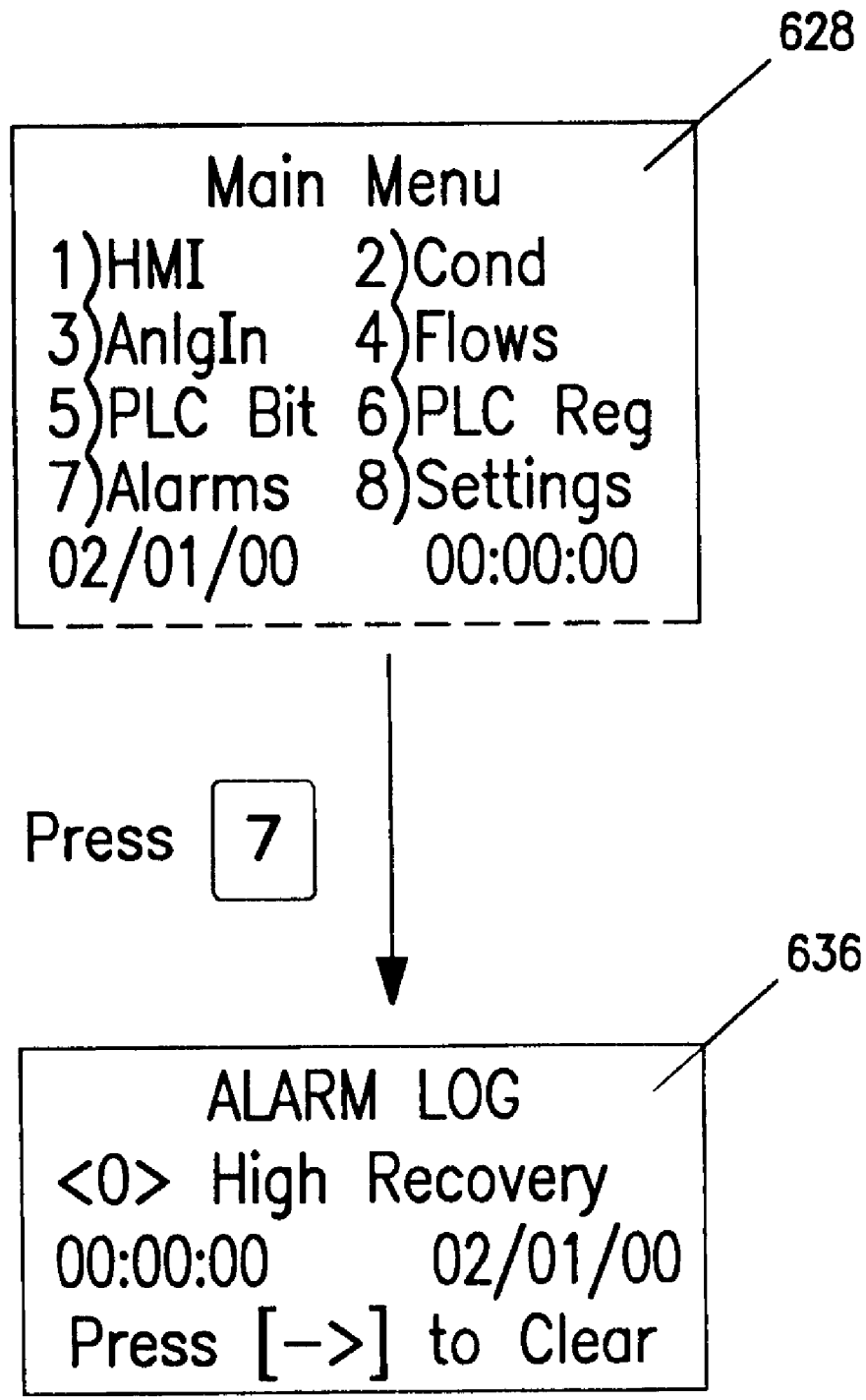
FIG. 31d shows the alarm log screen of the second embodiment of the present invention.

Apparatus 600 automatically logs the time and date of all alarms. These may be viewed in the alarm log screens 636 which are accessible from main menu 628 as shown in FIG. 31d. The up/down arrow keys are used to scroll through logged alarms. Pressing the right arrow key will clear the alarm log. Apparatus 600 is also programmed to activate a number of alarms based upon the monitored parameters. Activation of these alarms results in a PLC bit being set to a "1" state. The alarm is logged in the apparatus alarm log along with the time and date. The alarms are listed below in Table 7.

TABLE 7

Fluid Treatment Apparatus Alarms

| | |
|---|---|
| Low Salt Rejection Alarm | Analog Input 1 High Alarm |
| High Recovery Alarm | Analog Input 2 Low Alarm |
| Low Reject Flow Alarm | Analog Input 2 High Alarm |
| High Permeate Conductivity Alarm | Analog Input 3 Low Alarm |
| High Feed Conductivity Alarm | Analog Input 3 High Alarm |
| High Feed Temperature Alarm | Analog Input 4 Low Alarm |
| Low Feed Temperature Alarm | Analog Input 4 High Alarm |
| Analog Input 1 Low Alarm | PLC Communication Alarm |

In addition to logging its own alarms, apparatus 600 logs the occurrence of alarms in the PLC. Twelve bits in the PLC are read by the apparatus and whenever one of these bits switches to the "1" state an alarm is logged. Names for these PLC alarms can be customized in the configuration software.

Figure 32A:
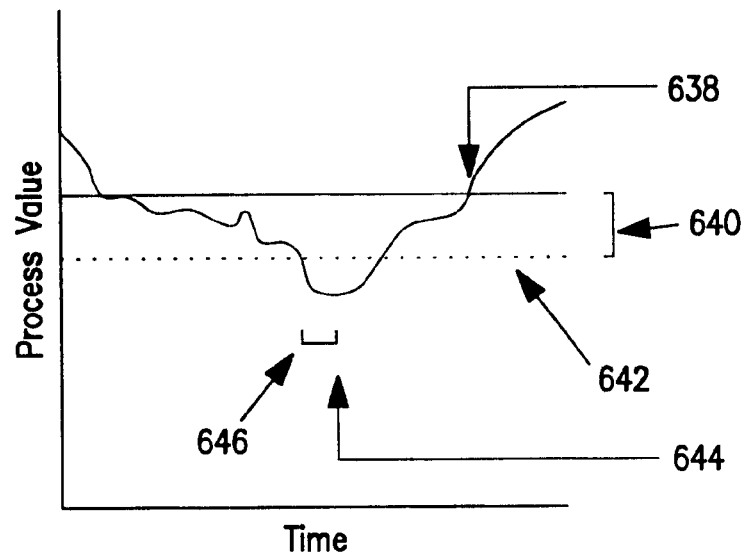
FIGS. 32a–b are graphs depicting the time delays and deadbands used to control the alarm outputs of the second embodiment of the present invention.
Figure 32B:
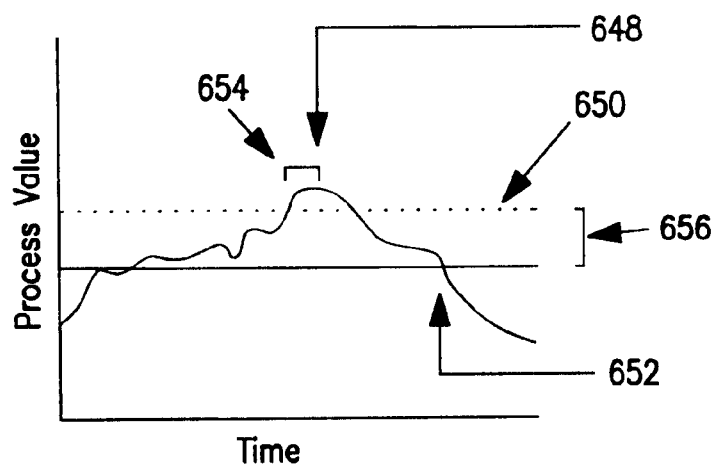

Turning to FIGS. 32a–b, time delays and deadbands are shown that are used to control the action of the alarm outputs (bits written to the PLC). The illustration in FIG. 32a shows the action of a low alarm setpoint on a falling value. The deadband is shown at 640. The low alarm setpoint is shown by the dashed line at 642. A time delay is shown at 646, and an alarm is activated at the end of the time delay 644. The alarm is released when the rising process value exceeds the setpoint added to the deadband; see 638. Turning to FIG. 32b, the high alarm setpoint 650 works in the same manner except that the deadband 656 is below the setpoint 650. The time delay is shown at 654 and the alarm is activated at the end of the time delay 648. The alarm is released when the rising process value drops below the setpoint minus the deadband 652.

Data Logging

The fluid treatment apparatus 600 automatically logs operating data in its internal solid state memory. Access to the data is gained by use of specialized software. The software is a PC based software package that allows the data to be retrieved either locally (via external serial connector 614 shown in FIG. 28) or remotely (via modem 622 shown on FIG. 29).

The fluid treatment apparatus logs the data points described in Table 8.

TABLE 8

Data Points Logged by Fluid Treatment Apparatus

| | | |
|---|---|---|
| Feed Conductivity | Analog Input 1 | PLC Register 6 |
| Permeate Conductivity | Analog Input 2 | PLC Register 7 |
| Feed Temperature | Analog Input 3 | PLC Register 8 |
| Permeate Temperature | Analog Input 4 | PLC Register 9 |
| % Salt Rejection | PLC Register 1 | PLC Register 10 |
| Permeate Flow | PLC Register 2 | PLC Register 11 |
| Reject Flow | PLC Register 3 | PLC Register 12 |
| Auxiliary Flow | PLC Register 4 | PLC Register 13 |
| % Recovery | PLC Register 5 | PLC Register 14 |
| | | PLC Register 15 |

The fluid treatment apparatus uses a unique method to compress data as the data gets older. This method of data compression is specifically for RO applications where long term data logging is necessary, but numerous data points are not necessarily an advantage.

Figure 34:
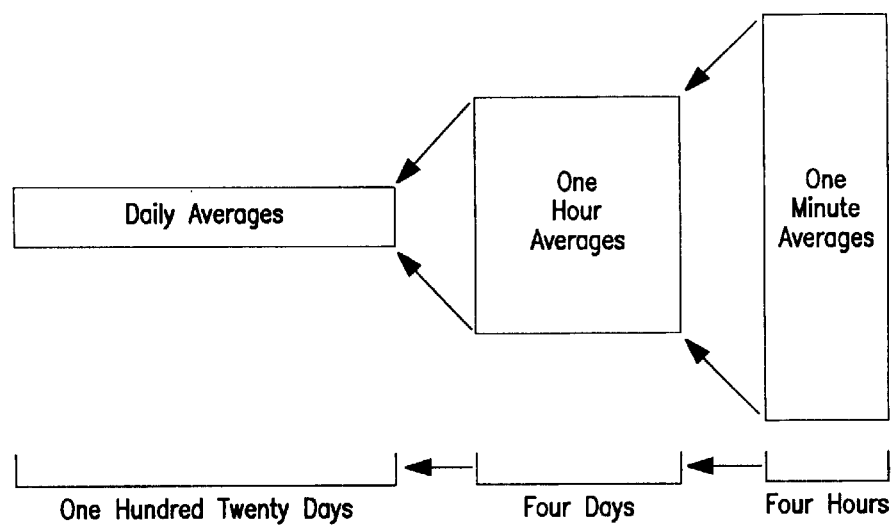
FIG. 34 is a diagram demonstrating the data logging and data compression feature of the present invention.

The data displayed in real time on the fluid treatment apparatus display 610, shown on FIG. 28, is an average of five scans made of the apparatus inputs every second. For the last four hours of operation measured backward from any given point in time, this data is logged as one minute averages, i.e., an average of sixty of the one second averages displayed on display 610. For the four days preceding these four hours, the data is compressed into hourly averages. For the one hundred twenty days preceding these four days, the data is compressed into daily averages. See FIG. 34. While particular quantities of days, hours, and minutes are provided, the invention is not to be limited to these exact quantities and this will apparent to those skilled in the art.

The data logger is activated by a single bit from the PLC as shown in Table 10. When this bit is high, data logging is enabled. When the data logger is not enabled, data scanned by apparatus 600 is still displayed in real time on display 610; however, it is not incorporated into the data averaging function as described above. This allows the user to control apparatus 600 in such a way that only valid data is included in the data compression routine.

PLC Overview

Programmable logic controllers (PLCs) are microprocessor-based devices that were designed to replace relay-based control systems. PLCs consist of three general parts: the input interface, the central processing unit (CPU), and the output interface. The CPU of the PLC consists of a microprocessor and an array of solid state memory often called the data table. All numbers are stored as combinations of "1"s ("highs") and "0"s ("lows") in the PLC. Therefore, each position of the data table contains either a "1" or a "0".

As the PLC operates, it repeatedly scans its inputs, performs the control functions programmed into its CPU, and writes the results to its outputs. The inputs and the outputs are connected to the data table by means of the input and output interface.

The interface is necessary to condition the relatively large voltages connected to the input terminals. Output signals must also be conditioned to provide the types of signals necessary to illuminate indicator lights, activate motor starters, or accomplish any of the other functions necessary for control outputs. As the inputs connected to the PLC change, their associated bits in the data table also change. As the processor scans the input portion of the data table, it recognizes these changes.

Depending upon the logic programmed into the microprocessor, the PLC will make decisions based upon the data in the data table. After executing its decision making process, it will change the bit states in the output portion of the data table.

PLCs use a specialized programming format called ladder logic. The ladder logic diagram which illustrates a PLC program is very similar to that used by electricians to illustrate electrical wiring diagrams. In the case of a wiring diagram, the ladder describes the contacts and coils of relays. In PLCs, the ladder describes the state of the bits in the PLC data table.

The bits illustrated by the ladder logic diagram can be of several types. They may be associated with a hard-wired input or a hard-wired output. They may also be an internal memory bit which is not directly associated with an input or output. By using these internal bits, PLCs can perform more complicated functions with greater flexibility.

Figure 33:
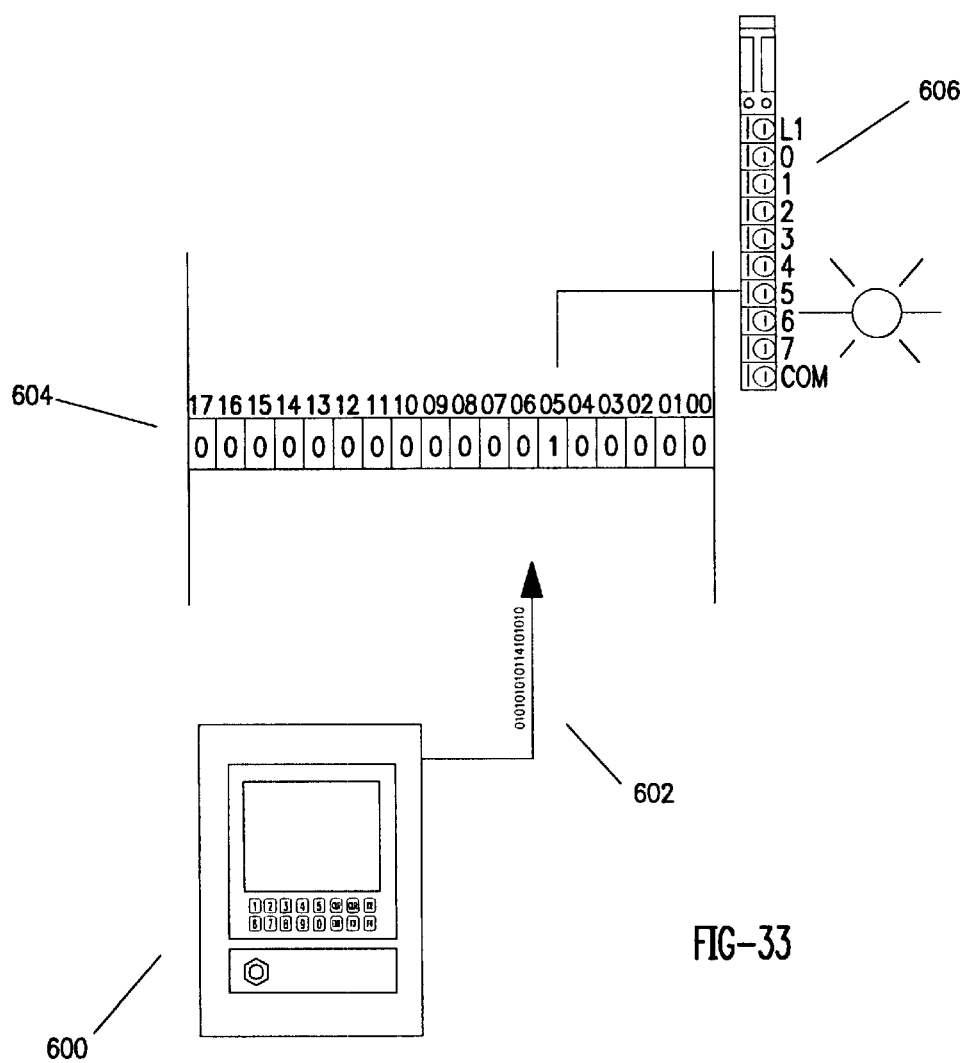
FIG. 33 is a diagram demonstrating direct serial communication between the second embodiment of the present invention and a programmable logic controller.

Instead of being connected to the input and output terminals of the PLC, apparatus 600 is connected directly to the PLC's microprocessor via serial connection 602, as described with respect to FIG. 27. This allows apparatus 600 to communicate directly to the microprocessor of PLC 414. By doing this, apparatus 600 can tell PLC 414 to change the states of internal memory bits, and recognize when bits have been changed, without having to be physically connected to the inputs and outputs of PLC 414. FIG. 33 shows apparatus 600 communicating via serial connection 602 with PLC 414 with ladder logic, using internal memory register 604 of PLC 414 and PLC terminal strip 606 at which filed devices are physically connected.

Apparatus 600 is configured with the PLC memory locations (addresses) which allows it to read and write data to the correct locations. The addresses configured into apparatus 600 are then used in the PLC logic program. If PLC 414 is being programmed for a new application, these addresses are simply used directly in the PLC logic. If apparatus 600 is being used with a PLC having an existing program, then "move" instructions are used to move data, within the PLC, to and from the proper addresses being used by apparatus 600.

In the case of Automation Direct™ PLCs, manufactured by Koyo, two blocks of data are written to the PLC and two blocks are read from the PLC. Of the two blocks written, one is in the form of discrete bits and the other is in the form of sixteen bit words. The same is true for the two blocks read from the PLC. The starting address of each of these four blocks is configured into apparatus 600 via the appropriate settings data entry screen as described in FIG. 31c.

In the case of PLCs such as those manufactured by Allen-Bradley, one block of data is written to the PLC in the form of sixteen bit words and one block of data is read from the PLC in the form of sixteen bit words. The starting address of each of these two blocks is configured into apparatus 600 via the appropriate settings data entry screen. In this type of PLC, the memory written and read is part of the PLC's common interface file (CIF). The individual bits used by apparatus 600, for example, alarm indicators, are read and written as part of the sixteen bit word.

Tables 9, 10, 11, and 12 describe the addressing used for the data written to and read from the PLC by apparatus 600. Both the Koyo and Allen-Bradley (A–B) PLCs are described.

TABLE 9

Bits Written to PLC

| Koyo PLCs | | A-B PLCs[1] | | | |
|---|---|---|---|---|---|
| Bit Written to PLC | Default Address | Bit Written to PLC | Default Address | Description | Purpose |
| b + 0 | C20 | w + 0/00 | N9:0/00 | Low Salt Rejection Alarm | The fluid treatment apparatus sets the bits in these locations when the appropriate alarm occurs. |
| b + 1 | C21 | w + 0/01 | N9:0/01 | High Recovery Alarm | |
| b + 2 | C22 | w + 0/02 | N9:0/02 | Low Reject Flow Alarm | |
| b + 3 | C23 | w + 0/03 | N9:0/03 | High Permeate Conductivity Alarm | |
| b + 4 | C24 | w + 0/04 | N9:0/04 | High Feed Conductivity Alarm | |
| b + 5 | C25 | w + 0/05 | N9:0/05 | High Feed Temperature Alarm | |
| b + 6 | C26 | w + 0/06 | N9:0/06 | Low Feed Temperature Alarm | |
| b + 7 | C27 | w + 0/07 | N9:0/07 | Analog Input 1 Low Alarm | |
| b + 8 | C30 | w + 0/08 | N9:0/08 | Analog Input 1 High Alarm | |
| b + 9 | C31 | w + 0/09 | N9:0/09 | Analog Input 2 Low Alarm | |
| b + 10 | C32 | w + 0/10 | N9:0/10 | Analog Input 2 High Alarm | |
| b + 11 | C33 | w + 0/11 | N9:0/11 | Analog Input 3 Low Alarm | |
| b + 12 | C34 | w + 0/12 | N9:0/12 | Analog Input 3 High Alarm | |
| b + 13 | C35 | w + 0/13 | N9:0/13 | Analog Input 4 Low Alarm | |
| b + 14 | C36 | w + 0/14 | N9:0/14 | Analog Input 4 High Alarm | |
| b + 15 | C37 | w + 0/15 | N9:0/15 | PLC Communication Alarm | This bit gets set when PLC communication problems occur. |
| b + 16 | C40 | w + 1/00 | N9:1/00 | Selector Switch 1 Hand | Each selector switch has three positions, "Hand", "Off", and "Auto". In the "Hand" and "Auto" positions, the bits are set in these locations |
| b + 17 | C41 | w + 1/01 | N9:1/01 | Selector Switch 1 Auto | |
| b + 18 | C42 | w + 1/02 | N9:1/02 | Selector Switch 2 Hand | |
| b + 19 | C43 | w + 1/03 | N9:1/03 | Selector Switch 2 Auto | |
| b + 20 | C44 | w + 1/04 | N9:1/04 | Selector Switch 3 Hand | |
| b + 21 | C45 | w + 1/05 | N9:1/05 | Selector Switch 3 Auto | |
| b + 22 | C46 | w + 1/06 | N9:1/06 | Momentary Push Button 1 | These bits are set only while the key is depressed. |
| b + 23 | C47 | w + 1/07 | N9:1/07 | Momentary Push Button 2 | |
| b + 24 | C50 | w + 1/08 | N9:1/08 | Momentary Push Button 3 | |

TABLE 9-continued

Bits Written to PLC

| Koyo PLCs | | A-B PLCs[1] | | | |
|---|---|---|---|---|---|
| Bit Written to PLC | Default Address | Bit Written to PLC | Default Address | Description | Purpose |
| b + 25 | C51 | w + 1/09 | N9:1/09 | One Second Flip-Flop | The repeated flip-flop of this bit allows the PLC to determine if communication with the Fluid treatment apparatus has been interrupted. |
| b + 26 | C52 | w + 1/10 | N9:1/10 | Permeate Diversion | This bit is set when the permeate conductivity diversion setpoint is exceeded. |
| b + 27 | C53 | w + 1/11 | N9:1/11 | Not Used | |
| b + 28 | C54 | w + 1/12 | N9:1/12 | Not Used | |
| b + 29 | C55 | w + 1/13 | N9:1/13 | Not Used | |
| b + 30 | C56 | w + 1/14 | N9:1/14 | Not Used | |
| b + 31 | C57 | w + 1/15 | N9:1/15 | Not Used | |

[1]The Common Interface File is N9 for the A-B MicroLogix 1500 and SLC processors and N7 for the MicroLogix 1000 processor.

TABLE 10

Bits Read From PLC

| Koyo PLCs | | A-B PLCs[1] | | | |
|---|---|---|---|---|---|
| Bit Read from PLC | Default Address | Bit Read from PLC | Default Address | Description | Purpose |
| b + 0 | C60 | w + 0/00 | N9:34100 | Low Salt Rejection Alarm Enable | When the PLC sets these bits, the appropriate Fluid treatment apparatus alarms are enabled. |
| b + 1 | C61 | w + 0/01 | N9:34/01 | High Recovery Alarm Enable | |
| b + 2 | C62 | w + 0/02 | N9:34/02 | Low Reject Flow Alarm Enable | |
| b + 3 | C63 | w + 0/03 | N9:34/03 | High Permeate Cond Alarm Enable | |
| b + 4 | C64 | w + 0/04 | N9:34/04 | High Feed Cond Alarm Enable | |
| b + 5 | C65 | w + 0/05 | N9:34/05 | High Feed Temp Alarm Enable | |
| b + 6 | C66 | w + 0/06 | N9:34/06 | Low Feed Temp Alarm Enable | |
| b + 7 | C67 | w + 0/07 | N9:34/07 | Analog Input 1 High and Low Alarm Enable | These PLC bits enable both the high and low alarms for each analog input. |
| b + 8 | C70 | w + 0/08 | N9:34/08 | Analog Input 2 High and Low Alarm Enable | |
| b + 9 | C71 | w + 0/09 | N9:34/09 | Analog Input 3 High and Low Alarm Enable | |
| b + 10 | C72 | w + 0/10 | N9:34110 | Analog Input 4 High and Low Alarm Enable | |
| b + 11 | C73 | w + 0/11 | N9:34/11 | Data Logger Enable | This bit allows the PLC to enable the Fluid treatment apparatus data logger. |
| b + 12 | C74 | w + 0/12 | N9:34/12 | Run Time Totalizer Enable | This bit allows the PLC to enable the Fluid treatment apparatus run time totalizer. |
| b + 13 | C75 | w + 0/13 | N9:34/13 | Permeate Totalizer Enable | This bit allows the PLC to enable the |

TABLE 10-continued

Bits Read From PLC

| Koyo PLCs | | A-B PLCs[1] | | | |
|---|---|---|---|---|---|
| Bit Read from PLC | Default Address | Bit Read from PLC | Default Address | Description | Purpose |
| b + 14 | C76 | w + 0114 | N9:34/14 | Permeate Diversion Enable | Fluid treatment apparatus permeate flow totalizer. This bit allows the PLC to enable the Fluid treatment apparatus permeate diversion control. |
| b + 15 | C77 | w + 0115 | N9:34/15 | Blinks LCD Backlight | This bit blinks the backlight to signal an alarm condition. |
| b + 16 | C100 | w + 1/00 | N9:35/00 | PLC Alarm Bit 1 | When the PLC sets |
| b + 17 | C101 | w + 1/01 | N9:35/01 | PLC Alarm Bit 2 | each of these bits, |
| b + 18 | C102 | w + 1/02 | N9:35/02 | PLC Alarm Bit 3 | an alarm is logged |
| b + 19 | C103 | w + 1/03 | N9:35/03 | PLC Alarm Bit 4 | by the Fluid |
| b + 20 | C104 | w + 1/04 | N9:35/04 | PLC Alarm Bit 5 | treatment |
| b + 21 | C105 | w + 1/05 | N9:35/05 | PLC Alarm Bit 6 | apparatus. Each |
| b + 22 | C106 | w + 1/06 | N9:35/06 | PLC Alarm Bit 7 | alarm bit may be |
| b + 23 | C107 | w + 1/07 | N9:35/07 | PLC Alarm Bit 8 | given a unique name in the Fluid treatment apparatus configuration. |
| b + 24 | C110 | w + 1/08 | N9:35/08 | Indicator Message 1 | These PLC bits |
| b + 25 | C111 | w + 1/09 | N9:35/09 | Indicator Message 2 | control the indicator |
| b + 26 | C112 | w + 1/10 | N9:35/10 | Indicator Message 3 | messages on the |
| b + 27 | C113 | w + 1/11 | N9:35/11 | Indicator Message 4 | front of the Fluid |
| b + 28 | C114 | w + 1/12 | N9:35/12 | Indicator Message 5 | treatment |
| b + 29 | C115 | w + 1/13 | N9:35/13 | Indicator Message 6 | apparatus. |
| b + 30 | C116 | w + 1/14 | N9:35/14 | Indicator Message 7 | |
| b + 31 | C117 | w + 1/15 | N9:35/15 | Indicator Message 8 | |
| b + 32 | C120 | w + 2/00 | N9:36/00 | PLC Bit Status 1 | The Fluid treatment |
| b + 33 | C121 | w + 2/01 | N9:36/01 | PLC Bit Status 2 | apparatus displays |
| b + 34 | C122 | w + 2/02 | N9:36/02 | PLC Bit Status 3 | the status of each |
| b + 35 | C123 | w + 2/03 | N9:36/03 | PLC Bit Status 4 | of these PLC bits |
| b + 36 | C124 | w + 2/04 | N9:36/04 | PLC Bit Status 5 | thus allowing the |
| b + 37 | C125 | w + 2/05 | N9:36/05 | PLC Bit Status 6 | operator to have |
| b + 38 | C126 | w + 2/06 | N9:36/06 | PLC Bit Status 7 | some indication of |
| b + 39 | C127 | w + 2/07 | N9:36/07 | PLC Bit Status 8 | the internal |
| b + 40 | C130 | w + 2/08 | N9:36/08 | PLC Bit Status 9 | workings of the PLC |
| b + 41 | C131 | w + 2/09 | N9:36/09 | PLC Bit Status 10 | program. Each bit |
| b + 42 | C132 | w + 2/10 | N9:36/10 | PLC Bit Status 11 | may be given a |
| b + 43 | C133 | w + 2/11 | N9:36/11 | PLC Bit Status 12 | unique name in the Fluid treatment apparatus configuration. |
| b + 44 | | w + 2/12 | N9:36/12 | | |
| — | — | — | — | Not Used | |
| b + 63 | | w + 3/15 | N9:37/15 | | |

[1]The Common Interface File is N9 for the A-B MicroLogix 1500 and SLC processors and N7 for the MicroLogix 1000 processor.

TABLE 11

Words Written to PLC

| Koyo PLCs | | A-B PLCs[1] | | | |
|---|---|---|---|---|---|
| Word Written to PLC | Default Address | Word Written to PLC | Default Address | Description | Purpose |
| w + 0 | V2000 | w + 2 | N9:2 | PLC Preset 1 | The Fluid |
| w + 1 | V2001 | w + 3 | N9:3 | PLC Preset 2 | treatment |
| w + 2 | V2002 | w + 4 | N9:4 | PLC Preset 3 | apparatus |
| w + 3 | V2003 | w + 5 | N9:5 | PLC Preset 4 | can be used |
| w + 4 | V2004 | w + 6 | N9:6 | PLC Preset 5 | to write |
| w + 5 | V2005 | w + 7 | N9:7 | PLC Preset 6 | values to 16 |
| w + 6 | V2006 | w + 8 | N9:8 | PLC Preset 7 | bit word |
| w + 7 | V2007 | w + 9 | N9:9 | PLC Preset 8 | registers of |
| w + 8 | V2010 | w + 10 | N9:10 | PLC Preset 9 | the PLC. |

TABLE 11-continued

Words Written to PLC

| Koyo PLCs | | A-B PLCs[1] | | | |
|---|---|---|---|---|---|
| Word Written to PLC | Default Address | Word Written to PLC | Default Address | Description | Purpose |
| w + 9 | V2011 | w + 11 | N9:11 | PLC Preset 10 | These values are entered by the operator via the Fluid treatment apparatus keypad. |
| w + 10 | V2012 | w + 12 | N9:12 | PLC Preset 11 | |
| w + 11 | V2013 | w + 13 | N9:13 | PLC Preset 12 | |
| w + 12 | V2014 | w + 14 | N9:14 | Fluid treatment apparatus Real Time Clock Hours (0–23) | Real time clock data is written to these PLC registers. |
| w + 13 | V2015 | w + 15 | N9:15 | Fluid treatment apparatus Real Time Clock Min (0–59) | |
| w + 14 | V2016 | w + 16 | N9:16 | Fluid treatment apparatus Real Time Clock Sec (0–59) | |
| w + 15 | V2017 | w + 17 | N9:17 | Fluid treatment apparatus Real Time Clock Date (1–31) | |
| w + 16 | V2020 | w + 18 | N9:18 | Fluid treatment apparatus Real Time Clock Month (1–12) | |
| w + 17 | V2021 | w + 19 | N9:19 | Fluid treatment apparatus Real Time Clock Year | |
| w + 18 | V2022 | w + 20 | N9:20 | Feed Conductivity | Analog data monitored by the Fluid treatment apparatus is written to these PLC memory locations. Multipliers (e.g., × 10) are used to convert floating point values to integers. |
| w + 19 | V2023 | w + 21 | N9:21 | Feed Temperature (Deg C × 10) | |
| w + 20 | V2024 | w + 22 | N9:22 | Permeate Conductivity × 10) | |
| w + 21 | V2025 | w + 23 | N9:23 | Salt Rejection (× 10) | |
| w + 22 | V2026 | w + 24 | N9:24 | Permeate Flow (× 10) | |
| w + 23 | V2027 | w + 25 | N9:25 | Reject Flow (× 10) | |
| w + 24 | V2030 | w + 26 | N9:26 | Auxiliary Flow (× 10) | |
| w + 25 | V2031 | w + 27 | N9:27 | % Recovery (× 10) | |
| w + 26 | V2032 | w + 28 | N9:28 | Analog Input 1 (× 10) | |
| w + 27 | V2033 | w + 29 | N9:29 | Analog Input 2 (× 10) | |
| w + 28 | V2034 | w + 30 | N9:30 | Analog Input 3 (× 10) | |
| w + 29 | V2035 | w + 31 | N9:31 | Analog Input 4 (× 10) | |
| w + 30 | V2036 | w + 32 | N9:32 | Run Time (× 1000 hrs) (0–9999) | |
| w + 31 | V2037 | w + 33 | N9:33 | Permeate Total (× 1000 gal) (0–9999) | |

[1]The Common Interface File is N9 for the A-B MicroLogix 1500 and SLC processors and N7 for the MicroLogix 1000 processor.

TABLE 12

Words Read from PLC

| Koyo PLCs | | A–B PLCs[1] | | | |
|---|---|---|---|---|---|
| Word Read from PLC | Default Address | Word Read from PLC | Default Address | Description | Purpose |
| w + 0 | V2040 | w + 4 | N9:38 | PLC Register 1 | These 16 bit words are read and displayed by the Fluid treatment apparatus as integers. They are also logged by the Fluid treatment apparatus data logger. |
| w + 1 | V2041 | w + 5 | N9:39 | PLC Register 2 | |
| w + 2 | V2042 | w + 6 | N9:40 | PLC Register 3 | |
| w + 3 | V2043 | w + 7 | N9:41 | PLC Register 4 | |
| w + 4 | V2044 | w + 8 | N9:42 | PLC Register 5 | |
| w + 5 | V2045 | w + 9 | N9:43 | PLC Register 6 | |
| w + 6 | V2046 | w + 10 | N9:44 | PLC Register 7 | |
| w + 7 | V2047 | w + 11 | N9:45 | PLC Register 8 | |
| w + 8 | V2050 | w + 12 | N9:46 | PLC Register 9 | |
| w + 9 | V2051 | w + 13 | N9:47 | PLC Register 10 | |
| w + 10 | V2052 | w + 14 | N9:48 | PLC Register 11 | |
| w + 11 | V2053 | w + 15 | N9:49 | PLC Register 12 | |
| w + 12 | V2054 | w + 16 | N9:50 | PLC Register 13 | |
| w + 13 | V2055 | w + 17 | N9:51 | PLC Register 14 | |
| w + 14 | V2056 | w + 18 | N9:52 | PLC Register 15 | |
| w + 15 | V2057 | w + 19 | N9:53 | Not Used | |

[1]The Common Interface File is N9 for the A–B MicroLogix 1500 and SLC processors and N7 for the MicroLogix 1000 processor.

EXAMPLE

Changing Allen-Bradley and Koyo PLC Addressing

In the case of Allen-Bradley PLCs, the fluid treatment apparatus reads and writes data to the PLC's common interface file (CIF). In MicroLogix 1500 PLCs and SLCs, this is the N9 file. The default starting address for the block written to the PLC is N9:0. The default starting address for the block being read from the PLC is N9:34. Changing these addresses in the fluid treatment apparatus settings menu (Index Nos. 76 and 78) is simply a matter of entering a number other than "0" for the block being written and "34" for the block being read. Changing the starting address of each block moves all of the successive addresses in that block relative to the starting address.

In the case of Koyo PLCs, the fluid treatment apparatus reads two blocks of data and writes two blocks of data. Each of these starting addresses may be configured in the fluid treatment apparatus settings menu (Index Nos. 76–79). Koyo PLCs use an absolute addressing system for all of the memory locations in the PLC. Before entering a different starting address for a memory location being read from or written to by the fluid treatment apparatus, it will be necessary to convert the octal numbering system used by the Koyo to a decimal number used by the fluid treatment apparatus.

When changing the PLC memory locations, the user is to be sure that the fluid treatment apparatus will not be writing over important data in the PLC. Changing the starting address changes all of the successive addresses in the block being read or written.

Furthermore, the serial port on the PLC must be configured properly before communication with the fluid treatment apparatus can occur. The proper port configurations are listed below in Table 13. The port configuration necessary for fluid treatment apparatus communication may differ from the default configuration supplied by the PLC manufacturer.

TABLE 13

PLC Communication Port Configuration

| Parameter | Koyo PLCs | Parameter | A-B PLCs |
|---|---|---|---|
| Protocol | DeviceNet | Protocol | DF1, Full Duplex |
| Time-Out | 800 ms | Baud Rate | 9600 |
| RTS On Delay | 0 ms | Parity | None |
| RTS Off Delay | 0 ms | Data Bits | 8 |
| Baud Rate | 9600 | Stop Bit | 1 |
| Stop Bits | 1 | Error Checking | CRC |
| Parity | None | | |
| Format | Hex | | |

Figure 35A:
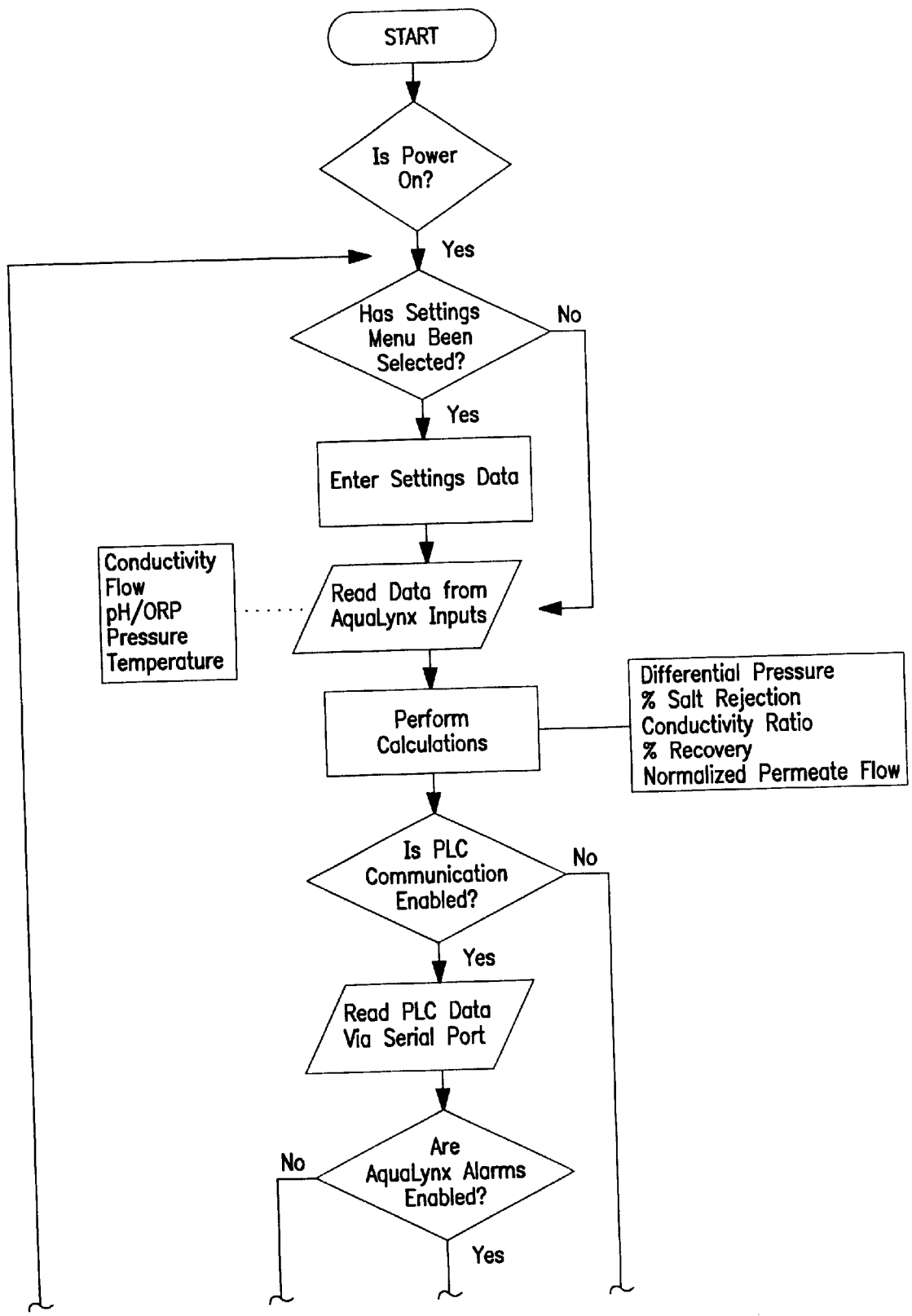
FIG. 35 is a flow diagram showing the operation of the second embodiment of the present invention.
Figure 35B:
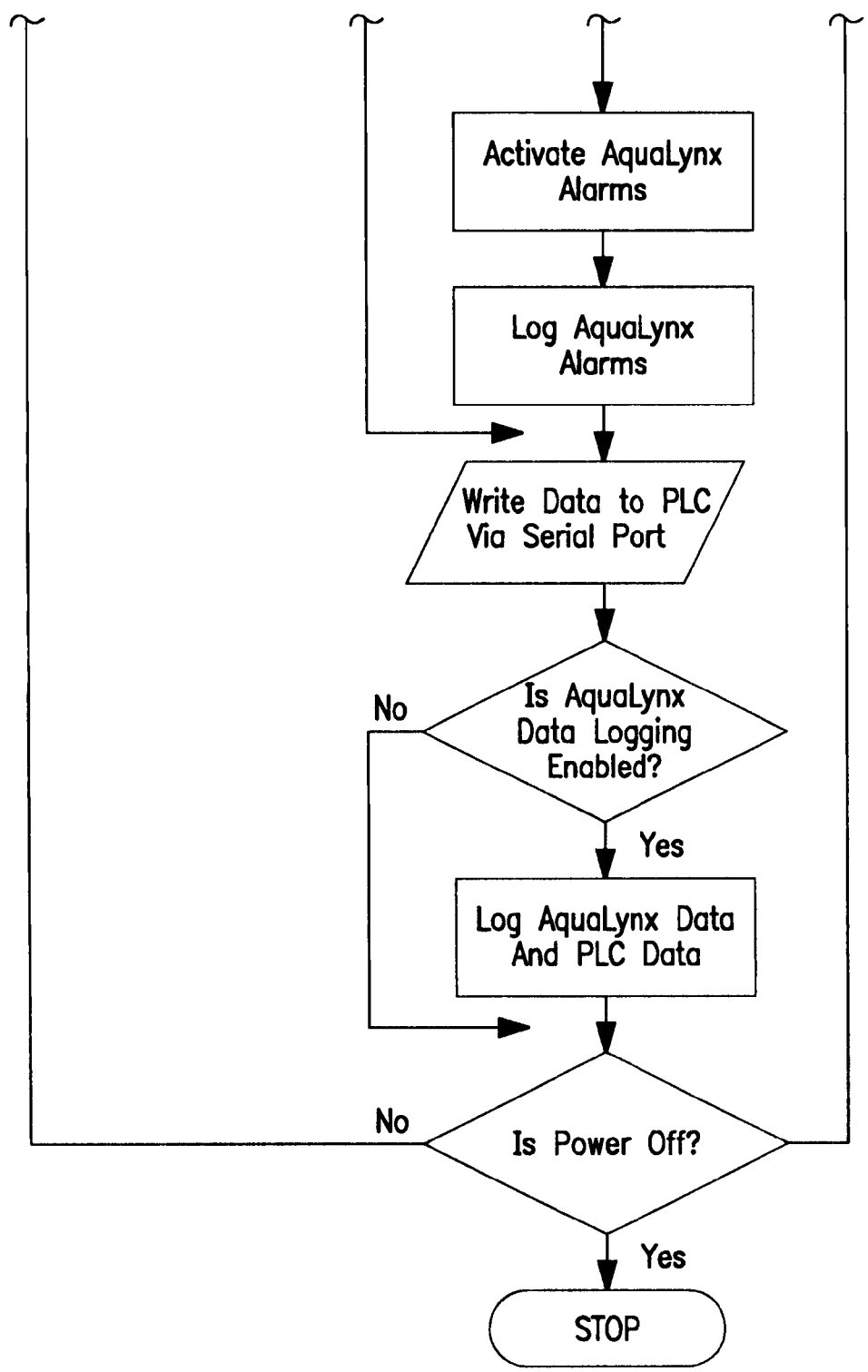

Attention is now turned to FIG. 35 which is a flow diagram showing the operation of the second embodiment of the fluid treatment apparatus 600. This diagram demonstrates the flow of operation through entering settings data to reading inputs into the apparatus and communication with a PLC. Alarms and data logging can be enabled according to user preference. Examples of inputs and types of calculations that can be performed are also shown.

Figure 36B:
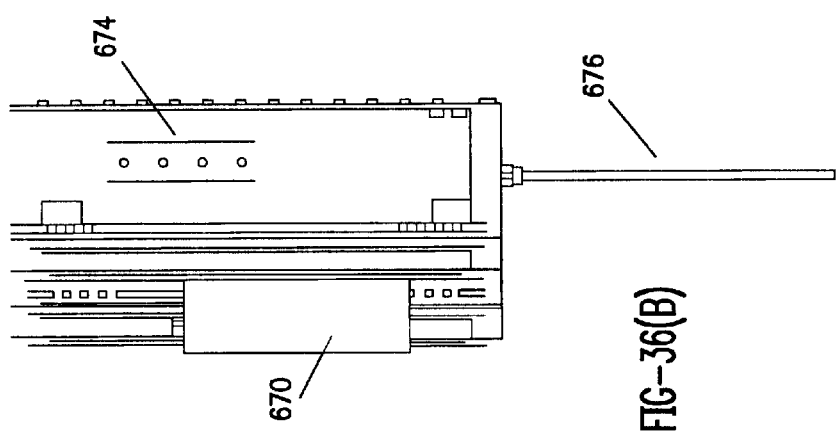
FIG. 36 shows the apparatus of the second embodiment of the present invention having integral sensors.
Figure 36A:
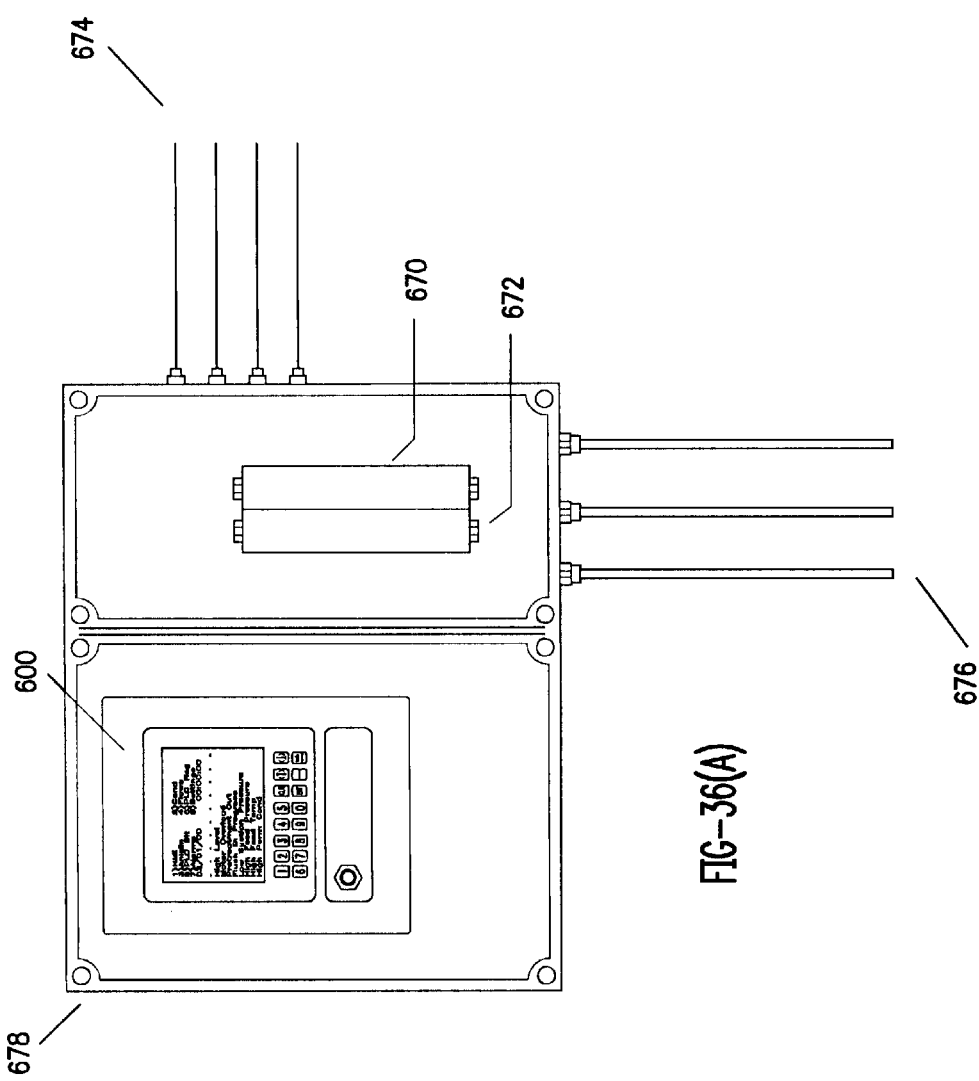

FIGS. 36a and 36b show a front and side view respectively of fluid treatment apparatus 600 with integral sensor manifolds 670 and 672. Fluid treatment apparatus 600 and sensor manifolds 670 and 672 are in close proximity and housed in housing 678 so that the user has efficient access to both concurrently. The integral sensor manifolds 670 and 672 simplify calibration and sensor maintenance. Calibration is accomplished by draining the appropriate manifold and filling it with the proper calibration solution. Dirty or malfunctioning sensors may be replaced without any special tools, even while the RO system is online. It is to be noted that while two integral sensors manifolds are shown, the invention can have one, two, or more and the invention is not to be limited to the two shown. Sensor manifold 670 preferably comprises a permeate sensor manifold having for example, conductivity, temperature, and pH sensors. Sensor manifold 672 preferably comprises a feed water sensor manifold having for example, conductivity, temperature, pH, and ORP sensors. However the invention is not limited to these particular manifolds and sensors. The manifolds receive fluid from, for example an RO system, preferably through flexible nylon tubing, although other types of tubing can be accommodated. Three tube connections are shown generally at 676. These three tubes preferably provide feed water, permeate, and a drain. Preferably the feed water and permeate are fed at 5 psi, 100 ml/min. through ¼ inch outside diameter (OD) tubing, and the drain is ⅜ inch OD tubing. Orifices at the inlet of each manifold 670 and 672 ensure the proper flow rate and a flow switch activates an alarm if the flow rate falls below a preprogrammed setpoint.

Figure 37:
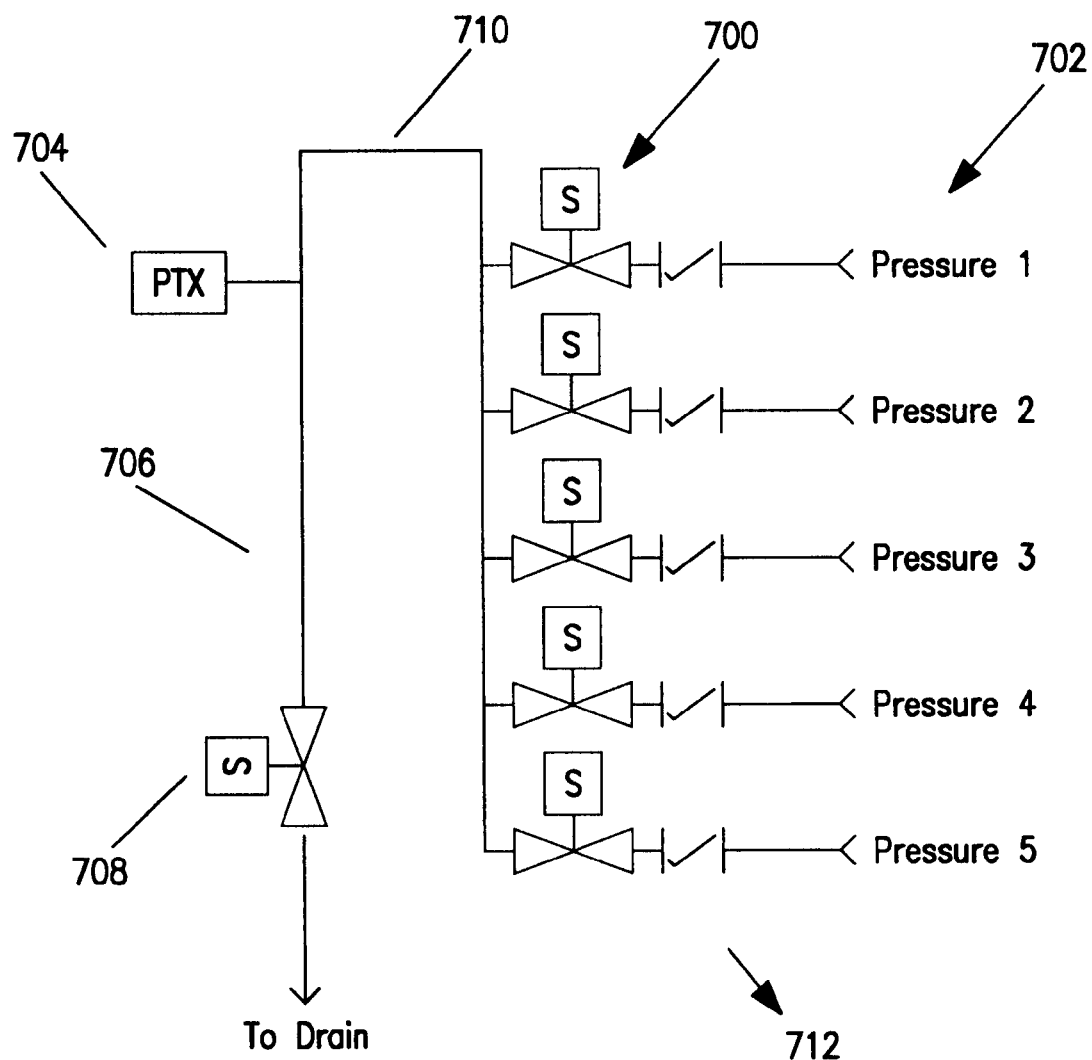
FIG. 37 is a diagram showing the operation of the pressure sensing manifold of the second embodiment of the present invention.

Pressures are also monitored with integral sensors. Pressure connections are shown generally at 674. Membrane feed pressure, interstage pressure, concentrate pressure, and permeate pressure are connected preferably through ⅛ inch OD nylon tubing as shown at 674. The pressure sensing manifold, not shown in FIG. 36 but preferably located behind 674, is equipped with pressure inlet solenoid valves, wherein each valve is connected via tubing to the system to be monitored, such as RO process piping. Attention is now turned to FIG. 37. A single pressure transmitter 704 is connected to outlet 710 of pressure sensing manifold comprising several inlet pressure solenoid valves 700 (five are shown here). Each of the pressure inlet solenoid valves 700 are connected to a common outlet 710 to pressure transmitter 704. By activating the solenoid valves 700 one at a time, in sequence, and monitoring the resulting analog signal from transmitter 704, the fluid treatment apparatus monitors pressures in a plurality of different locations. Programming in the fluid treatment apparatus controls the action of solenoid valves 700 and monitors which pressure measurement corresponds to the proper source. Check valves 712 on inlet solenoid valves 700 prevent back flow from one pressure inlet of a higher pressure to another of a lower pressure. Pressure connections 702 from the system to be monitored to the inlet valves 700 can be made with flexible ⅛ inch nylon tubing.

By sequencing the valves and monitoring the output of the transmitter at the proper time, four separate pressure measurements can be made with the single transmitter. This lowers cost of the system, provides for more accurate differential pressure measurement, and simplifies calibration.

FIG. 38 shows fluid treatment apparatus 600 communicating directly with PLC 414 via serial connection 602 as described above. In this diagram, apparatus 600 is receiving signals directly from network 692, such as an RS-485/422 network. Network 692 comprises a series of input/output modules shown generally at 690, such as pressure input, flow input, pH/ORP input, and conductivity input modules.

The invention is designed to monitor conductivity by means of a standard two electrode conductivity cell. The cell should be equipped with a two-wire, 1000 ohm Pt RTD. Conductivity cells should be connected by means of Belden cable no. 8724 or equivalent. When routing the conductivity cables, stay clear of AC cables, motors, or other sources of electrical interference. It is best never to run sensor cables in the same conduit as AC cables.

The invention accepts signals from three flow sensors providing sinking pulse (24 VDC) signals. The invention accepts signals from four analog transmitters producing 4–20 mA signals. Since a number of transmitters are available, it is important to know how each is wired to the invention. The two-wire transmitter receives power from the invention and sends the analog current signal back via the negative connection of the transmitter. Any two-wire transmitter used with the invention must be isolated from ground potential. A 100 mA fuse should be wired into the power going to the transmitter. The three-wire transmitter preferably receives power from the invention, however, it sends the signal back to the invention on a separate connection from the negative connection of the transmitter. It must therefore have a third connection which goes to the Analog Ground terminal of the invention. Preferably, a 100 mA fuse should be wired into the power going to the transmitter. As in the case of the two-wire transmitter, the three wire transmitter must be isolated from ground potential.

Some transmitters include their own power supply. These may be used with the invention; however, they must produce an isolated 4–20 mA signal.

Finally, it is possible to use a two-wire transmitter powered by a power source other than the invention. This is possible; however, the transmitter power supply must either be isolated from ground potential or be at the same ground potential as the invention. This is assured by connecting the negative side of the transmitter power supply to the same ground as that connected to the negative side of the power supply.

Industrial Applicability

The invention is further illustrated by the following non-limiting examples.

Figure 12:
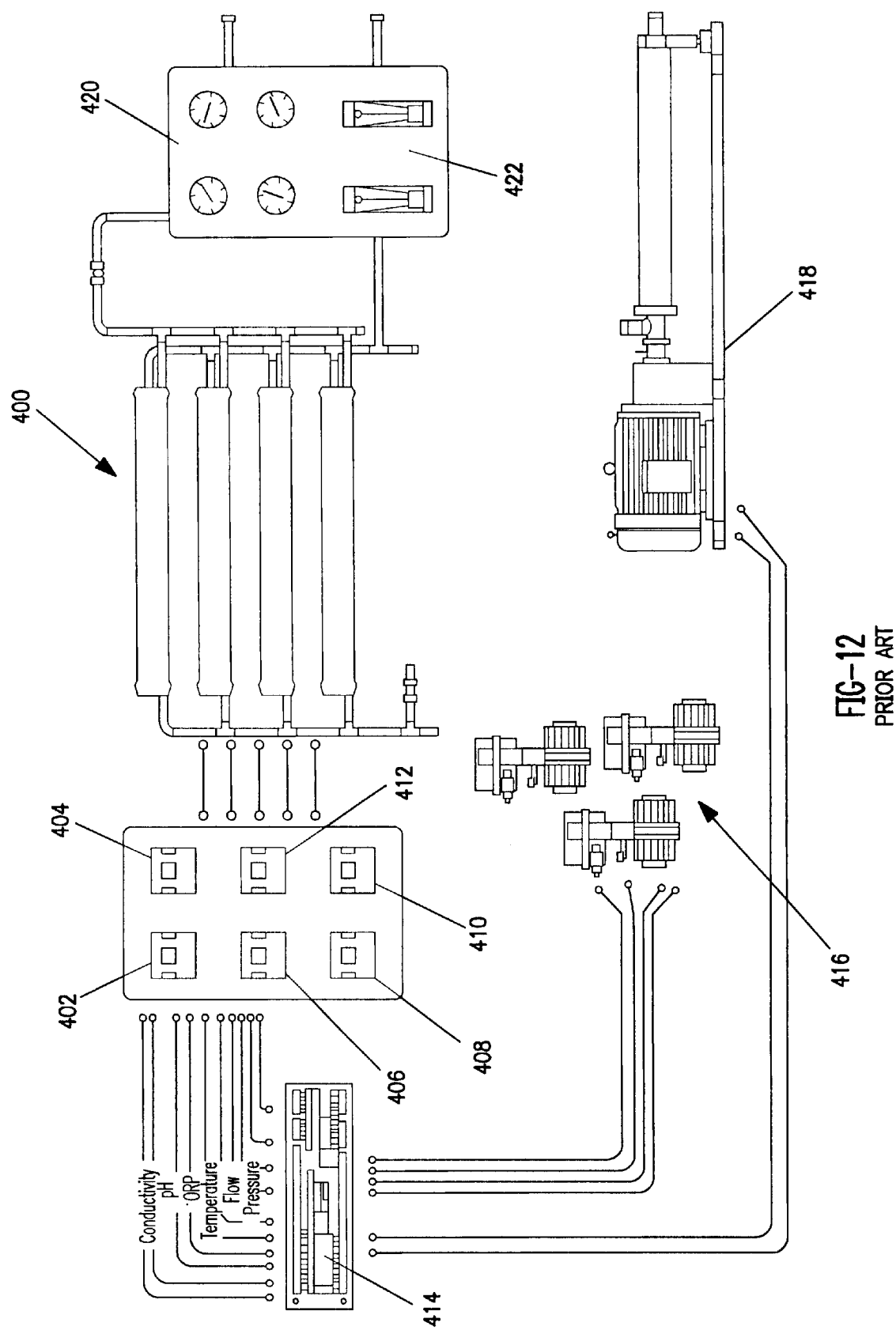
FIG. 12 shows a conventional reverse osmosis system.

FIG. 12 shows a conventional reverse osmosis system. (See also the diagram of FIG. 26 discussed above.) Reverse osmosis vessels are shown generally at 400 and are monitored by pressure gauges 420 and flow meters 422. Various devices are used to monitor the entire system, including conductivity 402, pH 404, ORP 406, flow 408, pressure 410, and temperature 412, which in turn communicate with PLC 414. The PLC then controls motorized valves 416 and high pressure pump 418. With this type of system, many different gauges, meters and discrete devices are required to monitor and control the system.

Figure 13:
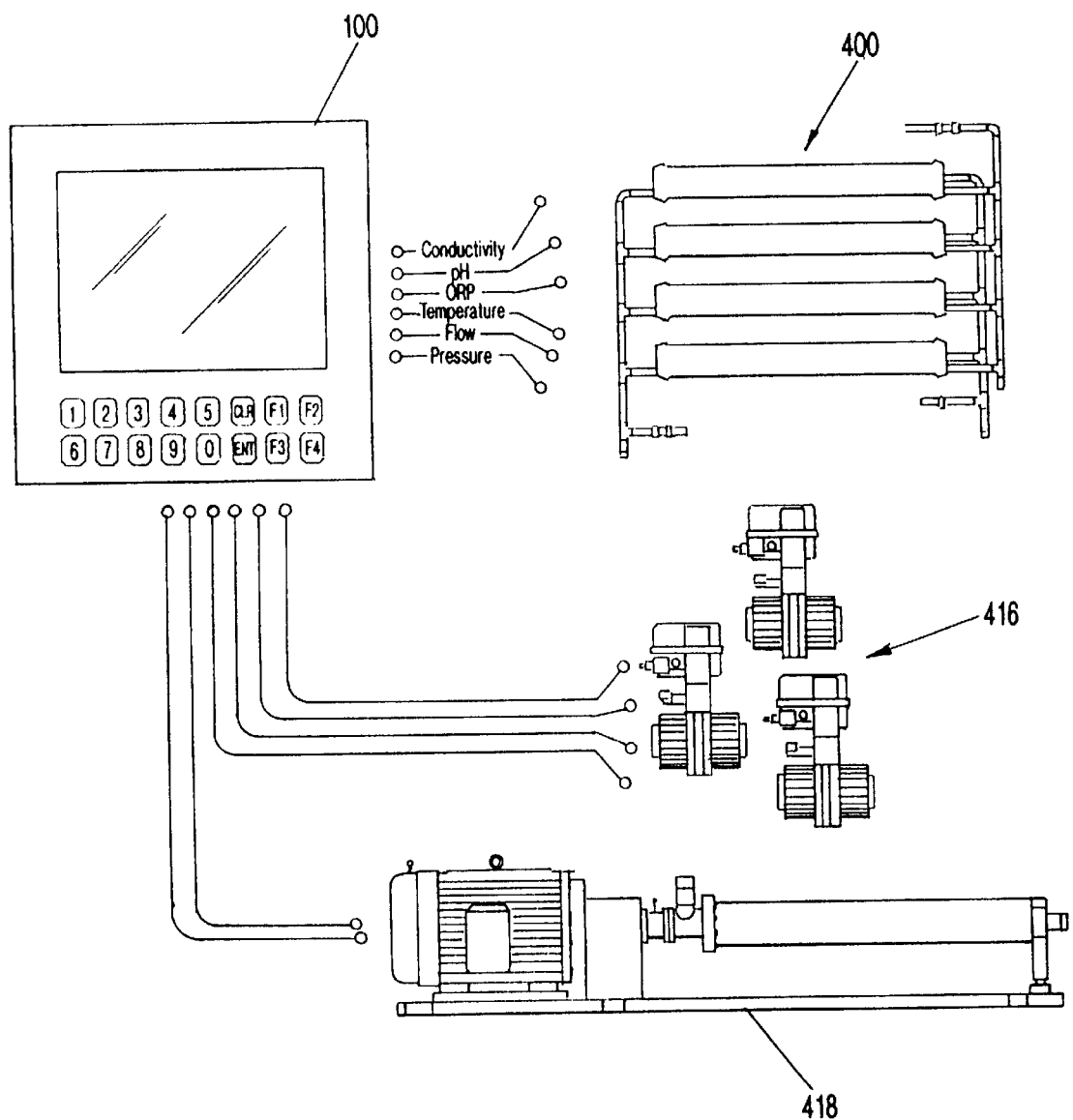
FIG. 13 shows a reverse osmosis system using the first embodiment of the present invention.

FIG. 13 shows an improvement on the conventional reverse osmosis system of FIG. 12 by using the first embodiment of fluid treatment apparatus 100 of the present invention. Fluid treatment apparatus 100 communicates directly with analytical sensors on reverse osmosis vessels 400 and directly with motorized valves 416. Apparatus 100 also communicates directly with high pressure pump 418. With this configuration, cost is reduced. There are fewer wires, fewer pipes, and no PLC or PLC operator interface is required. Apparatus 100 is able to calculate values such as normalized permeate flow, differential pressure, and salt rejection and can also log data. Fluid treatment apparatus 100 may be connected to another system via the modem communication.

Figure 14:
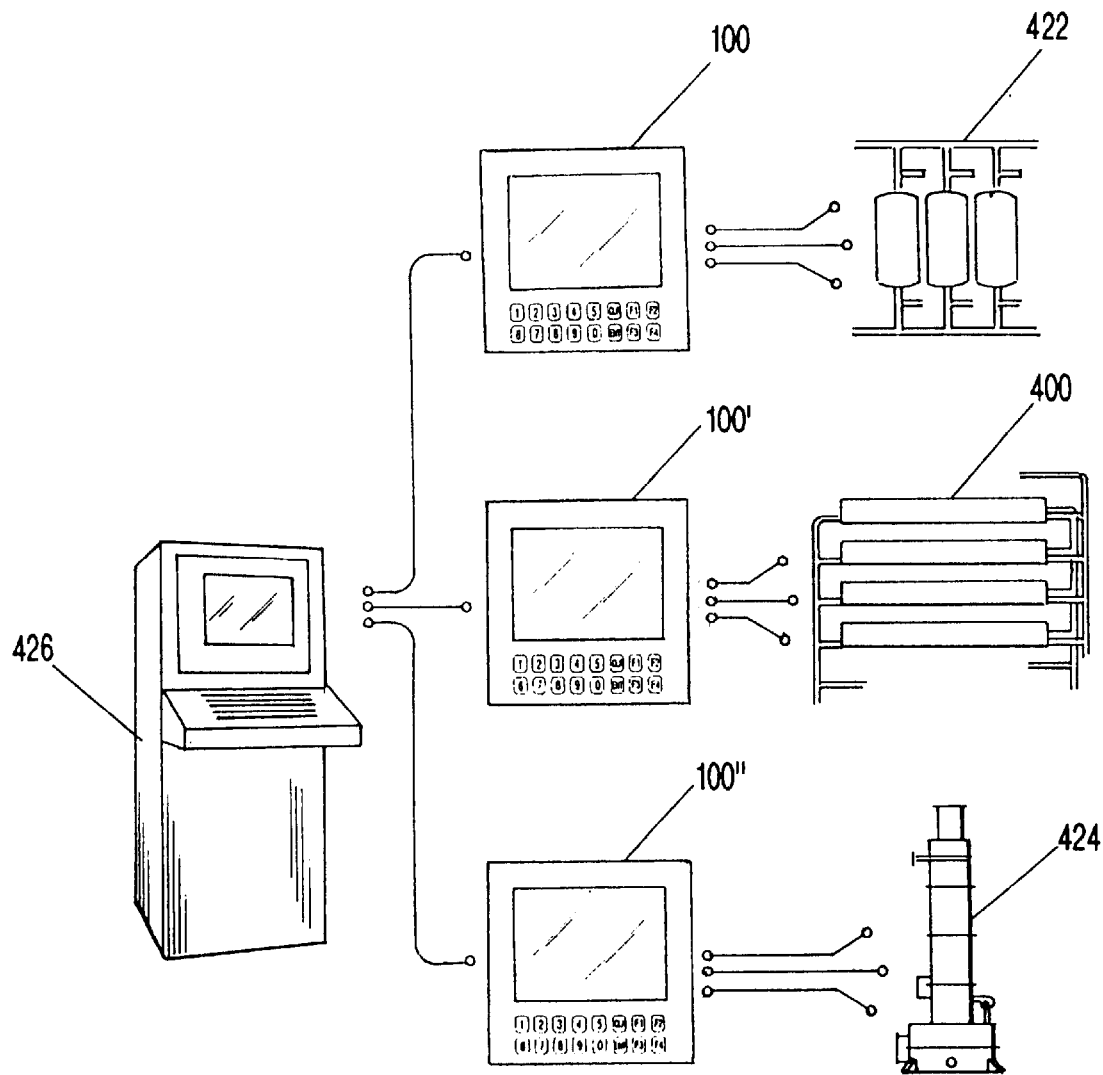
FIG. 14 shows a networking application using the first embodiment of the present invention.

FIG. 14 shows another application of fluid treatment apparatus 100 of the present invention. In this example, three apparatuses 100, 100', 100", are networked in a reverse osmosis system. Fluid is pretreated at 422 and communicates directly with apparatus 100. Reverse osmosis vessels 400 communicate directly with apparatus 100' and post-treatment occurs at 422, which also communicates directly with the network via apparatus 100". All three apparatuses 100, 100' and 100" communicate with industrial personal computer 426. With such a networking system, cost is reduced and the entire treatment system is controlled and monitored from a central position. Less wiring is required and the ability to interface with existing control systems is accomplished.

Figure 15:
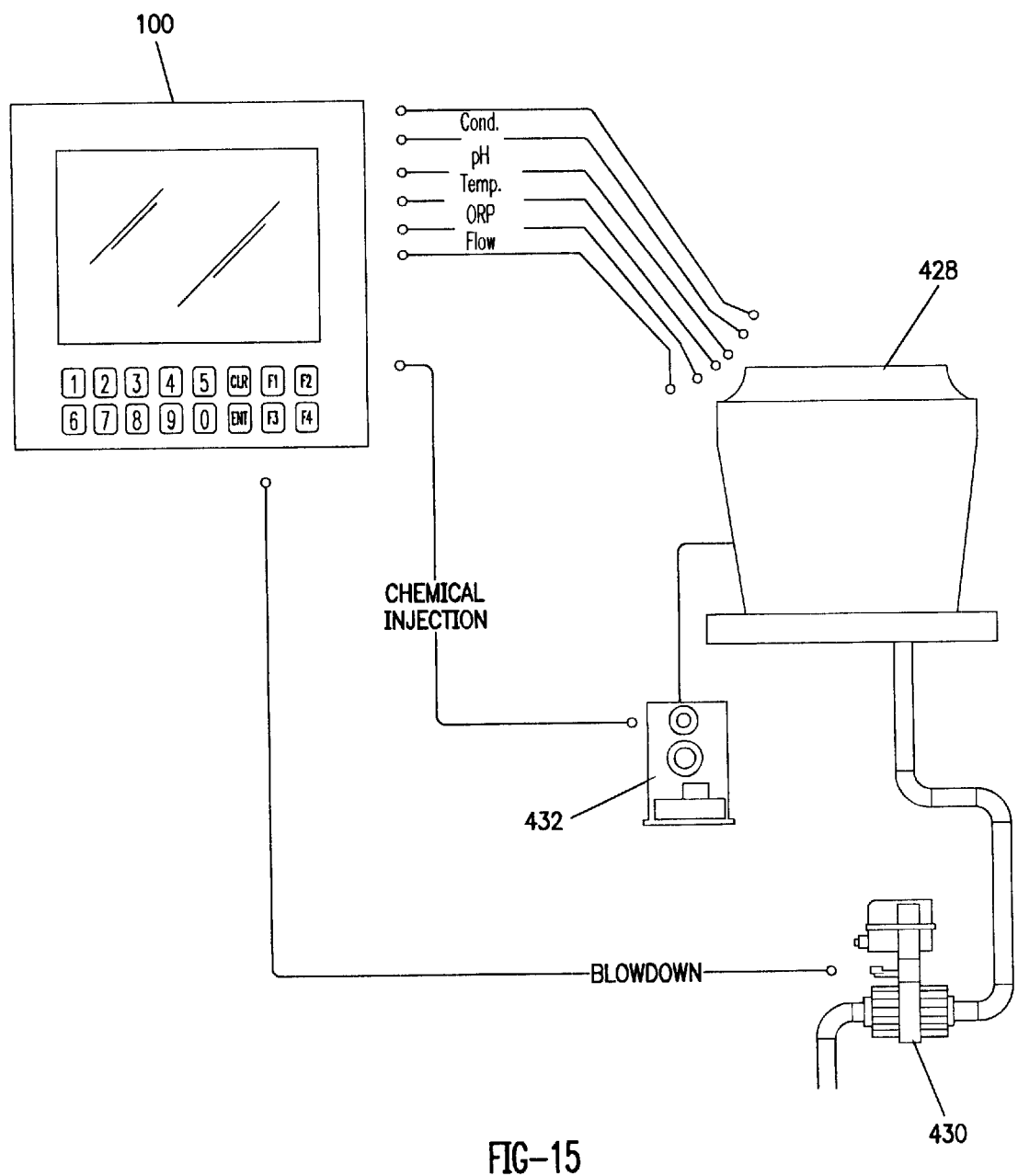
FIG. 15 shows a cooling tower application using the first embodiment of the present invention.

FIG. 15 demonstrates yet another application for fluid treatment apparatus 100. In this application, apparatus 100 communicates directly with cooling tower 428, chemical injection pump 432, and valve 430. With this system, chemical injection can be controlled and chemical costs are decreased. This system can also be remotely monitored via the modem connection.

The preceding examples can be repeated with similar success by substituting the generically or specifically described operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A fluid monitoring and control system comprising:
   a programmable and reprogrammable control unit comprising display means, user input means, and input/output connectors;
   a programmable logic controller in direct communication with said control unit; and
   a plurality of fluid parameter sensors in direct communication with said control unit.

2. The system of claim 1 wherein said control unit comprises a serial port for direct communication with said programmable logic controller.

3. The system of claim 1 wherein said control unit comprises a network connection port for direct communication with said plurality of fluid parameter sensors.

4. The system of claim 1 wherein said programmable logic controller receives no inputs other than from said control unit.

5. The system of claim 1 additionally comprising an integral housing to which said control unit and said plurality of sensors are attached and through which flows a fluid stream whose parameters are being sensed by said sensors.

6. The system of claim 1 wherein said plurality of sensors comprises a pressure sensing manifold cycling through a plurality of solenoid valves but requiring only a single input/output connection to said control unit.

7. A fluid control system comprising means for estimating salt rejection by a membrane wherein said estimating means comprises means for calculating one or more of the group consisting of recovery, differential pressure (DP), and normalized permeate flow (NPF).

8. The system of claim 7 additionally comprising means for detecting excessive changes in said salt rejection.

9. The system of claim 7 wherein said estimating means comprises means for detecting a concentration of dissolved solids in a permeate ($C_P$), in feed water ($C_F$), and in reject flow ($C_R$).

10. The system of claim 9 wherein said estimating means comprises means for calculating $C_P/((C_F+C_R)/2)$.

11. A fluid monitoring and control method comprising the steps of:
   providing a programmable and reprogrammable control unit comprising display means, user input means, and input/output connectors;
   placing a programmable logic controller in direct communication with the control unit; and
   placing a plurality of fluid parameter sensors in direct communication with the control unit.

12. The method of claim 11 wherein the providing step comprises providing a control unit comprising a serial port for direct communication with the programmable logic controller.

13. The method of claim 11 wherein the providing step comprises providing a control unit comprising a network connection port for direct communication with the plurality of fluid parameter sensors.

14. The method of claim 11 wherein placing the programmable logic controller in direct communication with the control unit excludes all inputs other than from the control unit.

15. The method of claim 11 additionally comprising providing an integral housing to which the control unit and the plurality of sensors are attached and through which flows a fluid stream whose parameters are being sensed by the sensors.

16. The method of claim 11 wherein placing the plurality of sensors comprises providing a pressure sensing manifold cycling through a plurality of solenoid valves but requiring only a single input/output connection to the control unit.

17. A fluid control method comprising the steps of providing a membrane and estimating salt rejection by the membrane wherein the estimating step comprises calculating one or more of the group consisting of recovery, differential pressure (DP), and normalized permeate flow (NPF).

18. The method of claim 17 additionally comprising detecting excessive changes in the salt rejection.

19. The method of claim 17 wherein the estimating step comprises detecting a concentration of dissolved solids in a permeate ($C_P$), in feed water ($C_F$), and in reject flow ($C_R$).

20. The method of claim 19 wherein the estimating step comprises calculating $C_P/((C_F+C_R)/2)$.

21. A fluid control system comprising means for estimating salt rejection by a membrane wherein said estimating means comprises means for detecting a concentration of dissolved solids in a permeate ($C_P$), in feed water ($C_F$), and in reject flow ($C_R$) and wherein said estimating means comprises means for calculating $C_P/((C_F+C_R)/2)$.

22. A fluid control method comprising the steps of providing a membrane and estimating salt rejection by the membrane wherein the estimating step comprises detecting a concentration of dissolved solids in a permeate ($C_P$), in feed water ($C_F$), and in reject flow ($C_R$) and wherein the estimating step comprises calculating $C_P/((C_F+C_R)/2)$.

* * * * *